US010018546B2

(12) United States Patent
Honda et al.

(10) Patent No.: US 10,018,546 B2
(45) Date of Patent: Jul. 10, 2018

(54) PROPELLANT GAUGING AT MICROGRAVITY WITHIN THE PRESSURE-TEMPERATURE-DENSITY INFLECTION ZONE OF XENON

(71) Applicant: The Boeing Company, Chicago, IL (US)

(72) Inventors: Linton Kaneki Honda, Rancho Palos Verdes, CA (US); Steven Edward Core, Redondo Beach, CA (US); Gregory Cardon McDonald, Spring Dale, UT (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/137,945

(22) Filed: Apr. 25, 2016

(65) Prior Publication Data

US 2016/0238505 A1 Aug. 18, 2016

Related U.S. Application Data

(63) Continuation of application No. 13/658,758, filed on Oct. 23, 2012, now Pat. No. 9,334,069.

(51) Int. Cl.
*F02K 9/44* (2006.01)
*B64G 1/40* (2006.01)
(Continued)

(52) U.S. Cl.
CPC ............... *G01N 9/36* (2013.01); *B64G 1/402* (2013.01); *B64G 1/405* (2013.01); *F02K 9/44* (2013.01); *G01G 9/00* (2013.01); *B64G 1/22* (2013.01)

(58) Field of Classification Search
CPC ........ B64G 1/402; B64G 1/401; B64G 1/405; F02K 9/50; F02K 9/44; F17C 2250/043; F17C 2250/0439
(Continued)

(56) References Cited

U.S. PATENT DOCUMENTS 4,827,762 A 5/1989 Hasselmann
5,158,362 A * 10/1992 Brauer .................. B64G 1/402 244/172.2

(Continued)

OTHER PUBLICATIONS

Office Action, issued by the United States Patent and Trademark Office in connection with U.S. Appl. No. 13/658,758, dated Jun. 3, 2015, 16 pages.

(Continued)

*Primary Examiner* — Roy Y Yi
*Assistant Examiner* — Jeffrey Aiello
(74) *Attorney, Agent, or Firm* — Hanley, Flight & Zimmerman, LLC

(57) ABSTRACT

A method that is stored in tangible form and accessible by a data processing system for determination of xenon propellant remaining in a tank for a defined life condition. A heater controller establishes a first stable temperature of a propellant tank. A measurement is performed of a temperature and a pressure at the first stable temperature of the propellant tank. A second higher stable temperature is provided in the propellant tank. A measurement is performed of a temperature and a pressure at a second stable temperature. A computer processor computes a mass based on density and volume in accordance with measurements of temperature and pressure at the first stable temperature and the second stable temperature.

17 Claims, 7 Drawing Sheets

10
12
26
16
22
24
18
20
14

(51) Int. Cl.
*G01N 9/36* (2006.01)
*G01G 9/00* (2006.01)
*B64G 1/22* (2006.01)

(58) Field of Classification Search
USPC ...... 60/204; 244/158.1, 171.1, 172.3, 172.2; 702/55
See application file for complete search history.

(56) References Cited

U.S. PATENT DOCUMENTS 5,505,180 A * 4/1996 Otterman ............ F02D 41/2464 123/497
5,700,088 A 12/1997 Piacente et al.
5,810,058 A * 9/1998 Kountz ..................... F17C 5/06 141/18
6,518,693 B1 * 2/2003 Meyer ................... F03H 1/0075 313/359.1
6,557,530 B1 * 5/2003 Benson ................... F02D 41/22 123/447
6,609,363 B1 8/2003 Dressler et al.
8,781,652 B2 7/2014 Vu
2002/0011094 A1 1/2002 Cook et al.
2004/0035982 A1 2/2004 Capozzi et al.
2005/0112027 A1 * 5/2005 Arii ....................... H01J 49/049 422/80
2005/0164056 A1 * 7/2005 Tanaka ............. H01M 8/04029 429/414
2006/0212233 A1 * 9/2006 Wong ........................ G01F 1/34 702/50
2006/0263283 A1 * 11/2006 Egan ....................... B01F 3/026 423/210
2008/0140336 A1 6/2008 Home
2009/0031700 A1 2/2009 Karabeyoglu
2009/0079783 A1 * 3/2009 Mehta ........................ B41J 2/04 347/21
2009/0099498 A1 * 4/2009 Demers ................. A61M 1/106 604/6.09
2009/0133788 A1 5/2009 Mungas et al.
2010/0000232 A1 1/2010 Valentian
2010/0212404 A1 * 8/2010 Wolford .................. G01M 3/00 73/45.5
2011/0070063 A1 * 3/2011 Snuttjer .................. F01D 17/08 415/1
2013/0186471 A1 * 7/2013 Nagase ..................... G01F 1/34 137/2
2014/0032092 A1 1/2014 Vu
2014/0174152 A1 * 6/2014 Gil ........................... G01N 7/00 73/25.01

OTHER PUBLICATIONS

Notice of Allowance and Fee(s) Due, issued by the United States Patent and Trademark Office in connection with U.S. Appl. No. 13/658,758, dated Jan. 8, 2016, 9 pages.

* cited by examiner

PROPELLANT GAUGING AT MICROGRAVITY WITHIN THE PRESSURE-TEMPERATURE-DENSITY INFLECTION ZONE OF XENON

RELATED APPLICATION

This patent arises from a continuation of U.S. application Ser. No. 13/658,758, titled "Propellant Gauging at Microgravity Within the Pressure—Temperature—Density Inflection Zone of Xenon," filed Oct. 23, 2012, which is incorporated herein by this reference in its entirety.

FIELD

Embodiments of the disclosure relate generally to the field of propellant mass remaining calculation for propellant (such as xenon) tanks and more particularly to a method for calculating mass of xenon as a non-ideal gas using controlled temperature differential to induce associated pressure differential allowing an iterative differential pressure and temperature calculation with known tank volume to back calculate xenon mass remaining.

BACKGROUND

Xenon thrusters are employed in many spacecraft applications for station keeping and on-orbit maneuvering. Xenon used as a propellant is a non-ideal gas. Propellant quantity gauging for xenon in microgravity is therefore very difficult along the pressure-temperature-density inflection zone because small changes in pressure or temperature can change the calculated density by over 100%. Diurnal effects impact gauging measurements due to changing environmental conditions of the spacecraft. Additionally, small biases or inaccuracies in the telemetry can also cause significant uncertainty in mass remaining. Current quantity gauging is accomplished by book-keeping methods subtracting estimated amounts of propellant processed during each thruster operation for defining remaining quantity of propellant until quantity and associated pressure in the tank drops below approximately 1 MPa at which point ideal gas calculations for mass based on pressure, volume, density, and temperature can be assumed with reasonable accuracy.

It is therefore desirable to provide a method for calculation of xenon mass in a propellant tank which corrects for non-ideal gas properties and sensor biases for a range of propellant quantities in which ideal gas calculations cannot be accurately used.

SUMMARY

Embodiments disclosed herein provide a method for determination of xenon propellant remaining in a tank for a defined spacecraft on-orbit service life condition by establishing a first stable temperature of a propellant tank. Measurement of temperature and pressure at the first fixed temperature is accomplished. A second higher stable temperature is then established in the propellant tank. Measurement of temperature and pressure is then accomplished at the higher temperature. The two measurements of temperature and pressure are then used to calculate the mass of remaining propellant based on known xenon density properties and tank volume.

The features, functions, and advantages that have been discussed can be achieved independently in various embodiments of the present disclosure or may be combined in yet other embodiments further details of which can be seen with reference to the following description and drawings.

DETAILED DESCRIPTION

Figure 1:
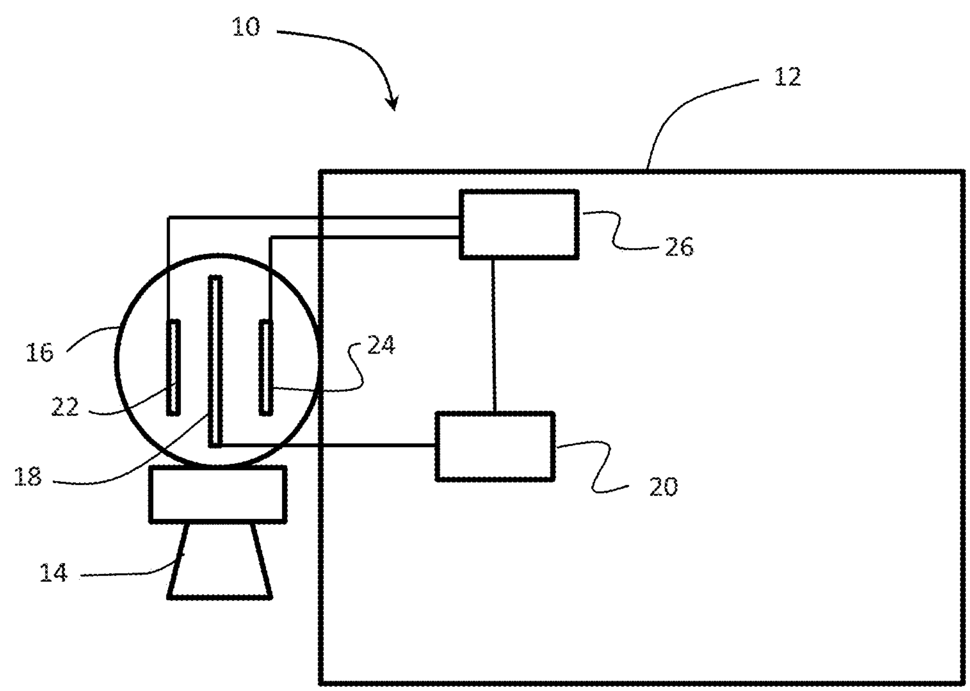
FIG. 1 is a block diagram schematic of a spacecraft xenon propellant feed system.

Embodiments disclosed herein provide a method for calculating the remaining mass in a xenon propellant tank in a quantity range in which ideal gas behavior is not present. As shown in FIG. 1, an example satellite system 10 employs a spacecraft platform 12 containing scientific experiments, communication system or other satellite payload. Included on the platform are xenon thrusters 14 (one is shown as an example but numerous thrusters at various locations on the platform and with varying thrust axes are employed). A propellant tank 16 holds xenon propellant for the thrusters. Within the tank a heater element 18 is present to allow tank temperature control and resulting pressure control. Tank temperature control may be augmented with thermal blankets. A heater controller 20 provides controlled power to the heater. A temperature sensor 22 and a pressure sensor 24 in the tank measure temperature and pressure and provide data to a control computer 26. The control computer is connected to the heater controller for control of the heater to achieve desired temperatures within the tank.

Figure 2:
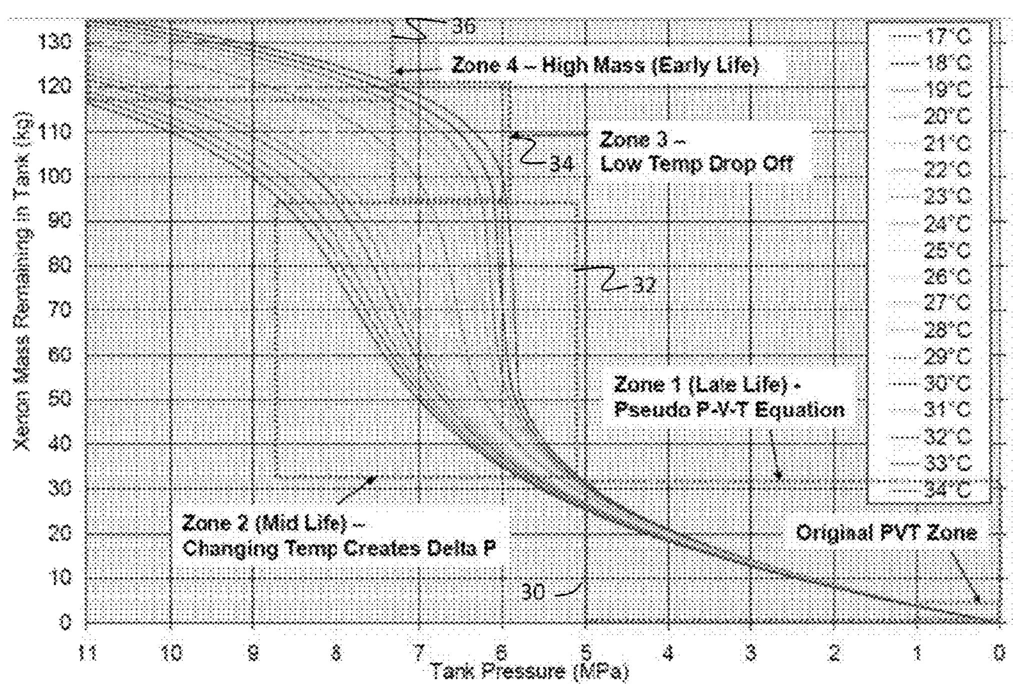
FIG. 2 is a graphical representation of the relationship between temperature, pressure and mass for xenon in an example tank of known volume using pure xenon density properties.

The amount of xenon propellant remaining in the tank 16 needs to be known to properly plan satellite control using the thrusters 14. However, xenon is not an ideal gas. Consequently, usual gaseous propellant gauging techniques using temperature, pressure and the known volume of the propellant tank are not effective for the majority of the usable range of propellant quantity. FIG. 2 shows the non-ideal nature of xenon for an example propellant tank having an initial quantity of approximately 135 kg of xenon with curves for parametric temperatures plotted against pressure and corresponding mass remaining in the tank. Since knowledge of remaining quantity of propellant becomes more critical as the total available propellant approaches exhaustion, zones of propellant quantity (or depletion zones) have been established based on criticality of the measurement and availability of measurement techniques. As shown in FIG. 2, Zone 1, within block 30, where the tank nears exhaustion of propellant, is established in a pressure regime in which ideal gas behavior may be approximated and used for measurement of the remaining propellant quantity. Zone 2, within block 32, is the zone where husbanding of propellant and knowledge of quantity remaining is most difficult to ascertain to assure desired mission service life longevity, constitutes the zone for which the present embodiments are most useful. Zone 3, within block 34, referred to as the low temperature drop off point, is a limited range and near the full condition in which accurate gauging is not as critical. Zone 4, within block 36, is the early life condition where the tank is nearly full and book-keeping methods, tabular look up or pseudo polynomial calculations based on pressure and temperature may be used to estimate propellant quantity.

Figure 3:
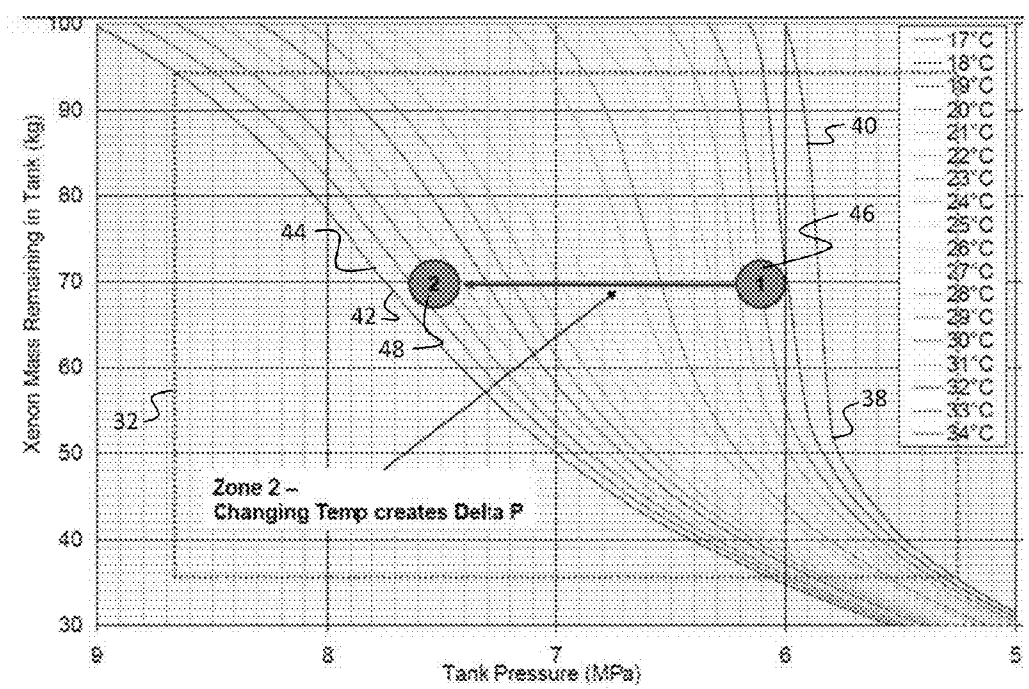
FIG. 3 is a detail section graphical representation of the Zone 2 Midlife portion of FIG. 2.

Examining zone 2 in detail in FIG. 3 it can be seen that at lower temperatures and a given pressure, the mass remaining varies extensively (near vertical slope). For example with a temperature of 17° C. a pressure differential of 0.1 MPa between 5.8 and 5.9 MPa can have a mass range of approximately 52 kg, point 38, to 86 kg, point 40 in mass remaining. However, at 34° C. that same pressure differential of 0.1 MPa between 7.7 and 7.8 MPa only has a mass range of approximately 69 kg, point 42, to 71 kg, point 44. By determining the pressure differential created by an induced temperature differential it is then possible to determine an associated mass remaining with a significantly higher degree of accuracy. Demonstrated graphically in FIG. 3, by establishing and maintaining a tank temperature of 19° C. using the heater element 18 under control of the heater controller 20 if 70 kg xenon is in the tank, a pressure of 6.1 MPa, point 46, will be measured. Increasing the temperature to a new stabilized point of 32° C. and measuring the resulting pressure as 7.55 MPa, point 48, allows a determination that the mass is, in fact, 70 kg of xenon. Since there is no change in mass (or negligible change since actual usage of xenon over a couple of days of station-keeping maneuvering for thruster burns is very small), the determined change in pressure (delta P) for a given change in temperature (delta T) can only occur at a specific mass remaining. While described herein for xenon as the propellant, the structure and method disclosed in the embodiments is applicable for gauging of mass remaining for alternative gases having non-ideal characteristics with a significant S-curve or inflection and spread in the temperature, pressure and density as demonstrated in FIG. 3.

Figure 4:
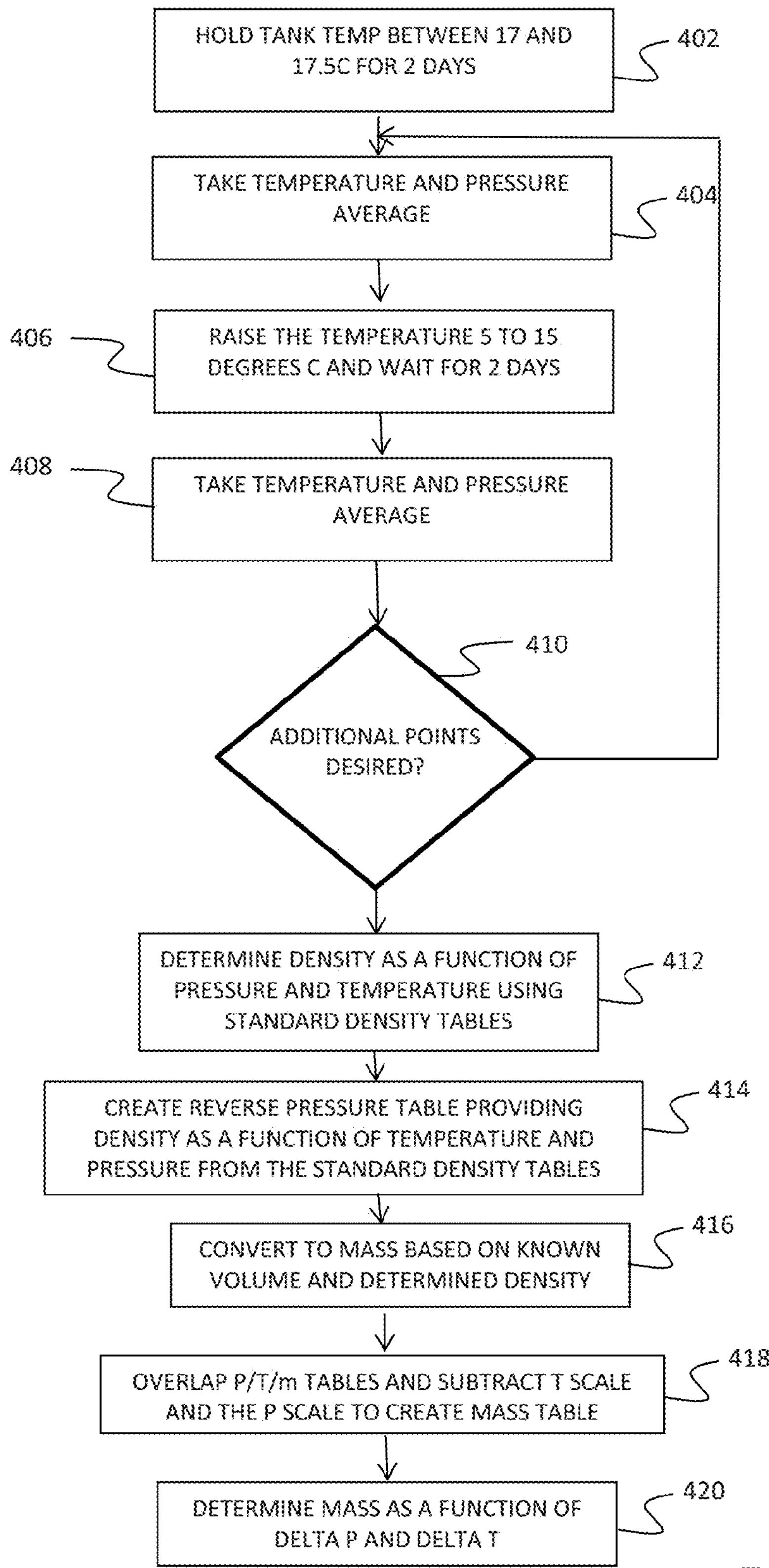
FIG. 4 is a flow chart showing the determination of mass remaining in a tank based on measured temperature and pressure change.

Employing this relationship, calculation of remaining xenon propellant in the tank can be accomplished as defined in FIG. 4. Using the heater controller 20 to control the heater element 18, establish and hold tank temperature as measured by the temperature sensor 22 at an initial temperature (for the example case, between 17 and 17.5° C.), step 402. Measure temperature and pressure average over a approximately a two day period, step 404. Raise the temperature by a delta T of 5 to 15 degree C. and hold for approximately 2 days, step 406. Measure temperature and pressure average, step 408. Steps 404 through 408 may be repeated to obtain additional measurement points, step 410. For each stabilized temperature a density is then determined as a function of pressure and temperature using standard density tables, step 412. A reverse pressure table providing density as a function of temperature and pressure is created from the standard density tables, step 414. The known volume of the propellant tank as a function of pressure and temperature allows xenon propellant mass to be determined from corresponding density in the pressure/temperature/density tables and substituted in either or both tables, step 416. Pressure/temperature/mass tables are then overlapped and the temperature scale and pressure scale are subtracted to create a mass table, step 418 (a detailed example will provided subsequently). The mass remaining is then determined as a function of delta P and delta T, step 420.

Figure 5:
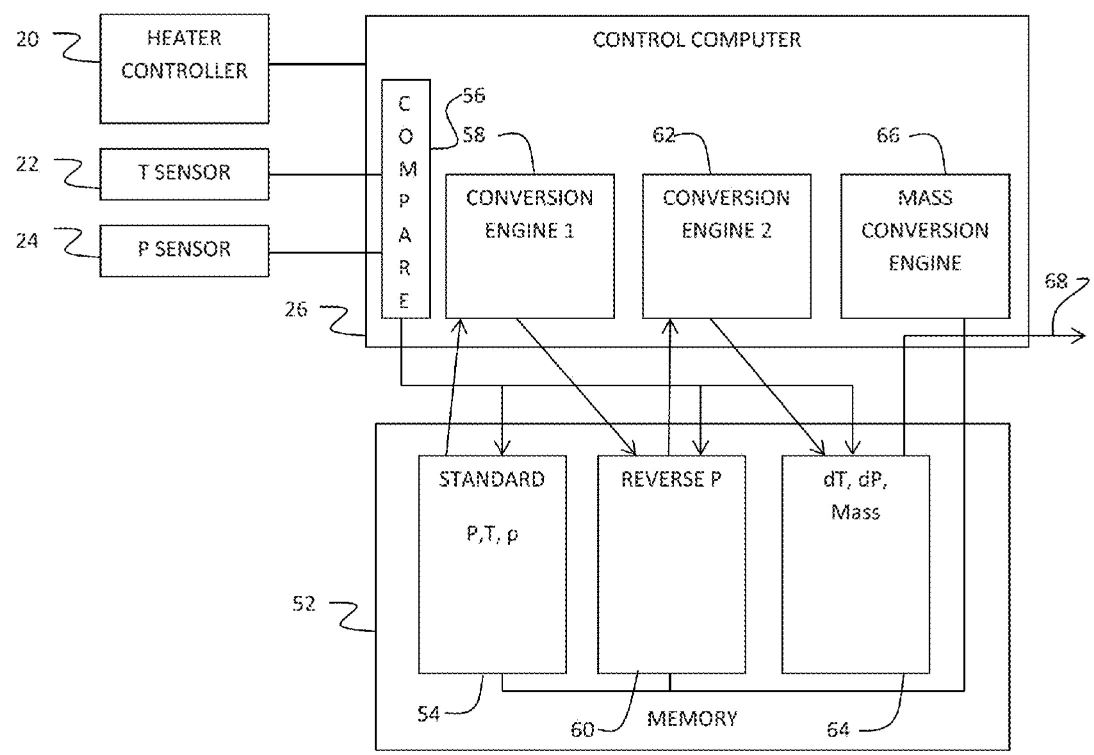
FIG. 5 is a block diagram of elements of the propellant mass gauging system.

As shown in FIG. 5, implementation of an embodiment of the xenon propellant zone 2 gauging system is accomplished with the heater controller 20 under direction of a control computer 26 which receives input from the temperature sensor 22 and pressure sensor 24. The spacecraft or ground-based control computer 26 employs a memory 52 storing a standardized pressure/temperature/density table 54 for xenon in zone 2. The control computer 26 commands the heater controller 20 to maintain desired temperatures at a selected series of hold points as defined previously with respect to FIG. 4. Pressure and temperature data from each hold point is operated on by a compare routine 56 using table 54 to obtain a density value for each hold point. A first conversion engine 58 creates and stores a reverse pressure calculation table 60 in memory 52. A mass calculation engine 66 employing measured or calculated volume of the xenon propellant storage tank 16 converts density to mass based on pressure and temperature of the tank in either or both tables 54 and 60. A second conversion engine 62 operates on the data of the reverse pressure calculation table 60 selecting pressure differentials based on temperature differentials to provide a table 64 of mass for each temperature differential, dT, in the hold points as a function of measured pressure differential, dP. The control computer 26 provides an output 68 reflecting remaining mass of xenon in the propellant tank as determined from dP and dT. Examples for tables 54, 60 and 64 with mass conversion as determined by mass calculation engine 66 are provided in appendix 1, appendix 2 and appendix 3, respectively, of this application. As previously described with respect to FIG. 4, appendix 2 is determined from appendix 1 by reversing the pressure and density in the table such that density/mass is shown in the left column as a function of temperature in the first row and associated pressures in the table body. Conversion of density to mass using known volume of the example tank at the corresponding pressures and temperatures is accomplished at the table of appendix 1 for this example. Appendix 3 is determined from appendix 2 by subtracting the temperature columns of appendix 2 as a function of mass (or density) from the initial column (i.e. 35.1C column minus the 17.2C column). The pressure within each row of a temperature column is also subtracted giving a delta pressure row in the table body of appendix 3. The resulting array in appendix 3 is expressed as a function of delta T and delta P. For appendix 3, the arrays are then rearranged so that for given delta T and P, a mass is then found in the left most column of the table. For example in Appendix 3, for 18C delta (the furthest right column and 1.675 MPa delta pressure highlighted, the mass is found to the left to be 61.4 kg.

EXAMPLE 1

An exemplary determination of remaining mass of xenon propellant using the xenon propellant zone 2 gauging system as described was made. Temperature of the exemplary tank was set by the heater controller at 17.25° C.+/−0.25° C. Data was recorded every minute for approximately 2 days to establish steady state conditions of the tank. Data was recorded for approximately 2 days and an average pressure and temperature of approximately 5.7 MPa at 17.2° C. was obtained. As a reference a standard mass calculation using available NIST 12 pure xenon density property tables and tank volume for the stabilized pressure and temperature indicates a mass remaining of 50.6 kg+/−20 kg. A second temperature of 35.25° C.+/−0.25° C. was commanded and data recorded for approximately 2 days to demonstrate steady state conditions of the tank. Data was recorded for 2 days at the steady state conditions and an average pressure of approximately 7.4 MPa and average temperature of 35.1° C. was obtained. Again as a reference a calculation using NIST 12 xenon density property tables was made indicating a mass of 58.6 kg+/−10 kg. Using the differential pressure between the two stabilized conditions of 1.7 MPa and differential temperature of 17.9° C. and operating on that differential data with table 64 (appendix 3) as defined herein provided a mass calculation of 61.4 kg+/−3 kg demonstrating significantly greater mass remaining accuracy than individual NIST 12 density and tank volume calculations.

Figure 6:
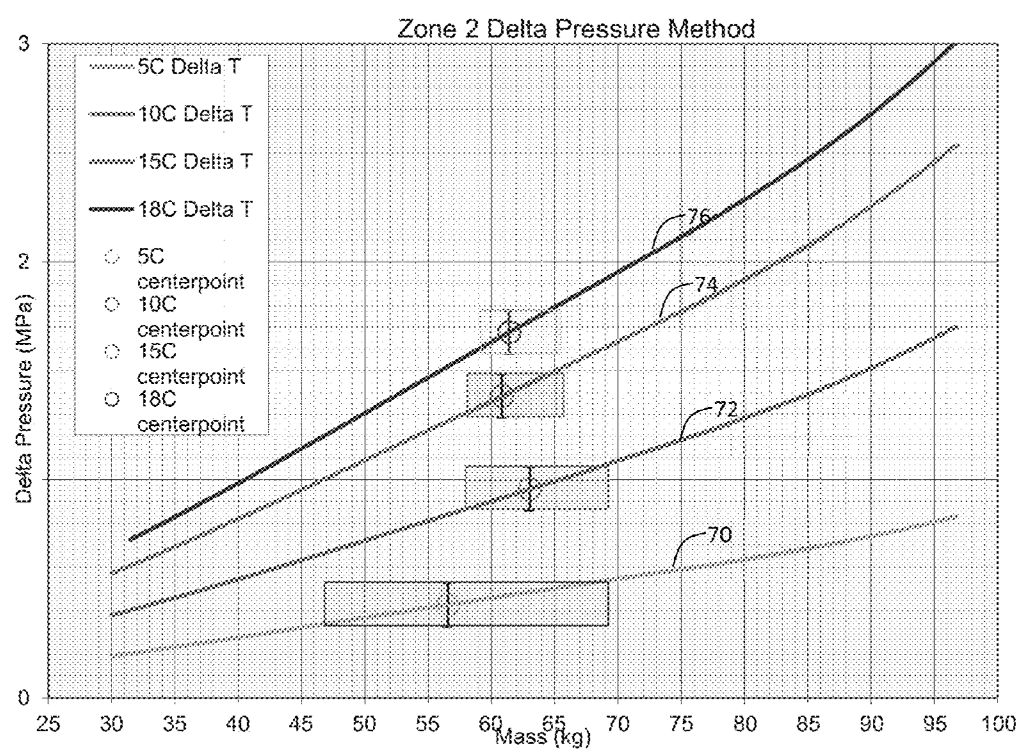
FIG. 6 is a graph of mass remaining at differential pressures based on differential temperatures; and, FIG. 7 is a block diagram of a computer architecture which may be employed for the propellant mass gauging system.

FIG. 6 is a graphical representation of the data provided by table 64. The available uncertainty of the mass remaining data extraction demonstrated by the increasing slope of the curves 70, 72, 74 and 76 for differential temperatures of 5° C., 10° C., 15° C. and 18° C. respectively with greatest mass remaining accuracy (i.e. minimum uncertainty) provided by the largest shown differential temperature at 18° C.

Figure 7:
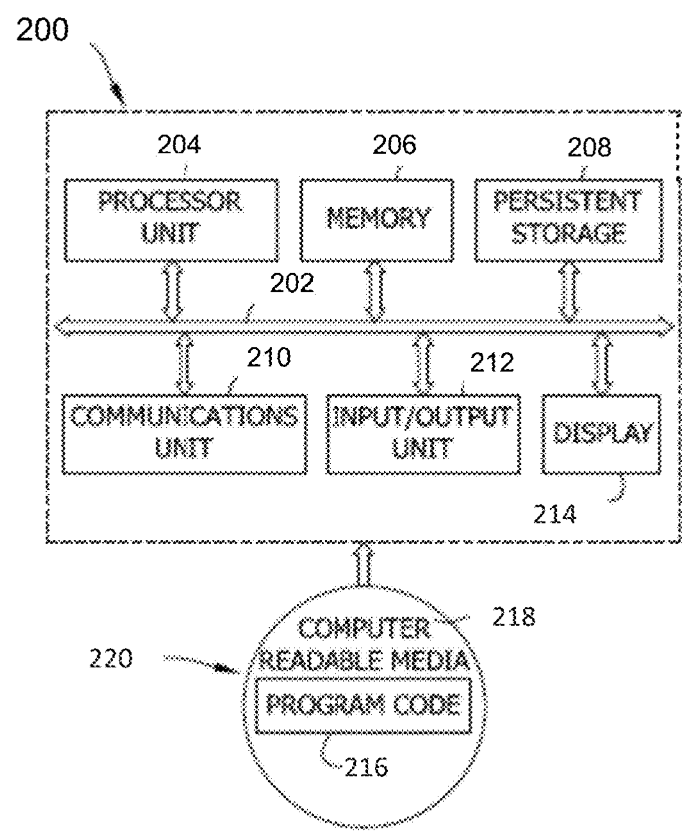

FIG. 7 is a diagram of an exemplary data processing system 200 that may be used in implementing one or more of the embodiments described herein. For example, control of xenon thrusters 14, and heater controller 20, data acquisition from temperature sensor 22, pressure sensor 24, the functions of control computer 26 and memory 52, software modules such as first conversion engine 58, second conversion engine 62, mass calculation table 66, table 54 to obtain density value for each hold point, table 64 of density for each pressure differential, reverse pressure calculation table 60 in memory 52, and/or one or more components integrated in satellite system 10 or xenon propellant Zone 1, 2, 3, 4 gauging system(s) discussed above may be implemented using data processing system 200. In the exemplary embodiment, data processing system 200 includes communications fabric 202 providing communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. In one example, processor unit 204 is implemented using one or more heterogeneous processor systems including a main processor and one or more secondary processors on a single chip.

Processor unit 204 may be a multi-processor system containing multiple, same type processors. Processor unit 204 may be implemented using one or more programmable circuits including one or more systems and microcontrollers, programmable logic circuits, field programmable gate arrays (FPGA), microprocessors, application specific integrated circuits (ASIC), and other like circuits capable of executing the functions described herein.

Memory 206 and persistent storage 208 are examples of storage devices capable of storing information including the software modules either on a temporary basis and/or a permanent basis. In another example, memory 206, may be a random access memory or any other volatile or non-volatile storage device or the like. Persistent storage 208 may take various forms depending on the particular implementation. In one instance, persistent storage 208 may be a fixed or removable hard drive, a flash memory, a rewritable optical disk, a rewritable magnetic tape, or some combination of the above. In one example, a removable hard drive may be used for persistent storage 208.

Input/output unit 212 provides input and output of data with one or more other devices that may be connected to data processing system 200. Input/output unit 212 may provide, for example, without limitation, a connection for user input through a keyboard and mouse. Input and/or output unit 212 may send output to a printer. Display 214 provides a mechanism to display information to a user.

Communications unit 210, in these examples, provides for communications with other data processing systems or devices. In these examples, communications unit 210 is a network interface card. Communications unit 210 may provide communications through the use of either or both physical and wireless communication links. Instructions for the operating system and applications or programs are located on persistent storage 208. Instructions may be loaded into memory 206 for execution by processor unit 204. Processes of various embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 to operate, for example, first conversion engine 58, second conversion engine 62, mass calculation engine 66, or control computer 26 or other components of satellite system 10 is located in a functional form on computer readable media 218 that is selectively removable and may be loaded onto or transferred to data processing system 200 for execution by processor unit 204. Program code 216 and computer readable media 218 form computer program product 220 in these examples. Computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. Computer readable media 218 may take the form of a tangible form including persistent storage, such as a hard drive, a thumb drive, or a flash memory that is connected to data processing system 200. The tangible form of computer readable media 218 is also referred to as computer recordable storage media. In some instances, computer readable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

In some illustrative embodiments, program code 216 may be downloaded over a network to persistent storage 208 from another device or data processing system for use within data processing system 200. For instance, program code stored in a computer readable storage medium in a server data processing system may be downloaded over a network from the server to data processing system 200. The data processing system providing program code 216 may be a server computer, a client computer, or some other device capable of storing and transmitting program code 216.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 7 can be varied from the illustrative examples shown.

In one variant, a storage device in data processing system 200 may be any hardware apparatus that may store data. Memory 206, persistent storage 208 and computer readable media 218 are examples of storage devices in a tangible form. In another example, a bus system may be used to implement communications fabric 202 and may be comprised of one or more buses, such as a system bus or an input/output bus. In another variant, the bus system may be implemented using any type of architecture that provides for a transfer of data between components or devices attached to the bus system. Additionally, a communications unit may include one or more devices used to transmit and receive data, such as a modem or a network adapter. For example and without limitation, memory 206 or a cache such as that found in an interface and memory controller hub that may be present in communications fabric 202. Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

APPENDIX 1

| Standard Mass Calculation | | | | | | |
|---|---|---|---|---|---|---|
| | | Temps | | | | |
| | | 15.1 | 17.2 | 20.1 C. | 25.1 C. | 35.1 C. |
| Pressure | 5 | 32.73903 | 31.41732 | 29.92593 | 27.91992 | 25.06581 |
| | 5.0025 | 32.77913 | 31.45191 | 29.95636 | 27.94483 | 25.0862 |
| | 5.005 | 32.81855 | 31.48649 | 29.98611 | 27.96975 | 25.10558 |
| | 5.0075 | 32.85865 | 31.52176 | 30.01655 | 27.99466 | 25.12497 |
| | 5.01 | 32.89876 | 31.55635 | 30.01699 | 28.02027 | 25.14505 |
| | 5.0125 | 32.93886 | 31.59162 | 30.07674 | 28.04518 | 25.16444 |
| | 5.015 | 32.97897 | 31.62689 | 30.10718 | 28.07079 | 25.18383 |
| | 5.0175 | 33.01908 | 31.66148 | 30.13762 | 28.09571 | 25.20391 |
| | 5.02 | 33.05918 | 31.69675 | 30.16807 | 28.12062 | 25.2233 |
| | 5.0225 | 33.09998 | 31.73202 | 30.19851 | 28.14623 | 25.24337 |
| | 5.025 | 33.14078 | 31.76799 | 30.22895 | 28.17183 | 25.26276 |
| | 5.0275 | 33.18157 | 31.80326 | 30.26008 | 28.19675 | 25.28284 |
| | 5.03 | 33.22237 | 31.83854 | 30.29052 | 28.22236 | 25.30223 |
| | 5.0325 | 33.26317 | 31.87450 | 30.32096 | 28.24796 | 25.32231 |
| | 5.035 | 33.30397 | 31.90978 | 30.35209 | 28.27288 | 25.3417 |
| | 5.0375 | 33.34476 | 31.94574 | 30.38253 | 28.29849 | 25.36178 |
| | 5.04 | 33.38825 | 31.98171 | 30.41367 | 28.32409 | 25.38117 |
| | 5.0425 | 33.42774 | 32.01698 | 30.44411 | 28.3497 | 25.40125 |
| | 5.045 | 33.46923 | 32.05295 | 30.47524 | 28.37531 | 25.42064 |
| | 5.0475 | 33.51072 | 32.08960 | 30.50637 | 28.40091 | 25.44072 |
| | 5.05 | 33.55221 | 32.12557 | 30.5375 | 28.42652 | 25.4608 |
| | 5.0252 | 33.59439 | 32.16154 | 30.56795 | 28.45213 | 25.48019 |
| | 5.055 | 33.63588 | 32.19819 | 30.59908 | 28.47774 | 25.50027 |
| | 5.0575 | 33.67806 | 32.23418 | 30.63021 | 28.50334 | 25.52035 |
| | 5.06 | 33.72024 | 32.27082 | 30.66203 | 28.52895 | 25.53974 |
| | 5.0625 | 33.76242 | 32.30678 | 30.69317 | 28.55456 | 25.55982 |
| | 5.065 | 33.8046 | 32.34344 | 30.7243 | 28.58086 | 25.5799 |
| | 5.0675 | 33.8474 | 32.38010 | 30.75543 | 28.60647 | 25.59998 |
| | 5.07 | 33.88965 | 32.41675 | 30.78726 | 28.63207 | 25.62006 |
| | 5.0725 | 33.93252 | 32.45410 | 30.81839 | 28.65837 | 25.63945 |
| | 5.075 | 33.97539 | 32.49076 | 30.85022 | 28.68398 | 25.65953 |
| | 5.0775 | 34.01826 | 32.52742 | 30.88204 | 28.71028 | 25.67961 |
| | 5.08 | 34.06113 | 32.56476 | 30.91317 | 28.73589 | 25.69969 |
| | 5.0825 | 34.10469 | 32.60211 | 30.945 | 28.76219 | 25.71977 |
| | 5.085 | 34.14825 | 32.63877 | 30.97682 | 28.7878 | 25.73986 |
| | 5.0875 | 34.19113 | 32.67612 | 31.00865 | 28.8141 | 25.75994 |
| | 5.09 | 34.23469 | 32.71347 | 31.04047 | 28.8404 | 25.78002 |
| | 5.0925 | 34.27894 | 32.75151 | 31.0723 | 28.866 | 25.8001 |
| | 5.095 | 34.3225 | 32.78886 | 31.10412 | 28.8923 | 25.82018 |
| | 5.0975 | 34.36676 | 32.82621 | 31.13595 | 28.9186 | 25.84026 |
| | 5.1 | 34.41032 | 32.86425 | 31.16846 | 28.9449 | 25.86035 |
| | 5.1025 | 34.45457 | 32.90160 | 31.20029 | 28.9712 | 25.88043 |
| | 5.105 | 34.49883 | 32.93964 | 31.2328 | 28.9975 | 25.90051 |
| | 5.1075 | 34.54377 | 32.9768 | 31.26463 | 29.02638 | 25.92059 |
| | 5.11 | 34.58802 | 33.01572 | 31.29715 | 29.0501 | 25.94067 |
| | 5.1125 | 34.63297 | 33.05376 | 31.32966 | 29.07641 | 25.96145 |
| | 5.115 | 34.67791 | 33.09180 | 31.36218 | 29.10271 | 25.98153 |
| | 5.1175 | 34.72286 | 33.13053 | 31.39401 | 29.12901 | 26.00161 |
| | 5.12 | 34.7678 | 33.6857 | 31.42652 | 29.15531 | 26.02169 |
| | 5.1225 | 34.81344 | 33.20730 | 31.45904 | 29.1823 | 26.04178 |
| | 5.125 | 34.85838 | 33.24603 | 31.49225 | 29.2085 | 26.06255 |
| | 5.1275 | 34.90402 | 33.28476 | 31.52476 | 29.2349 | 26.08263 |
| | 5.13 | 34.94965 | 33.32350 | 31.55728 | 29.26189 | 26.10272 |
| | 5.1325 | 34.99598 | 33.36223 | 31.5898 | 29.28819 | 26.12349 |
| | 5.135 | 35.04162 | 33.40096 | 31.62301 | 29.31519 | 26.14357 |
| | 5.1375 | 35.08794 | 33.44038 | 31.65552 | 29.34149 | 26.16365 |
| | 5.14 | 35.13427 | 33.47912 | 31.68873 | 29.36848 | 26.18443 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 5.1425 | 35.1806 | 33.51854 | 31.72194 | 29.39478 | 26.20451 |
| 5.145 | 35.22692 | 33.55796 | 31.75515 | 29.42177 | 26.22529 |
| 5.1475 | 35.27394 | 33.59738 | 31.78767 | 29.44877 | 26.24537 |
| 5.15 | 35.32027 | 33.63681 | 31.82088 | 29.47576 | 26.26614 |
| 5.1525 | 35.36729 | 33.67623 | 31.85409 | 29.50206 | 26.28623 |
| 5.155 | 35.415 | 33.71566 | 31.88798 | 29.52905 | 26.307 |
| 5.1575 | 35.46201 | 33.75577 | 31.92119 | 29.55605 | 26.32709 |
| 5.16 | 35.50972 | 33.79519 | 31.9544 | 29.58304 | 26.34786 |
| 5.1625 | 35.55743 | 33.83531 | 31.9883 | 29.61003 | 26.36863 |
| 5.165 | 35.60514 | 33.87542 | 32.02151 | 29.63703 | 26.38872 |
| 5.1675 | 35.65285 | 33.91554 | 32.5541 | 29.66402 | 26.40949 |
| 5.17 | 35.70125 | 33.95565 | 32.08862 | 29.6917 | 26.42958 |
| 5.1725 | 35.74896 | 33.99646 | 32.12252 | 29.7187 | 26.45035 |
| 5.175 | 35.79736 | 34.03657 | 32.15642 | 29.74569 | 26.47113 |
| 5.1775 | 35.84645 | 34.07738 | 32.19032 | 29.77269 | 26.4919 |
| 5.18 | 35.89485 | 34.11818 | 32.22422 | 29.80037 | 26.51199 |
| 5.1825 | 35.94394 | 34.15899 | 32.25813 | 29.82736 | 26.53278 |
| 5.185 | 35.99303 | 34.19980 | 32.29203 | 29.35505 | 26.55354 |
| 5.1875 | 36.04212 | 34.24060 | 32.32593 | 29.88204 | 26.57431 |
| 5.19 | 36.0919 | 34.28141 | 32.36052 | 29.90973 | 26.59509 |
| 5.1925 | 36.141 | 34.32291 | 32.39442 | 29.93672 | 26.61517 |
| 5.195 | 36.19078 | 34.36371 | 32.42901 | 29.96441 | 26.63595 |
| 5.1975 | 36.24056 | 34.40521 | 32.46292 | 29.99209 | 26.65673 |
| 5.2 | 36.29103 | 34.44671 | 32.49751 | 30.01909 | 26.6775 |
| 5.2025 | 36.34151 | 34.48821 | 32.5321 | 30.04677 | 26.69828 |
| 5.205 | 36.39198 | 34.53039 | 32.56569 | 30.07445 | 26.71905 |
| 5.2075 | 36.44245 | 34.57189 | 32.60128 | 30.10215 | 26.73983 |
| 5.21 | 36.49293 | 34.61408 | 32.63588 | 30.12983 | 26.76061 |
| 5.2125 | 36.54409 | 34.65627 | 32.67047 | 30.15752 | 26.78138 |
| 5.215 | 36.59525 | 34.69777 | 32.70506 | 30.1852 | 26.80216 |
| 5.2175 | 36.64711 | 34.74065 | 32.74035 | 30.21289 | 26.32294 |
| 5.22 | 36.69827 | 34.78284 | 32.77494 | 30.24058 | 26.8444 |
| 5.2225 | 36.75013 | 34.82503 | 32.81022 | 30.26895 | 26.86518 |
| 5.225 | 36.80198 | 34.86791 | 32.84482 | 30.29664 | 26.88596 |
| 5.2275 | 36.85453 | 34.91010 | 32.8801 | 30.32433 | 26.90673 |
| 5.23 | 36.90639 | 34.95298 | 32.91539 | 30.3527 | 26.92751 |
| 5.2325 | 36.95893 | 34.99586 | 32.95067 | 30.38039 | 26.94898 |
| 5.235 | 37.01148 | 35.03943 | 32.98596 | 30.40808 | 26.96975 |
| 5.2375 | 37.06472 | 35.08231 | 33.02124 | 30.43645 | 26.99053 |
| 5.24 | 37.11795 | 35.12588 | 33.05722 | 30.46414 | 27.01131 |
| 5.2425 | 37.17119 | 35.16876 | 33.0925 | 30.49252 | 27.03278 |
| 5.245 | 37.22512 | 35.21233 | 33.12779 | 30.5209 | 27.05355 |
| 5.2475 | 37.27835 | 35.25591 | 33.16376 | 30.54928 | 27.07433 |
| 5.25 | 37.33228 | 35.30017 | 33.19974 | 30.57696 | 27.0958 |
| 5.2525 | 37.3869 | 35.34374 | 33.23502 | 30.60534 | 27.11658 |
| 5.255 | 37.44083 | 35.38800 | 33.271 | 30.63372 | 27.13805 |
| 5.2575 | 37.49545 | 35.43157 | 33.30698 | 30.6621 | 27.15883 |
| 5.26 | 37.55076 | 35.47584 | 33.34295 | 30.69048 | 27.18029 |
| 5.2625 | 37.60538 | 35.52079 | 33.37893 | 30.71886 | 27.20107 |
| 5.265 | 37.66069 | 35.56505 | 33.4156 | 30.74724 | 27.22254 |
| 5.2675 | 37.71669 | 35.60932 | 33.45157 | 30.77561 | 27.24332 |
| 5.27 | 37.772 | 35.65427 | 33.48824 | 30.80458 | 27.26479 |
| 5.2725 | 37.828 | 35.69923 | 33.52422 | 30.83306 | 27.28557 |
| 5.275 | 37.884 | 35.74418 | 33.56089 | 30.86144 | 27.30704 |
| 5.2775 | 37.94069 | 35.78914 | 33.59756 | 30.89051 | 27.32851 |
| 5.28 | 37.99738 | 35.83478 | 33.63422 | 30.91889 | 27.34928 |
| 5.2825 | 38.05408 | 35.87974 | 33.67089 | 30.94727 | 27.37075 |
| 5.285 | 38.11146 | 35.92538 | 33.70756 | 30.97634 | 27.39222 |
| 5.2875 | 38.16884 | 35.97103 | 33.74423 | 31.00541 | 27.41369 |
| 5.29 | 38.22622 | 36.01667 | 33.7809 | 31.03379 | 27.43447 |
| 5.2925 | 38.2843 | 36.06301 | 33.81826 | 31.06286 | 27.45594 |
| 5.295 | 38.34237 | 36.10866 | 33.85493 | 31.09193 | 27.47741 |
| 5.2975 | 38.40114 | 36.15499 | 33.89229 | 31.12101 | 27.49888 |
| 5.3 | 38.4599 | 36.20133 | 33.92965 | 31.14939 | 27.52035 |
| 5.3025 | 38.51867 | 36.24767 | 33.96701 | 31.17846 | 27.54182 |
| 5.305 | 38.57812 | 36.29469 | 34.00437 | 31.20753 | 27.56329 |
| 5.3075 | 38.63758 | 36.34103 | 34.04173 | 31.2366 | 27.58476 |
| 5.31 | 38.69703 | 36.38806 | 34.07909 | 31.26567 | 27.60623 |
| 5.3125 | 38.75718 | 36.43509 | 34.11645 | 31.29543 | 27.6277 |
| 5.315 | 38.81732 | 36.48281 | 34.1545 | 31.32451 | 27.64917 |
| 5.3175 | 38.87816 | 36.52983 | 34.19255 | 31.35358 | 27.87065 |
| 5.32 | 38.939 | 36.57755 | 34.22991 | 31.38255 | 27.69212 |
| 5.3225 | 38.99984 | 36.62527 | 34.26796 | 31.41241 | 27.71359 |
| 5.325 | 39.06136 | 36.67299 | 34.30601 | 31.44149 | 27.73506 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 5.3275 | 39.12289 | 36.72071 | 34.34407 | 31.47125 | 27.75653 |
| 5.33 | 39.18511 | 36.76843 | 34.38212 | 31.50032 | 27.778 |
| 5.3325 | 39.24733 | 36.81684 | 34.42017 | 31.53008 | 27.79947 |
| 5.335 | 39.30955 | 36.86525 | 34.45891 | 31.55985 | 27.82163 |
| 5.3375 | 39.37246 | 36.91366 | 34.49696 | 31.58892 | 27.84311 |
| 5.34 | 39.43606 | 36.96277 | 34.53571 | 31.61868 | 27.86458 |
| 5.3425 | 39.49966 | 37.01118 | 34.57445 | 31.64845 | 27.88605 |
| 5.345 | 39.56326 | 37.06028 | 34.61319 | 31.67821 | 27.90821 |
| 5.3475 | 39.62755 | 37.10938 | 34.65194 | 31.70798 | 27.92968 |
| 5.35 | 39.69184 | 37.15917 | 34.69068 | 31.73774 | 27.95116 |
| 5.3525 | 39.75683 | 37.20828 | 34.72943 | 31.7675 | 27.97332 |
| 5.355 | 39.82181 | 37.25807 | 34.76817 | 31.79727 | 27.99479 |
| 5.3575 | 39.88748 | 37.30786 | 34.8076 | 31.82772 | 28.01695 |
| 5.36 | 39.95315 | 37.35765 | 34.84635 | 31.85749 | 28.03843 |
| 5.3625 | 40.01952 | 37.40814 | 34.88578 | 31.88725 | 28.06059 |
| 5.365 | 40.08588 | 37.45862 | 34.92522 | 31.91771 | 28.08206 |
| 5.3675 | 40.15294 | 37.50911 | 34.96465 | 31.94747 | 28.10423 |
| 5.37 | 40.21999 | 37.55959 | 35.00409 | 31.97793 | 28.1257 |
| 5.3725 | 40.28774 | 37.61008 | 35.04353 | 32.00769 | 28.14786 |
| 5.375 | 40.35617 | 37.66125 | 35.08365 | 32.03815 | 28.16934 |
| 5.3775 | 40.42461 | 37.71243 | 35.12309 | 32.06861 | 28.1915 |
| 5.38 | 40.49304 | 37.76360 | 35.16321 | 32.09837 | 28.21366 |
| 5.3825 | 40.56217 | 37.81547 | 35.20334 | 32.12883 | 28.23514 |
| 5.385 | 40.63199 | 37.86734 | 35.24347 | 32.15928 | 28.2573 |
| 5.3875 | 40.70181 | 37.91920 | 35.28359 | 32.18974 | 28.27946 |
| 5.39 | 40.77232 | 37.97107 | 35.32372 | 32.2202 | 28.30163 |
| 5.3925 | 40.84282 | 38.02363 | 35.36385 | 32.25065 | 28.3231 |
| 5.395 | 40.91402 | 38.07549 | 35.40467 | 32.28111 | 28.34527 |
| 5.3975 | 40.98522 | 38.12874 | 35.4448 | 32.31157 | 28.36743 |
| 5.4 | 41.0578 | 38.18130 | 35.48561 | 32.34272 | 28.3896 |
| 5.4025 | 41.12969 | 38.23455 | 35.52643 | 32.37317 | 28.41176 |
| 5.405 | 41.20296 | 38.28780 | 35.56725 | 32.40432 | 28.43392 |
| 5.4075 | 41.27624 | 38.34105 | 35.60807 | 32.43478 | 28.45609 |
| 5.41 | 41.3502 | 38.39430 | 35.64889 | 32.46593 | 28.47825 |
| 5.4125 | 41.42416 | 38.44824 | 35.6904 | 32.49639 | 28.50042 |
| 5.415 | 41.49881 | 38.50218 | 35.73122 | 32.52753 | 28.52258 |
| 5.4175 | 41.57416 | 38.55681 | 35.77273 | 32.55868 | 28.54475 |
| 5.42 | 41.6495 | 38.61075 | 35.81424 | 32.58914 | 28.56691 |
| 5.4225 | 41.72623 | 38.66538 | 35.85575 | 32.62029 | 28.58908 |
| 5.425 | 41.80226 | 38.72070 | 35.89726 | 32.65144 | 28.61125 |
| 5.4275 | 41.87968 | 38.77533 | 35.93877 | 32.68259 | 28.63341 |
| 5.43 | 41.95709 | 38.83065 | 35.98097 | 32.71374 | 28.65627 |
| 5.4325 | 42.03589 | 38.88598 | 36.02248 | 32.74489 | 28.67843 |
| 5.435 | 42.114 | 38.94199 | 36.06468 | 32.77673 | 28.7006 |
| 5.4375 | 42.19349 | 38.99800 | 36.10688 | 32.80788 | 28.72277 |
| 5.44 | 42.27366 | 39.05402 | 36.14909 | 32.83903 | 28.74562 |
| 5.4425 | 42.35384 | 39.11003 | 36.19129 | 32.87087 | 28.76779 |
| 5.445 | 42.43471 | 39.16673 | 36.23349 | 32.90202 | 28.78995 |
| 5.4475 | 42.51627 | 39.22344 | 36.27638 | 32.93386 | 28.81281 |
| 5.45 | 42.59852 | 39.28014 | 36.31859 | 32.96501 | 28.83498 |
| 5.4525 | 42.68077 | 39.33754 | 36.36148 | 32.99685 | 28.85715 |
| 5.455 | 42.76441 | 39.39493 | 36.40437 | 33.02869 | 28.88 |
| 5.4575 | 42.84804 | 39.45302 | 36.44727 | 33.05984 | 28.90217 |
| 5.46 | 42.93236 | 39.51111 | 36.49016 | 33.09168 | 28.92503 |
| 5.4625 | 43.01807 | 39.56919 | 36.53375 | 33.12352 | 28.94719 |
| 5.465 | 43.10377 | 39.62728 | 36.57664 | 33.15537 | 28.97005 |
| 5.4675 | 43.19017 | 39.68606 | 36.62022 | 33.18721 | 28.99291 |
| 5.47 | 43.27725 | 39.74484 | 36.66381 | 33.21974 | 29.01508 |
| 5.4725 | 43.36503 | 39.80430 | 36.70739 | 33.25158 | 29.03793 |
| 5.475 | 43.45418 | 39.86377 | 36.75098 | 33.28342 | 29.06079 |
| 5.4775 | 43.54334 | 39.92324 | 36.79457 | 33.31527 | 29.08296 |
| 5.48 | 43.63319 | 39.98271 | 36.83884 | 33.3478 | 29.10582 |
| 5.4825 | 43.72373 | 40.04287 | 36.88312 | 33.37964 | 29.12868 |
| 5.485 | 43.81565 | 40.10372 | 36.9267 | 33.41218 | 29.15154 |
| 5.4875 | 43.90826 | 40.16457 | 36.97098 | 33.44471 | 29.1737 |
| 5.49 | 44.00087 | 40.22542 | 37.01595 | 33.47655 | 29.19656 |
| 5.4925 | 44.09486 | 40.28627 | 37.06023 | 33.50909 | 29.21942 |
| 5.495 | 44.18955 | 40.34782 | 37.10519 | 33.54162 | 29.24228 |
| 5.4975 | 44.28561 | 40.41005 | 37.14947 | 33.57415 | 29.26514 |
| 5.5 | 44.38167 | 40.47159 | 37.19444 | 33.60669 | 29.288 |
| 5.5025 | 44.47912 | 40.53451 | 37.23941 | 33.63922 | 29.31086 |
| 5.505 | 44.57794 | 40.59675 | 37.28438 | 33.67176 | 29.33372 |
| 5.5075 | 44.67677 | 40.65967 | 37.33003 | 33.70498 | 29.35658 |
| 5.51 | 44.77698 | 40.72260 | 37.375 | 33.73752 | 29.37944 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 5.5125 | 44.87857 | 40.78621 | 37.42066 | 33.77005 | 29.40229 |
| 5.515 | 44.98016 | 40.85052 | 37.46632 | 33.80328 | 29.42515 |
| 5.5175 | 45.08382 | 40.91413 | 37.51198 | 33.83581 | 29.44801 |
| 5.52 | 45.18817 | 40.97844 | 37.55833 | 33.86904 | 28.47087 |
| 5.5225 | 45.29321 | 41.04343 | 37.60399 | 33.90226 | 29.49442 |
| 5.525 | 45.39963 | 41.10843 | 37.65034 | 33.9348 | 29.51729 |
| 5.5275 | 45.50744 | 41.17343 | 37.69601 | 33.96803 | 29.54015 |
| 5.53 | 45.61593 | 41.23912 | 37.74305 | 34.00125 | 29.56301 |
| 5.5325 | 45.72581 | 41.30549 | 37.7894 | 34.03448 | 29.58656 |
| 5.535 | 45.83706 | 41.37187 | 37.83575 | 34.06771 | 29.60942 |
| 5.5375 | 45.9497 | 41.43825 | 37.88279 | 34.10093 | 29.63297 |
| 5.54 | 46.06303 | 41.50532 | 37.92984 | 34.13485 | 29.65583 |
| 5.5425 | 46.17843 | 41.57239 | 37.97688 | 34.16808 | 29.67869 |
| 5.545 | 46.29452 | 41.64015 | 38.02392 | 34.20131 | 29.70224 |
| 5.5475 | 46.412 | 41.70791 | 38.07096 | 34.23522 | 29.7251 |
| 5.55 | 46.53154 | 41.77637 | 38.1187 | 34.26845 | 29.74865 |
| 5.5525 | 46.65246 | 41.84551 | 38.16574 | 34.30237 | 29.77152 |
| 5.555 | 46.77477 | 41.91465 | 38.21348 | 34.33629 | 29.79507 |
| 5.5575 | 46.89846 | 41.98379 | 38.2619 | 34.36952 | 29.31862 |
| 5.56 | 47.02422 | 42.05363 | 38.30964 | 34.40343 | 29.84148 |
| 5.5625 | 47.15136 | 42.12346 | 38.35806 | 34.43735 | 29.86503 |
| 5.565 | 47.28057 | 42.19399 | 38.4058 | 34.47127 | 29.88859 |
| 5.5675 | 47.41116 | 42.26520 | 38.45422 | 34.50519 | 29.91145 |
| 5.57 | 47.54382 | 42.33642 | 38.50265 | 34.5398 | 29.935 |
| 5.5725 | 47.67856 | 42.40832 | 38.55177 | 34.57372 | 29.95855 |
| 5.575 | 47.81537 | 42.48023 | 38.60019 | 34.60764 | 29.98211 |
| 5.5775 | 47.95425 | 42.55283 | 38.64931 | 34.64225 | 30.00497 |
| 5.58 | 48.0952 | 42.62542 | 38.69843 | 34.67617 | 30.02852 |
| 5.5825 | 48.23822 | 42.69940 | 38.74823 | 34.71078 | 30.05207 |
| 5.585 | 48.384 | 42.77269 | 38.79735 | 34.74539 | 30.07563 |
| 5.5875 | 48.53186 | 42.84667 | 38.84716 | 34.77931 | 30.09918 |
| 5.59 | 48.68247 | 42.92134 | 38.89697 | 34.81392 | 30.12273 |
| 5.5925 | 48.83585 | 42.99670 | 38.94678 | 34.84853 | 30.14629 |
| 5.595 | 48.99199 | 43.07206 | 38.99659 | 34.88315 | 30.16984 |
| 5.5975 | 49.1509 | 43.14811 | 39.04709 | 34.91776 | 30.19339 |
| 5.6 | 49.31325 | 43.22417 | 39.09758 | 34.95237 | 30.21695 |
| 5.6025 | 49.47837 | 43.30160 | 39.14809 | 34.98767 | 30.2405 |
| 5.605 | 49.64694 | 43.37903 | 39.19859 | 35.02228 | 30.26475 |
| 5.6075 | 49.31985 | 43.45647 | 39.24909 | 35.05639 | 30.2883 |
| 5.61 | 49.99513 | 43.53459 | 39.30028 | 35.0922 | 30.31186 |
| 5.6125 | 50.17544 | 43.61341 | 39.35147 | 35.1275 | 30.33541 |
| 5.615 | 50.3592 | 43.69291 | 39.40266 | 35.16211 | 30.35965 |
| 5.6175 | 50.54779 | 43.77242 | 39.45454 | 35.19742 | 30.38321 |
| 5.62 | 50.74053 | 43.85331 | 39.50574 | 35.23272 | 30.40676 |
| 5.6225 | 50.93879 | 43.93351 | 39.55762 | 35.26802 | 30.43101 |
| 5.625 | 51.14188 | 44.01508 | 39.6095 | 35.30333 | 30.45456 |
| 5.6275 | 51.35119 | 44.09735 | 39.66208 | 35.33863 | 30.47881 |
| 5.63 | 51.56602 | 44.17982 | 39.71396 | 35.37394 | 30.50237 |
| 5.6325 | 51.78776 | 44.26258 | 39.76653 | 35.40993 | 30.52661 |
| 5.635 | 52.01571 | 44.34624 | 39.81911 | 35.44523 | 30.55017 |
| 5.6375 | 52.25194 | 44.43058 | 39.87237 | 35.48123 | 30.57441 |
| 5.64 | 52.49646 | 44.51492 | 39.92495 | 35.51653 | 30.59797 |
| 5.6425 | 52.74995 | 44.60064 | 39.97822 | 35.55253 | 30.62221 |
| 5.645 | 53.01312 | 44.68637 | 40.03217 | 35.58852 | 30.64577 |
| 5.6475 | 53.28653 | 44.77278 | 40.08544 | 35.62452 | 30.67002 |
| 5.65 | 53.57258 | 44.85989 | 40.13939 | 35.66052 | 30.69426 |
| 5.6525 | 53.87233 | 44.94769 | 40.19335 | 35.69651 | 30.71851 |
| 5.655 | 54.18658 | 45.03617 | 40.24731 | 35.73251 | 30.74207 |
| 5.6575 | 54.5181 | 45.12535 | 40.30127 | 35.7685 | 30.76631 |
| 5.66 | 54.86963 | 45.21522 | 40.35592 | 35.8045 | 30.79056 |
| 5.6625 | 55.24395 | 45.30578 | 40.41056 | 35.84119 | 30.81481 |
| 5.665 | 55.64519 | 45.39634 | 40.4659 | 35.87719 | 30.83905 |
| 5.6675 | 98.754 | 45.48828 | 40.52055 | 35.91387 | 30.8633 |
| 5.67 | 99.03042 | 45.58091 | 40.57589 | 35.95056 | 30.88755 |
| 5.6725 | 99.29992 | 45.67424 | 40.63123 | 35.98725 | 30.9118 |
| 5.675 | 99.54873 | 45.76825 | 40.68726 | 36.02325 | 30.93604 |
| 5.6775 | 99.79062 | 45.86296 | 40.7426 | 36.05993 | 30.96029 |
| 5.68 | 100.0256 | 45.95904 | 40.79863 | 36.09731 | 30.98454 |
| 5.6825 | 100.2468 | 46.05513 | 40.85536 | 36.134 | 31.00879 |
| 5.685 | 100.4542 | 46.15260 | 40.91139 | 36.17069 | 31.03304 |
| 5.6875 | 100.6616 | 46.25076 | 40.96811 | 36.20738 | 31.05728 |
| 5.69 | 100.8552 | 46.34960 | 41.02483 | 36.24476 | 31.08222 |
| 5.6925 | 101.0487 | 46.44914 | 41.08225 | 36.28145 | 31.10647 |
| 5.695 | 101.2285 | 46.54938 | 41.13966 | 36.31883 | 31.13072 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 5.6975 | 101.4083 | 46.65099 | 41.19707 | 36.35621 | 31.15565 |
| 5.7 | 101.5812 | 46.75329 | 41.25449 | 36.39359 | 31.17991 |
| 5.7025 | 101.7471 | 46.85698 | 41.31259 | 36.43097 | 31.20416 |
| 5.705 | 101.9131 | 46.96135 | 41.3707 | 36.46835 | 31.2291 |
| 5.7075 | 102.0722 | 47.06642 | 41.4288 | 36.50573 | 31.25334 |
| 5.71 | 102.2243 | 47.17287 | 41.4876 | 36.54311 | 31.27828 |
| 5.7125 | 102.3765 | 47.28001 | 41.5464 | 36.58118 | 31.30253 |
| 5.715 | 102.5287 | 47.38784 | 41.60519 | 36.61856 | 31.32747 |
| 5.7175 | 102.667 | 47.49774 | 41.66468 | 36.65664 | 31.35172 |
| 5.72 | 102.8123 | 47.60764 | 41.72417 | 36.69471 | 31.37666 |
| 5.7225 | 102.9506 | 47.71961 | 41.78366 | 36.73209 | 31.4016 |
| 5.725 | 103.0821 | 47.83228 | 41.84384 | 36.77016 | 31.42585 |
| 5.7275 | 103.2136 | 47.94632 | 41.90402 | 36.80323 | 31.45079 |
| 5.73 | 103.345 | 48.06106 | 41.96489 | 36.84631 | 31.47574 |
| 5.7325 | 103.4696 | 48.17718 | 42.02507 | 36.88507 | 31.50068 |
| 5.735 | 103.5941 | 48.29537 | 42.08594 | 36.92314 | 31.52493 |
| 5.7375 | 103.7187 | 48.41425 | 42.1475 | 36.96122 | 31.54987 |
| 5.74 | 103.8363 | 48.53382 | 42.20906 | 36.99998 | 31.57481 |
| 5.7425 | 103.954 | 48.65547 | 42.27062 | 37.03875 | 31.59975 |
| 5.745 | 104.0716 | 48.77849 | 42.33218 | 37.07682 | 31.62469 |
| 5.7475 | 104.1824 | 48.90290 | 42.39443 | 37.11558 | 31.64963 |
| 5.75 | 104.3001 | 49.02869 | 42.45669 | 37.15435 | 31.67457 |
| 5.7525 | 104.4039 | 49.15655 | 42.51963 | 37.19311 | 31.69952 |
| 5.755 | 104.5147 | 49.28510 | 42.58258 | 37.23257 | 31.72446 |
| 5.7575 | 104.6185 | 49.41572 | 42.64552 | 37.27133 | 31.7494 |
| 5.76 | 104.7293 | 49.54773 | 42.70916 | 37.3101 | 31.77434 |
| 5.7625 | 104.8331 | 49.68181 | 42.77279 | 37.34956 | 31.79997 |
| 5.765 | 104.9301 | 49.81727 | 42.83712 | 37.38832 | 31.82492 |
| 5.7675 | 105.0339 | 49.95480 | 42.90144 | 37.42778 | 31.84986 |
| 5.77 | 105.1309 | 50.09440 | 42.96577 | 37.46724 | 31.8748 |
| 5.7725 | 105.2278 | 50.23538 | 43.03079 | 37.50669 | 31.90043 |
| 5.775 | 105.3247 | 50.37913 | 43.09581 | 37.54615 | 31.92538 |
| 5.7775 | 105.4217 | 50.52426 | 43.16152 | 37.58561 | 31.95032 |
| 5.78 | 105.5117 | 50.67146 | 43.22723 | 37.62575 | 31.97595 |
| 5.7825 | 105.6087 | 50.82142 | 43.29293 | 37.66521 | 32.0009 |
| 5.785 | 105.6987 | 50.97346 | 43.35934 | 37.70536 | 32.02653 |
| 5.7875 | 105.7888 | 51.12756 | 43.42574 | 37.74482 | 32.05147 |
| 5.79 | 105.8788 | 51.28443 | 43.9283 | 37.78497 | 32.07711 |
| 5.7925 | 105.9689 | 51.44337 | 43.55992 | 37.82512 | 32.10274 |
| 5.795 | 106.052 | 51.60577 | 43.6277 | 37.86527 | 32.12769 |
| 5.7975 | 106.1421 | 51.77024 | 43.69548 | 37.90542 | 32.15332 |
| 5.8 | 106.2252 | 51.93816 | 43.76327 | 37.94556 | 32.17895 |
| 5.8025 | 106.3084 | 52.10815 | 43.83174 | 37.9864 | 32.2039 |
| 5.805 | 106.3915 | 52.28228 | 43.90091 | 38.02655 | 32.22953 |
| 5.8075 | 106.4746 | 52.45918 | 43.96938 | 38.0674 | 32.25517 |
| 5.81 | 106.5578 | 52.63953 | 44.03924 | 38.10824 | 32.2808 |
| 5.8125 | 106.634 | 52.82334 | 44.10909 | 38.14839 | 32.30644 |
| 5.815 | 106.7172 | 53.01060 | 44.17895 | 38.18923 | 32.33207 |
| 5.8175 | 106.7934 | 53.20200 | 44.2495 | 38.23076 | 32.35702 |
| 5.82 | 106.8766 | 53.39755 | 44.32005 | 38.2716 | 32.38265 |
| 5.8225 | 106.9528 | 53.59654 | 44.39128 | 38.31244 | 32.40898 |
| 5.825 | 107.0291 | 53.80107 | 44.46252 | 38.35398 | 32.43462 |
| 5.8275 | 107.1053 | 54.00974 | 44.53445 | 38.39482 | 32.46025 |
| 5.83 | 107.1815 | 54.22393 | 44.60638 | 38.43635 | 32.48589 |
| 5.8325 | 107.2509 | 54.44296 | 44.679 | 38.47788 | 32.51152 |
| 5.835 | 107.3271 | 54.66751 | 44.75232 | 38.51942 | 32.53716 |
| 5.8375 | 107.3965 | 54.89828 | 44.82563 | 38.56095 | 32.5628 |
| 5.84 | 107.4727 | 55.13457 | 44.89894 | 38.60248 | 32.58912 |
| 5.8425 | 107.542 | 55.37846 | 44.97295 | 38.64471 | 32.61476 |
| 5.845 | 107.6114 | 55.62856 | 45.04764 | 38.68624 | 32.6404 |
| 5.8475 | 107.6807 | 55.88696 | 45.12233 | 38.72847 | 32.66672 |
| 5.85 | 107.757 | 56.15363 | 45.19772 | 38.77 | 32.69236 |
| 5.8525 | 107.8263 | 56.42860 | 45.27311 | 38.81223 | 32.71869 |
| 5.855 | 107.8888 | 56.71255 | 45.34918 | 38.85445 | 32.74432 |
| 5.8575 | 107.9581 | 57.00754 | 45.42526 | 38.89668 | 32.77065 |
| 5.86 | 108.0274 | 57.31289 | 45.50203 | 38.93959 | 32.79629 |
| 5.8625 | 108.0968 | 57.63067 | 45.57949 | 38.98182 | 32.82262 |
| 5.865 | 108.1592 | 57.96158 | 45.65695 | 39.02474 | 32.84825 |
| 5.8675 | 108.2286 | 58.30698 | 45.7351 | 39.06696 | 32.87458 |
| 5.87 | 108.291 | 58.66827 | 45.81394 | 39.10988 | 32.90091 |
| 5.8725 | 108.3534 | 59.04683 | 45.89278 | 39.1528 | 32.92724 |
| 5.875 | 108.4228 | 59.44541 | 45.97231 | 39.19572 | 32.95288 |
| 5.8775 | 108.4852 | 59.88540 | 46.05185 | 39.23932 | 32.97921 |
| 5.88 | 108.5477 | 60.31094 | 46.13207 | 39.28224 | 33.00554 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 5.8825 | 108.6101 | 60.78479 | 46.21299 | 39.32516 | 33.03186 |
| 5.885 | 108.6726 | 61.29179 | 46.2939 | 39.36877 | 33.05819 |
| 5.8875 | 108.735 | 61.83608 | 46.37551 | 39.41238 | 33.08452 |
| 5.89 | 108.7974 | 62.42526 | 46.4578 | 39.45599 | 33.11085 |
| 5.8925 | 108.853 | 63.06830 | 46.54079 | 39.4996 | 33.13718 |
| 5.895 | 108.9154 | 63.77556 | 46.62378 | 39.54321 | 33.16351 |
| 5.8975 | 108.9779 | 64.56362 | 46.70746 | 39.58682 | 33.18984 |
| 5.9 | 109.0334 | 65.45180 | 46.79183 | 39.63112 | 33.21617 |
| 5.9025 | 109.0958 | 66.47188 | 46.8762 | 39.67542 | 33.24319 |
| 5.905 | 109.1514 | 67.66460 | 46.96126 | 39.71903 | 33.26952 |
| 5.9075 | 109.2138 | 69.09418 | 47.04702 | 39.76333 | 33.29585 |
| 5.91 | 109.2694 | 70.83450 | 47.13346 | 39.80763 | 33.32287 |
| 5.9125 | 109.3249 | 72.96152 | 47.2199 | 39.85263 | 33.3492 |
| 5.915 | 109.3804 | 75.43383 | 47.30773 | 39.89693 | 33.37653 |
| 5.9175 | 109.4429 | 77.95449 | 47.39556 | 39.94192 | 33.40256 |
| 5.92 | 109.4984 | 80.22657 | 47.48407 | 39.98622 | 33.42889 |
| 5.9225 | 109.554 | 82.13267 | 47.57259 | 40.03122 | 33.45591 |
| 5.925 | 109.6095 | 83.70042 | 47.66249 | 40.07621 | 33.48224 |
| 5.9275 | 109.665 | 85.01958 | 47.75239 | 40.1212 | 33.50926 |
| 5.93 | 109.7206 | 86.13159 | 47.84367 | 40.16689 | 33.53559 |
| 5.9325 | 109.7761 | 87.09859 | 47.93495 | 40.21188 | 33.56261 |
| 5.935 | 109.8248 | 87.94129 | 48.02692 | 40.25757 | 33.58964 |
| 5.9375 | 109.8803 | 88.69423 | 48.11959 | 40.30256 | 33.61666 |
| 5.94 | 109.9358 | 89.37121 | 48.21294 | 40.34825 | 33.64299 |
| 5.9425 | 109.9845 | 89.98604 | 48.30699 | 40.39393 | 33.67001 |
| 5.945 | 110.04 | 90.54563 | 48.40172 | 40.44031 | 33.69704 |
| 5.9475 | 110.0956 | 91.06380 | 48.49646 | 40.486 | 33.72406 |
| 5.95 | 110.1442 | 91.54744 | 48.59258 | 40.53237 | 33.75108 |
| 5.9525 | 110.1997 | 91.99655 | 48.68939 | 40.57806 | 33.7781 |
| 5.955 | 110.2484 | 92.41804 | 48.7862 | 40.62444 | 33.80513 |
| 5.9575 | 110.3039 | 92.81191 | 48.88439 | 40.67081 | 33.83215 |
| 5.96 | 110.3526 | 93.18507 | 48.98328 | 40.71719 | 33.85917 |
| 5.9625 | 110.4012 | 93.53751 | 49.08285 | 40.76426 | 33.8862 |
| 5.965 | 110.4498 | 93.87614 | 49.18311 | 40.81064 | 33.91391 |
| 5.9675 | 110.5054 | 94.19406 | 49.28407 | 40.85771 | 33.94094 |
| 5.97 | 110.564 | 94.50507 | 49.38572 | 40.90478 | 33.96796 |
| 5.9726 | 110.6027 | 94.79537 | 49.48806 | 40.95185 | 33.99498 |
| 5.975 | 110.6513 | 95.07876 | 49.59178 | 40.99892 | 34.0227 |
| 5.9775 | 110.6999 | 95.34834 | 49.6955 | 41.04599 | 34.04972 |
| 5.98 | 110.7486 | 95.60411 | 49.8006 | 41.09375 | 34.07744 |
| 5.9825 | 110.7972 | 95.85989 | 49.90639 | 41.14151 | 34.10446 |
| 5.985 | 110.8458 | 96.10185 | 50.01288 | 41.18927 | 34.13218 |
| 5.9875 | 110.8945 | 96.33000 | 50.12074 | 41.23703 | 34.1592 |
| 5.99 | 110.9431 | 96.55816 | 50.2293 | 41.28479 | 34.18692 |
| 5.9925 | 110.9918 | 96.77941 | 50.33855 | 41.33258 | 34.21394 |
| 5.995 | 111.0404 | 96.99375 | 50.44849 | 41.38101 | 34.24166 |
| 5.9975 | 111.0821 | 97.20119 | 50.55981 | 41.42946 | 34.26938 |
| 6 | 111.1308 | 97.40173 | 50.67183 | 41.47722 | 34.2964 |
| 6.0025 | 111.1794 | 97.59536 | 50.78453 | 41.52637 | 34.32412 |
| 6.005 | 111.2212 | 97.78899 | 50.89861 | 41.57482 | 34.35183 |
| 6.0075 | 111.2698 | 97.96881 | 51.01408 | 41.62328 | 34.37955 |
| 6.01 | 111.3184 | 98.15553 | 51.13024 | 41.67242 | 34.40727 |
| 6.0125 | 111.3602 | 98.32845 | 51.24709 | 41.72157 | 34.43498 |
| 6.015 | 111.4088 | 98.50136 | 51.36532 | 41.77071 | 34.4627 |
| 6.0175 | 111.4506 | 98.66738 | 51.48425 | 41.81986 | 34.49042 |
| 6.02 | 111.4992 | 98.83339 | 51.60455 | 41.869 | 34.51814 |
| 6.0225 | 111.5409 | 98.99940 | 51.72624 | 41.91884 | 34.54586 |
| 6.025 | 111.5827 | 99.15160 | 51.84931 | 41.96868 | 34.57357 |
| 6.0275 | 111.6313 | 99.31071 | 51.97307 | 42.01851 | 34.60198 |
| 6.03 | 111.6731 | 99.46291 | 52.09752 | 42.06835 | 34.6297 |
| 6.0325 | 111.7148 | 99.60821 | 52.22404 | 42.11819 | 34.65741 |
| 6.035 | 111.7634 | 99.75351 | 52.35125 | 42.16872 | 34.68582 |
| 6.0375 | 111.8052 | 99.89881 | 52.48054 | 42.21855 | 34.71354 |
| 6.04 | 111.8469 | 100.03720 | 52.61052 | 42.26908 | 34.74126 |
| 6.0425 | 111.8886 | 100.17559 | 52.74188 | 42.31961 | 34.76967 |
| 6.045 | 111.9373 | 100.31399 | 52.87462 | 42.37083 | 34.79739 |
| 6.0476 | 111.979 | 100.44548 | 53.00875 | 42.42136 | 34.8258 |
| 6.05 | 112.0208 | 100.57697 | 53.14425 | 42.47258 | 34.8542 |
| 6.0525 | 112.0625 | 100.70155 | 53.28114 | 42.5238 | 34.88192 |
| 6.055 | 112.1042 | 100.83304 | 53.41941 | 42.57503 | 34.91033 |
| 6.0575 | 112.146 | 100.95763 | 53.55976 | 42.62625 | 34.93874 |
| 6.06 | 112.1877 | 101.07531 | 53.70079 | 42.67816 | 34.96715 |
| 6.0625 | 112.2295 | 101.19989 | 53.8439 | 42.73007 | 34.99487 |
| 6.065 | 112.2712 | 101.31758 | 53.98908 | 42.78129 | 35.02328 |

APPENDIX 1-continued

Standard Mass Calculation

| | Temps | | | | |
|---|---|---|---|---|---|
| | 15.1 | 17.2 | 20.1 C. | 25.1 C. | 35.1 C. |
| 6.0675 | 112.3129 | 101.43526 | 54.13564 | 42.8339 | 35.05169 |
| 6.07 | 112.3547 | 101.55294 | 54.28358 | 42.88581 | 35.0801 |
| 6.0725 | 112.3964 | 101.66371 | 54.4336 | 42.93842 | 35.10851 |
| 6.075 | 112.4313 | 101.77449 | 54.585 | 42.99033 | 35.13692 |
| 6.0775 | 112.473 | 101.88527 | 54.73847 | 43.04293 | 35.16534 |
| 6.08 | 112.5147 | 101.99605 | 54.89401 | 43.09554 | 35.19375 |
| 6.0825 | 112.5565 | 102.09992 | 55.05094 | 43.14884 | 35.22285 |
| 6.085 | 112.5982 | 102.21070 | 55.21063 | 43.20144 | 35.25126 |
| 6.0875 | 112.633 | 102.31457 | 55.3717 | 43.25474 | 35.27967 |
| 6.09 | 112.6748 | 102.41844 | 55.53484 | 43.30803 | 35.30808 |
| 6.0925 | 112.7165 | 102.52231 | 55.70006 | 43.36202 | 35.33718 |
| 6.095 | 112.7514 | 102.61928 | 55.86804 | 43.41532 | 35.3656 |
| 6.0975 | 112.7931 | 102.72316 | 56.0381 | 43.46931 | 35.3947 |
| 6.1 | 112.8279 | 102.82012 | 56.21022 | 43.5233 | 36.42311 |
| 6.1025 | 112.8697 | 102.91709 | 56.38442 | 43.67728 | 35.45221 |
| 6.105 | 112.9114 | 103.01406 | 56.56139 | 43.63127 | 35.48063 |
| 6.1075 | 112.9463 | 103.11103 | 56.74111 | 43.68595 | 35.50973 |
| 6.11 | 112.988 | 103.20110 | 56.92291 | 43.74063 | 35.53883 |
| 6.1125 | 113.0228 | 103.29807 | 57.10748 | 43.79531 | 35.56725 |
| 6.115 | 113.0646 | 103.38813 | 57.2948 | 43.84999 | 35.59635 |
| 6.1175 | 113.0994 | 103.47820 | 57.48489 | 43.90537 | 35.62545 |
| 6.12 | 113.1343 | 103.56828 | 57.67775 | 43.96074 | 35.65456 |
| 6.1225 | 113.176 | 103.65833 | 57.87337 | 44.01611 | 35.68366 |
| 6.125 | 113.2108 | 103.74148 | 58.07244 | 44.07148 | 35.71276 |
| 6.1275 | 113.2526 | 103.83155 | 58.27428 | 44.12755 | 35.74187 |
| 6.13 | 113.2874 | 103.92162 | 58.47957 | 44.18292 | 35.77097 |
| 6.1325 | 113.3222 | 104.00478 | 58.68762 | 44.23898 | 35.80008 |
| 6.135 | 113.364 | 104.08794 | 58.89982 | 44.29574 | 35.82918 |
| 6.1375 | 113.3988 | 104.17110 | 59.11479 | 44.3518 | 35.85829 |
| 6.14 | 113.4337 | 104.25426 | 59.33389 | 44.40856 | 35.88739 |
| 6.1425 | 113.4685 | 104.33742 | 59.55646 | 44.46531 | 35.91719 |
| 6.145 | 113.5102 | 104.42059 | 59.78248 | 44.52207 | 35.94629 |
| 6.1475 | 113.5451 | 104.49684 | 60.01264 | 44.57952 | 35.9754 |
| 6.15 | 113.5799 | 104.58000 | 60.24695 | 44.63627 | 36.00519 |
| 6.1525 | 113.6148 | 104.65626 | 60.48541 | 44.69372 | 36.0343 |
| 6.155 | 113.6496 | 104.73942 | 60.72801 | 44.75186 | 36.0641 |
| 6.1575 | 113.6844 | 104.81568 | 60.97475 | 44.80931 | 36.0932 |
| 6.16 | 113.7262 | 104.89194 | 61.22633 | 44.86745 | 36.123 |
| 6.1625 | 113.761 | 104.96820 | 61.48275 | 44.92559 | 36.1528 |
| 6.165 | 113.7959 | 105.04445 | 61.74332 | 44.98373 | 36.1819 |
| 6.1675 | 113.8307 | 105.12071 | 62.00872 | 45.04256 | 36.2117 |
| 6.17 | 113.8655 | 105.19006 | 62.27965 | 45.10139 | 36.2415 |
| 6.1725 | 113.9004 | 105.26632 | 62.55541 | 45.16022 | 36.27129 |
| 6.175 | 113.9352 | 105.33568 | 62.83601 | 45.21905 | 36.30109 |
| 6.1775 | 113.97 | 105.41194 | 63.12214 | 45.27857 | 36.33089 |
| 6.18 | 114.0049 | 105.48129 | 63.41449 | 45.3381 | 36.36069 |
| 6.1825 | 114.0397 | 105.55755 | 63.71167 | 45.39762 | 36.39048 |
| 6.185 | 114.0746 | 105.62690 | 64.01507 | 45.45783 | 36.42028 |
| 6.1875 | 114.1094 | 105.69626 | 64.324 | 45.51805 | 36.45008 |
| 6.19 | 114.1373 | 105.76561 | 64.63914 | 45.57826 | 36.47988 |
| 6.1925 | 114.1722 | 105.83496 | 64.95982 | 45.63848 | 36.50968 |
| 6.195 | 114.207 | 105.90432 | 65.28671 | 45.69939 | 36.54017 |
| 6.1975 | 114.2419 | 105.97367 | 65.61982 | 45.76029 | 36.56997 |
| 6.2 | 114.2767 | 106.03612 | 65.95984 | 45.8212 | 36.60046 |
| 6.2025 | 114.3115 | 106.10548 | 66.30539 | 45.88211 | 36.63026 |
| 6.205 | 114.3464 | 106.17483 | 66.65716 | 45.9437 | 36.66005 |
| 6.2075 | 114.3743 | 106.23728 | 67.01583 | 46.0053 | 36.69054 |
| 6.21 | 114.4092 | 106.30664 | 67.38004 | 46.06759 | 36.72103 |
| 6.2125 | 114.444 | 106.36909 | 67.75115 | 46.12919 | 36.75083 |
| 6.215 | 114.4788 | 106.43154 | 68.12779 | 46.19148 | 36.78132 |
| 6.2175 | 114.5068 | 106.50090 | 68.51065 | 46.25446 | 36.81182 |
| 6.22 | 114.5416 | 106.56335 | 68.89904 | 46.31675 | 36.84231 |
| 6.2225 | 114.5764 | 106.62680 | 69.29019 | 46.37973 | 36.87211 |
| 6.225 | 114.6044 | 106.68825 | 69.69101 | 46.44341 | 36.9026 |
| 6.2275 | 114.6392 | 106.75070 | 70.09875 | 46.50639 | 36.93309 |
| 6.23 | 114.6741 | 106.81315 | 70.50649 | 46.57006 | 36.96358 |
| 6.2325 | 114.702 | 106.87560 | 70.92113 | 46.63374 | 36.99407 |
| 6.235 | 114.7368 | 106.93605 | 71.34269 | 46.6981 | 37.02456 |
| 6.2375 | 114.7717 | 106.99360 | 71.76425 | 46.76247 | 37.05575 |
| 6.24 | 114.7996 | 107.05605 | 72.18581 | 46.82683 | 37.08624 |
| 6.2425 | 114.8345 | 107.11850 | 72.62119 | 46.8912 | 37.11673 |
| 6.245 | 114.8624 | 107.17405 | 73.04966 | 46.95826 | 37.14722 |
| 6.2475 | 114.8972 | 107.23650 | 73.48505 | 47.022 | 37.17841 |
| 6.25 | 114.9252 | 107.29205 | 73.92043 | 47.08706 | 37.2089 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 6.2525 | 114.96 | 107.35450 | 74.35582 | 47.15281 | 37.24008 |
| 6.255 | 114.9879 | 107.41005 | 74.79121 | 47.21856 | 37.27057 |
| 6.2575 | 115.0228 | 107.46559 | 75.22661 | 47.285 | 37.30176 |
| 6.26 | 115.0507 | 107.52805 | 75.662 | 47.35075 | 37.33225 |
| 6.2625 | 115.0856 | 107.58359 | 76.0974 | 47.41788 | 37.36344 |
| 6.265 | 115.1135 | 107.63914 | 76.52589 | 47.48432 | 37.39462 |
| 6.2675 | 115.1483 | 107.69469 | 76.96129 | 47.55145 | 37.4258 |
| 6.27 | 115.1763 | 107.75024 | 77.38979 | 47.61928 | 37.4563 |
| 6.2725 | 115.2111 | 107.80576 | 77.81828 | 47.68641 | 37.48748 |
| 6.275 | 115.2391 | 107.86133 | 78.23988 | 47.75423 | 37.51867 |
| 6.2775 | 115.267 | 107.91688 | 78.65456 | 47.82275 | 37.54985 |
| 6.28 | 115.3018 | 107.97243 | 79.06925 | 47.89057 | 37.58104 |
| 6.2825 | 115.3298 | 108.02798 | 79.48394 | 47.95909 | 37.61222 |
| 6.285 | 115.3577 | 108.08353 | 79.39173 | 48.0283 | 37.6441 |
| 6.2875 | 115.3926 | 108.13217 | 80.29261 | 48.0975 | 37.67528 |
| 6.29 | 115.4205 | 108.18772 | 80.68658 | 48.16671 | 37.70647 |
| 6.2925 | 115.4484 | 108.24327 | 81.08056 | 48.23661 | 37.73766 |
| 6.295 | 115.4833 | 108.29191 | 81.46762 | 48.30651 | 37.76953 |
| 6.2975 | 115.5112 | 108.34746 | 81.84779 | 48.37641 | 37.80072 |
| 6.3 | 115.6391 | 108.39610 | 82.22104 | 48.447 | 37.8326 |
| 6.3025 | 115.5671 | 108.45165 | 82.58739 | 48.51759 | 37.86378 |
| 6.305 | 115.6019 | 108.50029 | 82.94684 | 48.58887 | 37.89566 |
| 6.3075 | 115.6299 | 108.55585 | 83.30628 | 48.66015 | 37.92685 |
| 6.31 | 115.6578 | 108.60449 | 83.65882 | 48.73144 | 37.95872 |
| 6.3125 | 115.6857 | 108.65313 | 84.00446 | 48.80341 | 37.9906 |
| 6.315 | 115.7206 | 108.70868 | 84.34318 | 48.87539 | 38.02248 |
| 6.3175 | 115.7485 | 108.75733 | 84.675 | 48.94736 | 38.05436 |
| 6.32 | 115.7765 | 108.80597 | 84.99992 | 49.02003 | 38.08624 |
| 6.3225 | 115.8044 | 108.85462 | 85.31792 | 49.09338 | 38.11811 |
| 6.325 | 115.8323 | 108.90326 | 85.63593 | 49.16674 | 38.14999 |
| 6.3275 | 115.8603 | 108.95881 | 85.94012 | 49.2401 | 38.18187 |
| 6.33 | 115.8951 | 109.00746 | 86.24432 | 49.31415 | 38.21375 |
| 6.3325 | 115.9231 | 109.05610 | 86.54161 | 49.3882 | 38.24563 |
| 6.335 | 115.951 | 109.10475 | 86.83199 | 49.46225 | 38.27751 |
| 6.3375 | 115.9789 | 109.15339 | 87.11546 | 49.53699 | 38.31008 |
| 6.34 | 116.0069 | 109.20204 | 87.39894 | 49.61242 | 38.34196 |
| 6.3425 | 116.0348 | 109.24378 | 87.6755 | 49.68786 | 38.37384 |
| 6.345 | 116.0627 | 109.29242 | 87.94517 | 49.76329 | 38.40641 |
| 6.3475 | 116.0907 | 109.34107 | 88.20792 | 49.83941 | 38.43829 |
| 6.35 | 116.1186 | 109.38971 | 88.47068 | 49.91553 | 38.47086 |
| 6.3525 | 116.1466 | 109.43836 | 88.72652 | 49.99235 | 38.50343 |
| 6.355 | 116.1745 | 109.48010 | 88.97547 | 50.06917 | 38.53531 |
| 6.3575 | 116.2024 | 109.52875 | 89.2175 | 50.14667 | 38.56788 |
| 6.38 | 116.2304 | 109.57739 | 89.45953 | 50.22418 | 38.60045 |
| 6.3625 | 116.2583 | 109.61913 | 89.69466 | 50.30169 | 38.63302 |
| 6.365 | 116.2863 | 109.66778 | 89.92979 | 50.37989 | 38.6656 |
| 6.3675 | 116.3142 | 109.71643 | 90.15801 | 50.45878 | 38.69817 |
| 6.37 | 116.3421 | 109.75817 | 90.37932 | 50.63767 | 38.73074 |
| 6.3725 | 116.3701 | 109.80681 | 90.60064 | 50.61656 | 38.76331 |
| 6.375 | 116.398 | 109.84855 | 90.81505 | 50.69614 | 38.79588 |
| 6.3775 | 116.426 | 109.89720 | 91.02945 | 50.77642 | 38.82915 |
| 6.38 | 116.4539 | 109.93894 | 91.23696 | 50.85669 | 38.86172 |
| 6.3825 | 116.4818 | 109.98068 | 91.43755 | 50.93697 | 38.89429 |
| 6.385 | 116.5098 | 110.02933 | 91.64505 | 51.01793 | 38.92756 |
| 6.3875 | 116.5377 | 110.07107 | 91.83874 | 51.09959 | 38.96013 |
| 6.39 | 116.5657 | 110.11281 | 92.03242 | 51.18125 | 38.99339 |
| 6.3925 | 116.5867 | 110.16146 | 92.22611 | 51.2636 | 39.02597 |
| 6.395 | 116.6146 | 110.20320 | 92.41289 | 51.34595 | 39.05923 |
| 6.3975 | 116.6426 | 110.24494 | 92.59967 | 51.4283 | 39.0925 |
| 6.4 | 116.6705 | 110.28668 | 92.77955 | 51.51134 | 39.12507 |
| 6.4025 | 116.6984 | 110.32843 | 92.95942 | 51.59507 | 39.15834 |
| 6.405 | 116.7264 | 110.37708 | 93.13929 | 51.6788 | 39.1916 |
| 6.4075 | 116.7474 | 110.41882 | 93.31226 | 51.76323 | 39.22487 |
| 6.41 | 116.7754 | 110.46056 | 93.47832 | 51.84834 | 39.25813 |
| 6.4125 | 116.8033 | 110.50230 | 93.65129 | 51.93277 | 39.2914 |
| 6.415 | 116.8312 | 110.54404 | 93.81735 | 52.01857 | 39.32466 |
| 6.4175 | 116.8592 | 110.58579 | 93.9765 | 52.10438 | 39.35862 |
| 6.42 | 116.8802 | 110.62753 | 94.14256 | 52.19088 | 39.39188 |
| 6.4225 | 116.9082 | 110.66927 | 94.29481 | 52.27738 | 39.42515 |
| 6.425 | 116.9361 | 110.71101 | 94.45396 | 52.36388 | 39.45911 |
| 6.4275 | 116.964. | 110.75276 | 94.60621 | 52.45176 | 39.49237 |
| 6.43 | 116.9851 | 110.79450 | 94.75845 | 52.53964 | 39.52633 |
| 6.4325 | 117.013 | 110.83624 | 94.9107 | 52.62753 | 39.5596 |
| 6.435 | 117.0409 | 110.87108 | 95.05604 | 52.7161 | 39.59356 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 6.4375 | 117.062 | 110.91282 | 95.20138 | 52.80536 | 39.62751 |
| 6.44 | 117.0899 | 110.95457 | 95.34672 | 52.89532 | 39.66078 |
| 6.4425 | 117.1179 | 110.99631 | 95.48515 | 52.98528 | 39.69474 |
| 6.445 | 117.1458 | 111.03805 | 95.6305 | 53.07524 | 39.7287 |
| 6.4475 | 117.1668 | 111.07289 | 95.76893 | 53.16589 | 39.76266 |
| 6.45 | 117.1948 | 111.11483 | 95.90046 | 53.25723 | 39.79662 |
| 6.4525 | 117.2227 | 111.15638 | 96.03889 | 53.34926 | 39.83058 |
| 6.455 | 117.2438 | 111.19121 | 96.17042 | 53.44129 | 39.86453 |
| 6.4575 | 117.2717 | 111.23296 | 96.30194 | 53.53401 | 39.89849 |
| 6.46 | 117.2927 | 111.27470 | 96.43347 | 53.62674 | 39.93314 |
| 6.4625 | 117.3207 | 111.30954 | 96.55809 | 53.72015 | 39.9671 |
| 6.465 | 117.3486 | 111.35129 | 96.68271 | 53.81426 | 40.00106 |
| 6.4675 | 117.3696 | 111.38612 | 96.80733 | 53.90837 | 40.03571 |
| 6.47 | 117.3976 | 111.42787 | 96.93195 | 54.00317 | 40.06967 |
| 6.4725 | 117.4186 | 111.46270 | 97.05657 | 54.09866 | 40.10433 |
| 6.475 | 117.4466 | 111.50445 | 97.17428 | 54.19484 | 40.13898 |
| 6.4775 | 117.4745 | 111.53929 | 97.292 | 54.29102 | 40.17294 |
| 6.48 | 117.4955 | 111.58103 | 97.40971 | 54.38789 | 40.20759 |
| 6.4825 | 117.5235 | 111.61587 | 97.52742 | 54.48477 | 40.24224 |
| 6.485 | 117.5445 | 111.65762 | 97.64514 | 54.58233 | 40.27689 |
| 6.4875 | 117.5725 | 111.69245 | 97.75594 | 54.68059 | 40.31154 |
| 6.49 | 117.6935 | 111.72729 | 97.87366 | 54.77954 | 40.3462 |
| 6.4925 | 117.6214 | 111.76904 | 97.98447 | 54.87918 | 40.38085 |
| 6.495 | 117.6425 | 111.80388 | 98.09527 | 54.97882 | 40.4155 |
| 6.4975 | 117.6704 | 111.83871 | 98.19917 | 55.07915 | 40.45085 |
| 6.5 | 117.6914 | 111.88046 | 98.30998 | 55.17948 | 40.4855 |
| 6.5025 | 117.7194 | 111.91530 | 98.41388 | 55.2812 | 40.52015 |
| 6.505 | 117.7404 | 111.95014 | 98.52469 | 55.38291 | 40.5555 |
| 6.5075 | 117.7684 | 111.99189 | 98.62859 | 55.48532 | 40.59015 |
| 6.51 | 117.7894 | 112.02672 | 98.73249 | 55.58773 | 40.62549 |
| 6.5125 | 117.8173 | 112.06156 | 98.83639 | 55.69151 | 40.66015 |
| 6.515 | 117.8384 | 112.09640 | 98.93338 | 55.7953 | 40.69549 |
| 6.5175 | 117.8663 | 112.13124 | 99.03728 | 55.89979 | 40.73084 |
| 6.52 | 117.8874 | 112.17299 | 99.13428 | 56.00496 | 40.76618 |
| 6.5225 | 117.9153 | 112.20783 | 99.23818 | 56.11082 | 40.80153 |
| 6.525 | 117.9363 | 112.24267 | 99.33517 | 56.21669 | 40.83687 |
| 6.5275 | 117.9574 | 112.27751 | 99.43217 | 56.32324 | 40.87222 |
| 6.53 | 117.9853 | 112.31235 | 99.52225 | 56.43049 | 40.90756 |
| 6.5325 | 118.0063 | 112.34718 | 99.61925 | 56.53843 | 40.94291 |
| 6.535 | 118.0343 | 112.38202 | 99.71624 | 56.64706 | 40.97826 |
| 6.5375 | 118.0553 | 112.41686 | 99.80633 | 56.75569 | 41.01429 |
| 6.54 | 118.0764 | 112.45170 | 99.90333 | 56.86571 | 41.04964 |
| 6.5425 | 118.1043 | 112.48654 | 99.99341 | 56.97572 | 41.08568 |
| 6.545 | 118.1253 | 112.52138 | 100.0835 | 57.08643 | 41.12102 |
| 6.5475 | 118.1533 | 112.55622 | 100.1736 | 57.19783 | 41.15706 |
| 6.55 | 118.1743 | 112.59107 | 100.2637 | 57.30992 | 41.19241 |
| 6.5525 | 118.1954 | 112.62591 | 100.3538 | 57.42201 | 41.22845 |
| 6.555 | 118.2233 | 112.66075 | 100.4369 | 57.53548 | 41.26449 |
| 6.5575 | 118.2443 | 112.69559 | 100.527 | 57.64895 | 41.30052 |
| 6.56 | 118.2654 | 112.73043 | 100.6102 | 57.76381 | 41.33656 |
| 6.5625 | 118.2933 | 112.76527 | 100.7003 | 57.87866 | 41.3726 |
| 6.565 | 118.3144 | 112.80011 | 100.7835 | 57.99421 | 41.40864 |
| 6.5675 | 118.3354 | 112.82804 | 100.8667 | 58.11045 | 41.44468 |
| 6.57 | 118.3633 | 112.86288 | 100.9498 | 58.22738 | 41.48072 |
| 6.5725 | 118.3844 | 112.89772 | 101.033 | 58.345 | 41.51745 |
| 6.575 | 118.4054 | 112.93257 | 101.1162 | 58.46332 | 41.55349 |
| 6.5775 | 118.4264 | 112.96741 | 101.1994 | 58.58163 | 41.59022 |
| 6.58 | 118.4544 | 112.99534 | 101.2757 | 58.70133 | 41.62626 |
| 6.5825 | 118.4754 | 113.03018 | 101.3588 | 58.82172 | 41.66299 |
| 6.585 | 118.4965 | 113.06502 | 101.4351 | 58.94211 | 41.69903 |
| 6.5875 | 118.5175 | 113.09987 | 101.5183 | 59.06388 | 41.73576 |
| 6.59 | 118.5454 | 113.12780 | 101.5946 | 59.18565 | 41.7725 |
| 6.5925 | 118.5665 | 113.16264 | 101.6709 | 59.30881 | 41.80923 |
| 6.595 | 118.5875 | 113.19748 | 101.754 | 59.43196 | 41.84596 |
| 6.5975 | 118.6085 | 113.22542 | 101.8303 | 59.55581 | 41.88269 |
| 6.6 | 118.6365 | 113.26026 | 101.9066 | 59.68104 | 41.91943 |
| 6.6025 | 118.6575 | 113.29510 | 101.9829 | 59.80627 | 41.95616 |
| 6.605 | 118.8786 | 113.32303 | 102.0522 | 59.93219 | 41.99289 |
| 6.6075 | 118.6996 | 113.35788 | 102.1285 | 60.0595 | 42.03031 |
| 6.61 | 118.7206 | 113.38581 | 102.2048 | 60.1868 | 42.06705 |
| 6.6125 | 118.7486 | 113.42065 | 102.2742 | 60.3148 | 42.10447 |
| 6.615 | 118.7696 | 113.45550 | 102.3504 | 60.44349 | 42.14121 |
| 6.6175 | 118.7907 | 113.48343 | 102.4198 | 60.57356 | 42.17863 |
| 6.62 | 118.8117 | 113.51827 | 102.4961 | 60.70363 | 42.21606 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 6.6225 | 118.8327 | 113.54621 | 102.5654 | 60.8344 | 42.25279 |
| 6.625 | 118.8607 | 113.58105 | 102.6348 | 60.96654 | 42.29021 |
| 6.6275 | 118.8317 | 113.60899 | 102.7042 | 61.09869 | 42.32764 |
| 6.63 | 118.9028 | 113.64383 | 102.7805 | 61.23222 | 42.36507 |
| 6.6325 | 118.9238 | 113.67176 | 102.8498 | 61.36575 | 42.40249 |
| 6.635 | 118.9448 | 113.70661 | 102.9192 | 61.49998 | 42.43992 |
| 6.6375 | 118.9659 | 113.73454 | 102.9817 | 61.63558 | 42.47803 |
| 6.64 | 118.9869 | 113.76939 | 103.051 | 61.77188 | 42.51546 |
| 6.6425 | 119.0148 | 113.79732 | 103.1204 | 61.90818 | 42.55289 |
| 6.645 | 119.0359 | 113.82528 | 103.1898 | 62.04586 | 42.591 |
| 6.6475 | 119.0569 | 113.86010 | 103.2522 | 62.18354 | 42.62843 |
| 6.65 | 119.078 | 113.88804 | 103.3216 | 62.3226 | 42.66655 |
| 6.6525 | 119.099 | 113.92288 | 103.3841 | 62.46236 | 42.70467 |
| 6.655 | 119.12 | 113.95081 | 103.4534 | 62.60211 | 42.74279 |
| 6.6575 | 119.1411 | 113.97875 | 103.5159 | 62.74325 | 42.78021 |
| 6.66 | 119.1621 | 114.01360 | 103.5853 | 62.88508 | 42.81833 |
| 6.6625 | 119.1831 | 114.04153 | 103.6477 | 63.02761 | 42.85645 |
| 6.665 | 119.2042 | 114.06947 | 103.7102 | 63.17082 | 42.89526 |
| 6.6675 | 119.2252 | 114.10431 | 103.7727 | 63.31473 | 42.93338 |
| 6.67 | 119.2463 | 114.13225 | 103.842 | 63.45933 | 42.9715 |
| 6.6725 | 119.2742 | 114.16018 | 103.9045 | 63.60462 | 43.00962 |
| 6.675 | 119.2952 | 114.19503 | 103.967 | 63.7506 | 43.04843 |
| 6.6775 | 119.3163 | 114.22296 | 104.0294 | 63.89727 | 43.08655 |
| 6.68 | 119.3373 | 114.25090 | 104.085 | 64.04464 | 43.12536 |
| 6.6825 | 119.3584 | 114.27883 | 104.1474 | 64.19269 | 43.16348 |
| 6.685 | 119.3794 | 114.31368 | 104.2099 | 64.34144 | 43.20229 |
| 6.6875 | 119.4004 | 114.34162 | 104.2724 | 64.49088 | 43.2411 |
| 6.69 | 119.4215 | 114.36955 | 104.3348 | 64.64102 | 43.27992 |
| 6.6925 | 119.4425 | 114.39749 | 104.3904 | 64.79184 | 43.31873 |
| 6.695 | 119.4635 | 114.42543 | 104.4529 | 64.94336 | 43.35754 |
| 6.6975 | 119.4846 | 114.46027 | 104.5084 | 65.09557 | 43.39635 |
| 6.7 | 119.5056 | 114.48821 | 104.5709 | 65.24847 | 43.43517 |
| 6.7025 | 119.5267 | 114.51615 | 104.6264 | 65.40206 | 43.47467 |
| 6.705 | 119.5477 | 114.54408 | 104.6889 | 65.55634 | 43.51348 |
| 6.7075 | 119.5687 | 114.57202 | 104.7445 | 65.71132 | 43.55299 |
| 6.71 | 119.5898 | 114.59996 | 104.8069 | 65.86698 | 43.5918 |
| 6.7125 | 119.6108 | 114.62789 | 104.8625 | 66.02265 | 43.6313 |
| 6.715 | 119.6319 | 114.65583 | 104.918 | 66.1797 | 43.67012 |
| 6.7175 | 119.6529 | 114.69068 | 104.9736 | 66.33745 | 43.70962 |
| 6.72 | 119.667 | 114.71861 | 105.0291 | 66.49519 | 43.74913 |
| 6.7225 | 119.6881 | 114.74655 | 105.0847 | 66.65363 | 43.78863 |
| 6.725 | 119.7091 | 114.77449 | 105.1472 | 66.81345 | 43.82814 |
| 6.7275 | 119.7301 | 114.80243 | 105.2027 | 66.97327 | 43.86764 |
| 6.73 | 119.7512 | 114.83036 | 105.2583 | 67.13378 | 43.90784 |
| 6.7325 | 119.7722 | 114.85830 | 105.3138 | 67.29429 | 43.94735 |
| 6.735 | 119.7932 | 114.88624 | 105.3625 | 67.45618 | 43.98685 |
| 6.7375 | 119.8143 | 114.91418 | 105.4181 | 67.61808 | 44.02705 |
| 6.74 | 119.8353 | 114.94211 | 105.4736 | 67.78067 | 44.06656 |
| 6.7425 | 119.8564 | 114.97005 | 105.5292 | 67.94395 | 44.10676 |
| 6.745 | 119.8774 | 114.99799 | 105.5847 | 68.10792 | 44.14695 |
| 6.7475 | 119.8984 | 115.02593 | 105.6334 | 68.27189 | 44.18715 |
| 6.75 | 119.9195 | 115.05387 | 105.6889 | 68.43656 | 44.22666 |
| 6.7525 | 119.9336 | 115.08180 | 105.7445 | 68.60191 | 44.26686 |
| 6.755 | 119.9546 | 115.10974 | 105.7931 | 68.76796 | 44.30775 |
| 6.7575 | 119.9757 | 115.13768 | 105.8487 | 68.93401 | 44.34795 |
| 6.76 | 119.9967 | 115.16562 | 105.8974 | 69.10075 | 44.38815 |
| 6.7625 | 120.0178 | 115.13665 | 105.9529 | 69.2668 | 44.42834 |
| 6.765 | 120.0388 | 115.21458 | 106.0016 | 69.43286 | 44.46924 |
| 6.7675 | 120.0598 | 115.24252 | 106.0571 | 69.60582 | 44.50944 |
| 6.77 | 120.074 | 115.27046 | 106.1058 | 69.77187 | 44.55033 |
| 6.7725 | 120.095 | 115.29840 | 106.1544 | 69.93793 | 44.59122 |
| 6.775 | 120.1161 | 115.32634 | 106.21 | 70.11089 | 44.63142 |
| 6.7775 | 120.1371 | 115.35428 | 106.2586 | 70.27695 | 44.67231 |
| 6.78 | 120.1581 | 115.38222 | 106.3073 | 70.44992 | 44.7132 |
| 6.7825 | 120.1792 | 115.40325 | 106.3559 | 70.61598 | 44.75409 |
| 6.785 | 120.1933 | 115.43118 | 106.4046 | 70.78895 | 44.79499 |
| 6.7875 | 120.2143 | 115.45912 | 106.4602 | 70.95501 | 44.83657 |
| 6.79 | 120.2354 | 115.48706 | 106.5088 | 71.12798 | 44.87746 |
| 6.7925 | 120.2564 | 115.51500 | 106.5575 | 71.30095 | 44.91835 |
| 6.795 | 120.2775 | 115.53603 | 106.6061 | 71.47392 | 44.95994 |
| 6.7975 | 120.2985 | 115.56397 | 106.6548 | 71.63999 | 45.00083 |
| 6.8 | 120.3128 | 115.59191 | 106.7034 | 71.81296 | 45.04242 |
| 6.8025 | 120.3337 | 115.61985 | 106.7521 | 71.98594 | 45.084 |
| 6.805 | 120.3547 | 115.64779 | 106.8007 | 72.15891 | 45.12559 |

APPENDIX 1-continued

Standard Mass Calculation

| | Temps | | | | |
|---|---|---|---|---|---|
| | 15.1 | 17.2 | 20.1 C. | 25.1 C. | 35.1 C. |
| 6.8075 | 120.3757 | 115.66882 | 106.8494 | 72.33189 | 45.16717 |
| 6.81 | 120.3899 | 115.69676 | 106.8911 | 72.50487 | 45.20876 |
| 6.8125 | 120.4109 | 115.72470 | 106.9398 | 72.67785 | 45.25034 |
| 6.815 | 120.432 | 115.75264 | 106.9884 | 72.84392 | 45.29193 |
| 6.8175 | 120.453 | 115.77367 | 107.0371 | 73.0169 | 45.33351 |
| 6.82 | 120.474 | 115.80161 | 107.0857 | 73.18988 | 45.37579 |
| 6.8225 | 120.4882 | 115.82955 | 107.1275 | 73.36286 | 45.41738 |
| 6.825 | 120.5092 | 115.85058 | 107.1761 | 73.53584 | 45.45965 |
| 6.8275 | 120.5302 | 115.87852 | 107.2248 | 73.70883 | 45.50193 |
| 6.83 | 120.5513 | 115.90646 | 107.2665 | 73.88181 | 45.54352 |
| 6.8325 | 120.5654 | 115.92749 | 107.3152 | 74.0548 | 45.5858 |
| 6.835 | 120.5865 | 115.95543 | 107.3669 | 74.22779 | 45.62807 |
| 6.8375 | 120.6075 | 115.98337 | 107.4056 | 74.40077 | 45.67035 |
| 6.84 | 120.6216 | 116.00440 | 107.4542 | 74.57376 | 45.71263 |
| 6.8425 | 120.6427 | 116.03234 | 107.496 | 74.74675 | 45.7556 |
| 6.845 | 120.6637 | 116.06028 | 107.5377 | 74.91283 | 45.79788 |
| 6.8475 | 120.6847 | 116.08131 | 107.5864 | 75.08582 | 45.84085 |
| 6.85 | 120.6989 | 116.10925 | 107.6281 | 75.25881 | 45.88313 |
| 6.8525 | 120.7199 | 116.13028 | 107.6768 | 75.4318 | 46.9261 |
| 6.855 | 120.741 | 116.15822 | 107.7185 | 75.6048 | 46.96838 |
| 6.8575 | 120.7551 | 116.18616 | 107.7603 | 75.77088 | 46.01135 |
| 6.88 | 120.7761 | 116.20719 | 107.8089 | 75.94388 | 46.05432 |
| 6.8625 | 120.7972 | 116.23514 | 107.8607 | 76.11687 | 46.0973 |
| 6.865 | 120.8182 | 116.25617 | 107.8924 | 76.28296 | 46.14027 |
| 6.8675 | 120.8323 | 116.28411 | 107.9411 | 76.45595 | 46.18393 |
| 6.87 | 120.8534 | 116.30514 | 107.9828 | 76.62204 | 46.2269 |
| 6.8725 | 120.8744 | 116.33308 | 108.0246 | 76.79504 | 46.26988 |
| 6.875 | 120.8886 | 116.36102 | 108.0663 | 76.96113 | 46.31364 |
| 6.8775 | 120.9096 | 116.38205 | 108.1081 | 77.13413 | 46.35651 |
| 6.88 | 120.9306 | 116.40999 | 108.1498 | 77.30022 | 46.40018 |
| 6.8825 | 120.9448 | 116.43102 | 108.1915 | 77.46631 | 46.44384 |
| 6.885 | 120.9658 | 116.45897 | 108.2402 | 77.6324 | 46.4875 |
| 6.8875 | 120.9868 | 116.48000 | 108.282 | 77.8054 | 46.53117 |
| 6.89 | 121.001 | 116.50794 | 108.3237 | 77.9715 | 46.57483 |
| 6.8925 | 121.022 | 116.52897 | 108.3654 | 78.13759 | 46.6135 |
| 6.895 | 121.0361 | 116.55691 | 108.4072 | 78.30368 | 46.66286 |
| 6.8975 | 121.0572 | 116.57794 | 108.4489 | 78.46978 | 46.70652 |
| 6.9 | 121.0782 | 116.60589 | 108.4838 | 78.62896 | 46.75019 |
| 6.9025 | 121.0924 | 116.62692 | 108.5255 | 78.79506 | 46.79455 |
| 6.905 | 121.1134 | 116.64795 | 108.5673 | 78.96116 | 46.8389 |
| 6.9075 | 121.1344 | 116.67589 | 108.609 | 79.12034 | 46.88326 |
| 6.91 | 121.1486 | 116.69692 | 108.6508 | 79.28644 | 46.92762 |
| 6.9125 | 121.1696 | 116.72486 | 108.6925 | 79.44563 | 46.97198 |
| 6.915 | 121.1837 | 116.74589 | 108.7343 | 79.61173 | 47.01633 |
| 6.9175 | 121.2048 | 116.77384 | 108.7691 | 79.77092 | 47.06069 |
| 6.92 | 121.2258 | 116.79487 | 108.8108 | 79.93011 | 47.10505 |
| 6.9225 | 121.24 | 116.81590 | 108.8526 | 80.09621 | 47.1501 |
| 6.925 | 121.261 | 116.84384 | 108.8943 | 80.2554 | 47.19446 |
| 6.9275 | 121.2751 | 116.86488 | 108.9292 | 80.41459 | 47.23951 |
| 6.93 | 121.2962 | 116.89282 | 108.9709 | 80.56687 | 47.28456 |
| 6.9325 | 121.3172 | 116.91385 | 109.0127 | 80.72607 | 47.32892 |
| 6.935 | 121.3313 | 116.93488 | 109.0475 | 80.88526 | 47.37397 |
| 6.9375 | 121.3524 | 116.96283 | 109.0893 | 81.04445 | 47.41902 |
| 6.94 | 121.3665 | 116.98386 | 109.131 | 81.19674 | 47.46477 |
| 6.9425 | 121.3876 | 117.00489 | 109.1659 | 81.34902 | 47.50982 |
| 6.945 | 121.4017 | 117.03283 | 109.2076 | 81.50822 | 47.55487 |
| 6.9475 | 121.4227 | 117.05386 | 109.2424 | 81.6605 | 47.60061 |
| 6.95 | 121.4369 | 117.07490 | 109.2842 | 81.81279 | 47.64567 |
| 6.9525 | 121.4579 | 117.10284 | 109.319 | 81.96508 | 47.69141 |
| 6.955 | 121.4789 | 117.12387 | 109.3608 | 82.11736 | 47.73715 |
| 6.9575 | 121.4931 | 117.14490 | 109.3956 | 82.26965 | 47.7829 |
| 6.96 | 121.5141 | 117.17285 | 109.4374 | 82.42194 | 47.82864 |
| 6.9625 | 121.5283 | 117.19388 | 109.4722 | 82.56732 | 47.87439 |
| 6.965 | 121.5493 | 117.21491 | 109.514 | 82.71961 | 47.92013 |
| 6.9675 | 121.5634 | 117.23595 | 109.5488 | 82.86498 | 47.96588 |
| 6.97 | 121.5845 | 117.26389 | 109.5905 | 83.01728 | 48.01231 |
| 6.9725 | 121.5986 | 117.28492 | 109.6254 | 83.16266 | 48.05806 |
| 6.975 | 121.6196 | 117.30595 | 109.6602 | 83.30804 | 48.1045 |
| 6.9775 | 121.6338 | 117.33390 | 109.702 | 83.45342 | 48.15093 |
| 6.98 | 121.6548 | 117.35493 | 109.7368 | 83.5988 | 48.19737 |
| 6.9826 | 121.6689 | 117.37596 | 109.7717 | 83.74418 | 48.24381 |
| 6.985 | 121.69 | 117.39700 | 109.8065 | 83.88956 | 48.29025 |
| 6.9875 | 121.7041 | 117.41803 | 109.8482 | 84.02803 | 48.33669 |
| 6.99 | 121.7252 | 117.44597 | 109.8831 | 84.17342 | 48.38312 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 6.9925 | 121.7393 | 117.46701 | 109.9179 | 84.31189 | 48.43025 |
| 6.995 | 121.7603 | 117.48804 | 109.9528 | 84.45036 | 48.47669 |
| 6.9975 | 121.7745 | 117.50907 | 109.9945 | 84.59575 | 48.52382 |
| 7 | 121.7955 | 117.53702 | 110.0294 | 84.73422 | 48.57095 |
| 7.0025 | 121.8096 | 117.55805 | 110.0642 | 84.8727 | 48.61739 |
| 7.005 | 121.8307 | 117.57908 | 110.099 | 85.01117 | 48.66452 |
| 7.0075 | 121.8448 | 117.60012 | 110.1339 | 85.14273 | 48.71165 |
| 7.01 | 121.8659 | 117.62115 | 110.1687 | 85.28121 | 48.75948 |
| 7.0125 | 121.88 | 117.64910 | 110.2105 | 85.41969 | 48.80661 |
| 7.015 | 121.901 | 117.67013 | 110.2453 | 85.55125 | 48.85374 |
| 7.0175 | 121.9152 | 117.69116 | 110.2802 | 85.68282 | 48.90156 |
| 7.02 | 121.9382 | 117.71220 | 110.315 | 85.8213 | 48.94939 |
| 7.0225 | 121.9503 | 117.73323 | 110.3498 | 85.95286 | 48.99652 |
| 7.025 | 121.9645 | 117.75426 | 110.3847 | 86.08443 | 49.04434 |
| 7.0275 | 121.9855 | 117.77530 | 110.4195 | 86.216 | 49.09217 |
| 7.03 | 121.9996 | 117.80324 | 110.4544 | 86.34065 | 49.13999 |
| 7.0325 | 122.0207 | 117.82428 | 110.4892 | 86.47222 | 49.18851 |
| 7.035 | 122.0348 | 117.84531 | 110.5241 | 86.60379 | 49.23633 |
| 7.0375 | 122.0559 | 117.86634 | 110.5589 | 86.72845 | 49.28416 |
| 7.04 | 122.07 | 117.88738 | 110.5937 | 86.86002 | 49.33267 |
| 7.0425 | 122.0841 | 117.90841 | 110.6286 | 86.98467 | 49.38119 |
| 7.045 | 122.1052 | 117.92944 | 110.6634 | 87.10933 | 49.42902 |
| 7.0475 | 122.1193 | 117.95048 | 110.6913 | 87.23399 | 49.47753 |
| 7.05 | 122.1403 | 117.97151 | 110.7262 | 87.35865 | 49.52605 |
| 7.0525 | 122.1545 | 117.99946 | 110.761 | 87.48331 | 49.57526 |
| 7.055 | 122.1755 | 118.02049 | 110.7959 | 87.60797 | 49.62378 |
| 7.0575 | 122.1896 | 118.04153 | 110.8307 | 87.72572 | 49.67229 |
| 7.06 | 122.2038 | 118.06256 | 110.8656 | 87.85038 | 49.7215 |
| 7.0625 | 122.2248 | 118.08360 | 110.8935 | 87.96813 | 49.77002 |
| 7.065 | 122.2389 | 118.10463 | 110.9283 | 88.09279 | 49.81923 |
| 7.0675 | 122.26 | 118.12566 | 110.9632 | 88.21054 | 49.86844 |
| 7.07 | 122.2741 | 118.14670 | 110.998 | 88.32829 | 49.91765 |
| 7.0725 | 122.2883 | 118.16773 | 111.0329 | 88.44604 | 49.96686 |
| 7.075 | 122.3093 | 118.18877 | 111.0608 | 88.5638 | 50.01608 |
| 7.0775 | 122.3234 | 118.20980 | 111.0956 | 88.68155 | 50.06598 |
| 7.08 | 122.3376 | 118.23084 | 111.1305 | 88.7993 | 50.11519 |
| 7.0825 | 122.3586 | 118.25187 | 111.1653 | 88.91014 | 50.16509 |
| 7.085 | 122.3727 | 118.27290 | 111.1933 | 89.02789 | 50.2143 |
| 7.0875 | 122.3938 | 118.29394 | 111.2281 | 89.13873 | 50.26421 |
| 7.09 | 122.4079 | 118.31497 | 111.263 | 89.25649 | 50.31411 |
| 7.0925 | 122.422 | 118.33601 | 111.2909 | 89.36733 | 50.36402 |
| 7.095 | 122.4431 | 118.35704 | 111.3257 | 89.47817 | 50.41392 |
| 7.0975 | 122.4572 | 118.37808 | 111.3537 | 89.58902 | 50.46452 |
| 7.1 | 122.4714 | 118.39911 | 111.3885 | 89.69986 | 50.51442 |
| 7.1025 | 122.4924 | 118.42015 | 111.4233 | 89.8107 | 50.56502 |
| 7.105 | 122.5065 | 118.44118 | 111.4513 | 89.92155 | 50.61492 |
| 7.1075 | 122.5207 | 118.46222 | 111.4861 | 90.02548 | 50.66552 |
| 7.11 | 122.5417 | 118.48325 | 111.5141 | 90.13632 | 50.71611 |
| 7.1125 | 122.5558 | 118.50429 | 111.5489 | 90.24717 | 50.76671 |
| 7.115 | 122.57 | 118.52532 | 111.5768 | 90.3511 | 50.81731 |
| 7.1175 | 122.591 | 118.54636 | 111.6117 | 90.45503 | 50.8686 |
| 7.12 | 122.6051 | 118.56739 | 111.6465 | 90.56588 | 50.9192 |
| 7.1225 | 122.6193 | 118.58843 | 111.6745 | 90.66981 | 50.97048 |
| 7.125 | 122.6403 | 118.60946 | 111.7093 | 90.77375 | 51.02108 |
| 7.1275 | 122.6544 | 118.63050 | 111.7372 | 90.87768 | 51.07237 |
| 7.13 | 122.6686 | 118.65153 | 111.7852 | 90.98162 | 51.12366 |
| 7.1325 | 122.6896 | 118.67257 | 111.8 | 91.07864 | 51.17495 |
| 7.135 | 122.7038 | 118.68669 | 111.8279 | 91.18258 | 51.22624 |
| 7.1375 | 122.7179 | 118.70773 | 111.8628 | 91.28651 | 51.27753 |
| 7.14 | 122.7389 | 118.72876 | 111.8907 | 91.38353 | 51.32952 |
| 7.1425 | 122.7531 | 118.74980 | 111.9256 | 91.48747 | 51.38081 |
| 7.145 | 122.7672 | 118.77083 | 111.9535 | 91.5845 | 51.43279 |
| 7.1475 | 122.7882 | 118.79187 | 111.9814 | 91.68152 | 51.48477 |
| 7.15 | 122.8024 | 118.81291 | 112.0163 | 91.78546 | 51.53676 |
| 7.1525 | 122.8165 | 118.83394 | 112.0442 | 91.88248 | 51.58874 |
| 7.155 | 122.8306 | 118.85498 | 112.0791 | 91.97951 | 51.64072 |
| 7.1575 | 122.8517 | 118.86910 | 112.107 | 92.07654 | 51.69271 |
| 7.16 | 122.8658 | 118.89013 | 112.1349 | 92.17356 | 51.74538 |
| 7.1625 | 122.8799 | 118.91117 | 112.1698 | 92.26367 | 51.79737 |
| 7.165 | 122.901 | 118.93221 | 112.1977 | 92.3607 | 51.85004 |
| 7.1675 | 122.9151 | 118.95324 | 112.2257 | 92.45773 | 51.90272 |
| 7.17 | 122.9293 | 118.97428 | 112.2536 | 92.54784 | 51.9554 |
| 7.1725 | 122.9434 | 118.99532 | 112.2884 | 92.64487 | 52.00807 |
| 7.175 | 122.9644 | 119.00944 | 112.3164 | 92.73499 | 52.06075 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 7.1775 | 122.9786 | 119.03047 | 112.3443 | 92.83202 | 52.11343 |
| 7.18 | 122.9927 | 119.05151 | 112.3791 | 92.92213 | 52.1668 |
| 7.1825 | 123.0068 | 119.07255 | 112.4071 | 93.01225 | 52.22017 |
| 7.185 | 123.0279 | 119.09358 | 112.435 | 93.10236 | 52.27285 |
| 7.1875 | 123.042 | 119.11462 | 112.463 | 93.19248 | 52.32622 |
| 7.19 | 123.0561 | 119.12874 | 112.4909 | 93.2826 | 52.37959 |
| 7.1925 | 123.0703 | 119.14978 | 112.5257 | 93.37271 | 52.43296 |
| 7.195 | 123.0913 | 119.17082 | 112.5537 | 93.46283 | 52.48702 |
| 7.1975 | 123.1054 | 119.19185 | 112.5816 | 93.55295 | 52.54039 |
| 7.2 | 123.1196 | 119.21289 | 112.6095 | 93.63615 | 52.59376 |
| 7.2025 | 123.1337 | 119.22701 | 112.6375 | 93.72627 | 52.64782 |
| 7.205 | 123.1548 | 119.24805 | 112.6654 | 93.80948 | 52.70188 |
| 7.2075 | 123.1689 | 119.26908 | 112.7003 | 93.8996 | 52.75595 |
| 7.21 | 123.183 | 119.29012 | 112.7282 | 93.9828 | 52.81001 |
| 7.2125 | 123.1972 | 119.31116 | 112.7561 | 94.07292 | 52.86407 |
| 7.215 | 123.2182 | 119.32528 | 112.7841 | 94.15613 | 52.91814 |
| 7.2175 | 123.2323 | 119.34632 | 112.812 | 94.23934 | 52.97289 |
| 7.22 | 123.2465 | 119.36736 | 112.8399 | 94.32254 | 53.02696 |
| 7.2225 | 123.2606 | 119.38839 | 112.8679 | 94.40575 | 53.08171 |
| 7.225 | 123.2747 | 119.40251 | 112.8958 | 94.48896 | 53.13647 |
| 7.2275 | 123.2958 | 119.42355 | 112.9237 | 94.57217 | 53.19123 |
| 7.23 | 123.3099 | 119.44459 | 112.9517 | 94.65538 | 53.24598 |
| 7.2325 | 123.324 | 119.46563 | 112.9796 | 94.73859 | 53.30074 |
| 7.235 | 123.3382 | 119.47975 | 113.0076 | 94.8218 | 53.35619 |
| 7.2375 | 123.3523 | 119.50079 | 113.0355 | 94.89809 | 53.41095 |
| 7.24 | 123.3734 | 119.52182 | 113.0634 | 94.9813 | 53.4664 |
| 7.2425 | 123.3875 | 119.54286 | 113.0914 | 95.06451 | 53.52185 |
| 7.245 | 123.4016 | 119.55698 | 113.1193 | 95.14081 | 53.57729 |
| 7.2475 | 123.4157 | 119.57802 | 113.1472 | 95.2171 | 53.63274 |
| 7.25 | 123.4299 | 119.59906 | 113.1752 | 95.30031 | 53.68819 |
| 7.2525 | 123.4509 | 119.61318 | 113.2031 | 95.37661 | 53.74365 |
| 7.255 | 123.4651 | 119.63422 | 113.231 | 95.45291 | 53.79979 |
| 7.2575 | 123.4792 | 119.65526 | 113.259 | 95.53612 | 53.85593 |
| 7.26 | 123.4933 | 119.67630 | 113.2869 | 95.61242 | 53.91138 |
| 7.2625 | 123.5075 | 119.69042 | 113.3149 | 95.68872 | 53.96752 |
| 7.265 | 123.5216 | 119.71146 | 113.3428 | 95.76502 | 54.02367 |
| 7.2675 | 123.5426 | 119.73249 | 113.3707 | 95.84132 | 54.07981 |
| 7.27 | 123.5668 | 119.74662 | 113.3987 | 95.91761 | 54.13665 |
| 7.2725 | 123.5709 | 119.76766 | 113.4266 | 95.99391 | 54.19279 |
| 7.275 | 123.585 | 119.78869 | 113.4545 | 96.07021 | 54.24963 |
| 7.2775 | 123.5992 | 119.80282 | 113.4825 | 96.1396 | 54.30646 |
| 7.28 | 123.6133 | 119.82386 | 113.5035 | 96.2159 | 54.36261 |
| 7.2825 | 123.6343 | 119.84489 | 113.5314 | 96.2922 | 54.41944 |
| 7.285 | 123.6485 | 119.85902 | 113.5594 | 96.36159 | 54.47697 |
| 7.2875 | 123.6626 | 119.88005 | 113.5873 | 96.43789 | 54.53381 |
| 7.29 | 123.6767 | 119.90109 | 113.6153 | 96.50728 | 54.59064 |
| 7.2925 | 123.6909 | 119.91522 | 113.6432 | 96.58358 | 54.64817 |
| 7.295 | 123.705 | 119.93626 | 113.6642 | 96.65297 | 54.7057 |
| 7.2975 | 123.7261 | 119.95729 | 113.6922 | 96.72235 | 54.76254 |
| 7.3 | 123.7402 | 119.97142 | 113.7201 | 96.79866 | 54.82007 |
| 7.3025 | 123.7543 | 119.99246 | 113.748 | 96.86804 | 54.87829 |
| 7.305 | 123.7685 | 120.00658 | 113.776 | 96.93743 | 54.93582 |
| 7.3075 | 123.7826 | 120.02762 | 113.797 | 97.00682 | 54.99335 |
| 7.31 | 123.7967 | 120.04866 | 113.8249 | 97.07621 | 55.05158 |
| 7.3125 | 123.8109 | 120.06278 | 113.8529 | 97.1456 | 55.10911 |
| 7.315 | 123.825 | 120.08382 | 113.8808 | 97.21499 | 55.16733 |
| 7.3175 | 123.846 | 120.10486 | 113.9088 | 97.28438 | 55.22555 |
| 7.32 | 123.8602 | 120.11898 | 113.9298 | 97.35377 | 55.28378 |
| 7.3225 | 123.8743 | 120.14002 | 113.9577 | 97.42316 | 55.34269 |
| 7.325 | 123.8884 | 120.15414 | 113.9857 | 97.49255 | 55.40091 |
| 7.3275 | 123.9026 | 120.17518 | 114.0067 | 97.56194 | 55.45983 |
| 7.33 | 123.9167 | 120.19622 | 114.0346 | 97.62442 | 55.51805 |
| 7.3325 | 123.9308 | 120.21035 | 114.0626 | 97.69381 | 55.57697 |
| 7.335 | 123.945 | 120.23138 | 114.0905 | 97.7632 | 55.63589 |
| 7.3375 | 123.9591 | 120.24551 | 114.1115 | 97.82568 | 55.6948 |
| 7.34 | 123.9801 | 120.26665 | 114.1395 | 97.89507 | 55.75372 |
| 7.3425 | 123.9943 | 120.28067 | 114.1674 | 97.95755 | 55.81333 |
| 7.345 | 124.0084 | 120.30171 | 114.1884 | 98.02695 | 55.87225 |
| 7.3475 | 124.0225 | 120.32275 | 114.2164 | 98.08942 | 55.93186 |
| 7.35 | 124.0367 | 120.33687 | 114.2443 | 98.1519 | 55.99147 |
| 7.3525 | 124.0508 | 120.35791 | 114.2653 | 98.2213 | 56.05108 |
| 7.355 | 124.0649 | 120.37204 | 114.2933 | 98.28377 | 56.11069 |
| 7.3575 | 124.0791 | 120.39308 | 114.3143 | 98.34625 | 56.1703 |
| 7.36 | 124.0932 | 120.40720 | 114.3422 | 98.40873 | 56.22991 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 7.3625 | 124.1073 | 120.42824 | 114.3702 | 98.47813 | 56.29021 |
| 7.365 | 124.1215 | 120.44236 | 114.3912 | 98.54061 | 56.35051 |
| 7.3675 | 124.1356 | 120.46340 | 114.4191 | 98.60309 | 56.41012 |
| 7.37 | 124.1567 | 120.47753 | 114.4402 | 98.66557 | 56.47043 |
| 7.3725 | 124.1708 | 120.49857 | 114.4681 | 98.72805 | 56.53073 |
| 7.375 | 124.1849 | 120.51961 | 114.496 | 98.79053 | 56.59173 |
| 7.3775 | 124.1991 | 120.53373 | 114.5171 | 98.85301 | 56.65203 |
| 7.38 | 124.2132 | 120.55477 | 114.545 | 98.90858 | 56.71303 |
| 7.3825 | 124.2273 | 120.56890 | 114.566 | 98.97106 | 56.77333 |
| 7.385 | 124.2415 | 120.58994 | 114.594 | 99.03354 | 56.83433 |
| 7.3875 | 124.2556 | 120.60406 | 114.615 | 99.09602 | 56.89532 |
| 7.39 | 124.2697 | 120.62510 | 114.6429 | 99.15851 | 56.95632 |
| 7.3925 | 124.2839 | 120.63922 | 114.664 | 99.21407 | 57.01732 |
| 7.395 | 124.298 | 120.66026 | 114.6919 | 99.27656 | 57.07901 |
| 7.3975 | 124.3121 | 120.67439 | 114.7129 | 99.33212 | 57.14 |
| 7.4 | 124.3262 | 120.69543 | 114.7409 | 99.39461 | 57.20169 |
| 7.4025 | 124.3404 | 120.70955 | 114.7619 | 99.45709 | 57.26338 |
| 7.405 | 124.3545 | 120.73059 | 114.7898 | 99.51266 | 57.32507 |
| 7.4075 | 124.3686 | 120.74472 | 114.8109 | 99.57514 | 57.38676 |
| 7.41 | 124.3828 | 120.76576 | 114.8388 | 99.63071 | 57.44845 |
| 7.4125 | 124.3969 | 120.77988 | 114.8598 | 99.68628 | 57.51015 |
| 7.415 | 124.411 | 120.80092 | 114.8878 | 99.74877 | 57.57253 |
| 7.4175 | 124.4321 | 120.81505 | 114.9088 | 99.80434 | 57.63491 |
| 7.42 | 124.4462 | 120.82917 | 114.9368 | 99.85991 | 57.6966 |
| 7.4225 | 124.4604 | 120.85021 | 114.9578 | 99.92239 | 57.75899 |
| 7.425 | 124.4745 | 120.86434 | 114.9857 | 99.97796 | 57.82206 |
| 7.4275 | 124.4886 | 120.88538 | 115.0067 | 100.0335 | 57.88445 |
| 7.43 | 124.5028 | 120.89950 | 115.0347 | 100.0891 | 57.94683 |
| 7.4325 | 124.5169 | 120.92054 | 115.0557 | 100.1447 | 58.00991 |
| 7.435 | 124.531 | 120.93467 | 115.0767 | 100.2002 | 58.07229 |
| 7.4375 | 124.5452 | 120.95571 | 115.1047 | 100.2558 | 58.13537 |
| 7.44 | 124.5593 | 120.96983 | 115.1257 | 100.3114 | 58.19845 |
| 7.4425 | 124.5734 | 120.99087 | 115.1537 | 100.367 | 58.26153 |
| 7.445 | 124.5876 | 121.00500 | 115.1747 | 100.4225 | 58.3246 |
| 7.4475 | 124.6017 | 121.01912 | 115.1957 | 100.4781 | 58.38837 |
| 7.45 | 124.6158 | 121.04016 | 115.2237 | 100.5337 | 58.45145 |
| 7.4525 | 124.63 | 121.05429 | 115.2447 | 100.5892 | 58.51522 |
| 7.455 | 124.6441 | 121.07533 | 115.2657 | 100.6448 | 58.57899 |
| 7.4575 | 124.6582 | 121.08945 | 115.2936 | 100.7004 | 58.64276 |
| 7.46 | 124.6724 | 121.11050 | 115.3147 | 100.749 | 58.70653 |
| 7.4625 | 124.6865 | 121.12462 | 115.3357 | 100.8046 | 58.77031 |
| 7.465 | 124.7006 | 121.13875 | 115.3636 | 100.8602 | 58.83408 |
| 7.4675 | 124.7148 | 121.15979 | 115.3847 | 100.9158 | 58.89854 |
| 7.47 | 124.7289 | 121.17391 | 115.4057 | 100.9644 | 58.963 |
| 7.4725 | 124.743 | 121.19495 | 115.4336 | 101.02 | 59.02678 |
| 7.475 | 124.7572 | 121.20908 | 115.4547 | 101.0687 | 59.09124 |
| 7.4775 | 124.7713 | 121.22320 | 115.4757 | 101.1242 | 59.15571 |
| 7.48 | 124.7854 | 121.24424 | 115.5036 | 101.1729 | 59.22086 |
| 7.4825 | 124.7996 | 121.25837 | 115.5247 | 101.2285 | 59.28533 |
| 7.485 | 124.8137 | 121.27941 | 115.5457 | 101.2771 | 59.34979 |
| 7.4875 | 124.8278 | 121.29354 | 115.5736 | 101.3327 | 59.41495 |
| 7.49 | 124.842 | 121.30766 | 115.5947 | 101.3814 | 59.48011 |
| 7.4925 | 124.8492 | 121.32870 | 115.6157 | 101.4369 | 59.54527 |
| 7.495 | 124.8633 | 121.34283 | 115.6367 | 101.4856 | 59.61043 |
| 7.4975 | 124.8775 | 121.35695 | 115.6647 | 101.5343 | 59.67558 |
| 7.5 | 124.8916 | 121.37800 | 115.6857 | 101.5898 | 59.74074 |
| 7.5025 | 124.9057 | 121.39212 | 115.7067 | 101.6385 | 59.80659 |
| 7.505 | 124.9199 | 121.40625 | 115.7278 | 101.6872 | 59.87175 |
| 7.5075 | 124.934 | 121.42729 | 115.7557 | 101.7358 | 59.9376 |
| 7.51 | 124.9481 | 121.44141 | 115.7767 | 101.7914 | 60.00346 |
| 7.5125 | 124.9623 | 121.46246 | 115.7978 | 101.8401 | 60.06931 |
| 7.515 | 124.9764 | 121.47658 | 115.8188 | 101.8887 | 60.13516 |
| 7.5175 | 124.9905 | 121.49071 | 115.8467 | 101.9374 | 60.20101 |
| 7.52 | 125.0047 | 121.51175 | 115.8678 | 101.986 | 60.26756 |
| 7.5225 | 125.0188 | 121.52587 | 115.8888 | 102.0347 | 60.33341 |
| 7.525 | 125.0329 | 121.54000 | 115.9098 | 102.0834 | 60.39996 |
| 7.5275 | 125.0471 | 121.56104 | 115.9308 | 102.132 | 60.4665 |
| 7.53 | 125.0612 | 121.57517 | 115.9588 | 102.1807 | 60.53305 |
| 7.5325 | 125.0753 | 121.58929 | 115.9798 | 102.2293 | 60.59959 |
| 7.535 | 125.0895 | 121.61033 | 116.0008 | 102.278 | 60.66614 |
| 7.5375 | 125.1036 | 121.62446 | 116.0219 | 102.3267 | 60.73338 |
| 7.54 | 125.1177 | 121.63859 | 116.0429 | 102.3753 | 60.79993 |
| 7.5425 | 125.1249 | 121.65963 | 116.0639 | 102.424 | 60.86716 |
| 7.545 | 125.1391 | 121.67375 | 116.0919 | 102.4727 | 60.9344 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 7.5475 | 125.1532 | 121.68788 | 116.1129 | 102.5213 | 61.00095 |
| 7.55 | 125.1673 | 121.70892 | 116.1339 | 102.5631 | 61.06819 |
| 7.5525 | 125.1815 | 121.72305 | 116.155 | 102.6117 | 61.13612 |
| 7.555 | 125.1956 | 121.73717 | 116.176 | 102.6604 | 61.20336 |
| 7.5575 | 125.2097 | 121.75130 | 116.197 | 102.7091 | 61.2706 |
| 7.56 | 125.2239 | 121.77234 | 116.2181 | 102.7508 | 61.33854 |
| 7.5625 | 125.238 | 121.78647 | 116.2391 | 102.7995 | 61.40647 |
| 7.565 | 125.2522 | 121.80059 | 116.267 | 102.8481 | 61.47371 |
| 7.5675 | 125.2663 | 121.82164 | 116.2881 | 102.8899 | 61.54165 |
| 7.57 | 125.2804 | 121.83576 | 116.3091 | 102.9386 | 61.60958 |
| 7.5725 | 125.2876 | 121.84989 | 116.3301 | 102.9872 | 61.67821 |
| 7.575 | 125.3018 | 121.86401 | 116.3512 | 103.029 | 61.74614 |
| 7.5775 | 125.3159 | 121.88506 | 116.3722 | 103.0776 | 61.81407 |
| 7.58 | 125.33 | 121.89918 | 116.3932 | 103.1194 | 61.8827 |
| 7.5825 | 125.3442 | 121.91331 | 116.4142 | 103.1681 | 61.95133 |
| 7.585 | 125.3583 | 121.93435 | 116.4353 | 103.2098 | 62.01996 |
| 7.5875 | 125.3724 | 121.94848 | 116.4563 | 103.2585 | 62.08858 |
| 7.59 | 125.3866 | 121.96260 | 116.4773 | 103.3002 | 62.15721 |
| 7.5925 | 125.4007 | 121.97673 | 116.5053 | 103.3489 | 62.22584 |
| 7.595 | 125.4148 | 121.99777 | 116.5263 | 103.3906 | 62.29447 |
| 7.5975 | 125.4221 | 122.01190 | 116.5473 | 103.4324 | 62.36379 |
| 7.6 | 125.4362 | 122.02602 | 116.5684 | 103.4811 | 62.43242 |
| 7.6025 | 125.4503 | 122.04015 | 116.5894 | 103.5228 | 62.50174 |
| 7.605 | 125.4645 | 122.06119 | 116.6104 | 103.5646 | 62.57106 |
| 7.6075 | 125.4786 | 122.07532 | 116.6315 | 103.6132 | 62.64038 |
| 7.61 | 125.4927 | 122.08945 | 116.6525 | 103.655 | 62.7097 |
| 7.6125 | 125.5069 | 122.10357 | 116.6735 | 103.6967 | 62.77903 |
| 7.615 | 125.521 | 122.12462 | 116.6945 | 103.7385 | 62.84835 |
| 7.6175 | 125.5351 | 122.13874 | 116.7156 | 103.7871 | 62.91836 |
| 7.62 | 125.5424 | 122.15287 | 116.7366 | 103.8289 | 62.98769 |
| 7.6225 | 125.5565 | 122.16699 | 116.7576 | 103.8707 | 63.0577 |
| 7.625 | 125.5706 | 122.18804 | 116.7787 | 103.9124 | 63.12772 |
| 7.6275 | 125.5848 | 122.20216 | 116.7997 | 103.9542 | 63.19704 |
| 7.63 | 125.5989 | 122.21629 | 116.8207 | 103.9959 | 63.26706 |
| 7.6325 | 125.613 | 122.23042 | 116.8418 | 104.0446 | 63.33777 |
| 7.635 | 125.6272 | 122.25146 | 116.8628 | 104.0863 | 63.40778 |
| 7.6375 | 125.6344 | 122.26559 | 116.8838 | 104.1281 | 63.4778 |
| 7.64 | 125.6485 | 122.27971 | 116.9049 | 104.1698 | 63.54851 |
| 7.6425 | 125.6626 | 122.29384 | 116.9259 | 104.2116 | 63.61853 |
| 7.645 | 125.6768 | 122.30797 | 116.9469 | 104.2533 | 63.68924 |
| 7.6475 | 125.6909 | 122.32901 | 116.9679 | 104.2951 | 63.75995 |
| 7.65 | 125.705 | 122.34314 | 116.9821 | 104.3368 | 63.83066 |
| 7.6525 | 125.7192 | 122.35726 | 117.0031 | 104.3786 | 63.90137 |
| 7.655 | 125.7264. | 122.37139 | 117.0241 | 104.4204 | 63.97208 |
| 7.6575 | 125.7405 | 122.38551 | 117.0452 | 104.4621 | 64.04279 |
| 7.66 | 125.7547 | 122.40656 | 117.0662 | 104.4969 | 64.1135 |
| 7.6625 | 125.7688 | 122.42069 | 117.0872 | 104.5387 | 64.18491 |
| 7.665 | 125.7829 | 122.43481 | 117.1083 | 104.5805 | 64.25562 |
| 7.6675 | 125.7971 | 122.44894 | 117.1293 | 104.6222 | 64.32703 |
| 7.67 | 125.8043 | 122.46307 | 117.1503 | 104.664 | 64.39843 |
| 7.6725 | 125.8184 | 122.48411 | 117.1713 | 104.7057 | 64.46914 |
| 7.675 | 125.8326 | 122.49824 | 117.1924 | 104.7406 | 64.64055 |
| 7.6775 | 125.8467 | 122.51236 | 117.2134 | 104.7823 | 64.61195 |
| 7.68 | 125.8608 | 122.52649 | 117.2275 | 104.8241 | 64.68405 |
| 7.6825 | 125.875 | 122.54062 | 117.2486 | 104.8658 | 64.75546 |
| 7.685 | 125.8822 | 122.55474 | 117.2696 | 104.9007 | 64.82687 |
| 7.6875 | 125.8963 | 122.57579 | 117.2906 | 104.9424 | 64.89896 |
| 7.69 | 125.9104 | 122.58991 | 117.3117 | 104.9842 | 64.97037 |
| 7.6925 | 125.9246 | 122.60404 | 117.3327 | 105.0259 | 65.04247 |
| 7.695 | 125.9387 | 122.61817 | 117.3537 | 105.0608 | 65.11457 |
| 7.6975 | 125.9529 | 122.63229 | 117.3747 | 105.1025 | 65.18598 |
| 7.7 | 125.9601 | 122.64642 | 117.3889 | 105.1443 | 65.25808 |
| 7.7025 | 125.9742 | 122.66747 | 117.4099 | 105.1791 | 65.33018 |
| 7.705 | 125.9883 | 122.68159 | 117.4309 | 105.2209 | 65.40228 |
| 7.7075 | 126.0025 | 122.69572 | 117.452 | 105.2557 | 65.47507 |
| 7.71 | 126.0166 | 122.70985 | 117.473 | 105.2975 | 65.54718 |
| 7.7125 | 126.0238 | 122.72397 | 117.494 | 105.3323 | 65.61928 |
| 7.715 | 126.038 | 122.73810 | 117.5081 | 105.3741 | 65.69207 |
| 7.7175 | 126.0521 | 122.75223 | 117.5292 | 105.4089 | 65.76417 |
| 7.72 | 126.0662 | 122.77327 | 117.5502 | 105.4507 | 65.83697 |
| 7.7225 | 126.0804 | 122.78740 | 117.5712 | 105.4855 | 65.90976 |
| 7.725 | 126.0945 | 122.80153 | 117.5923 | 105.5273 | 65.98187 |
| 7.7275 | 126.1017 | 122.81565 | 117.6133 | 105.5621 | 66.05466 |
| 7.73 | 126.1158 | 122.82978 | 117.6274 | 105.6039 | 66.12746 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 7.7325 | 126.13 | 122.84391 | 117.6484 | 105.6387 | 66.20025 |
| 7.735 | 126.1441 | 122.85803 | 117.6695 | 105.6805 | 66.27305 |
| 7.7375 | 126.1513 | 122.87216 | 117.6905 | 105.7153 | 66.34654 |
| 7.74 | 126.1655 | 122.89321 | 117.7115 | 105.7501 | 66.41934 |
| 7.7425 | 126.1796 | 122.90733 | 117.7257 | 105.7919 | 66.49213 |
| 7.745 | 126.1937 | 122.92146 | 117.7467 | 105.8267 | 66.56562 |
| 7.7475 | 126.2079 | 122.93559 | 117.7677 | 105.8616 | 66.83842 |
| 7.75 | 126.2151 | 122.94971 | 117.7888 | 105.9033 | 66.71191 |
| 7.7525 | 126.2292 | 122.96384 | 117.8029 | 105.9382 | 66.7854 |
| 7.755 | 126.2434 | 122.97797 | 117.8239 | 105.973 | 66.8582 |
| 7.7575 | 126.2575 | 122.99210 | 117.8449 | 106.0148 | 66.93169 |
| 7.76 | 126.2716 | 123.00622 | 117.866 | 106.0496 | 67.00518 |
| 7.7625 | 126.2788 | 123.02727 | 117.887 | 106.0845 | 67.07868 |
| 7.765 | 126.293 | 123.04140 | 117.9011 | 106.1193 | 67.15217 |
| 7.7675 | 126.3071 | 123.05552 | 117.9222 | 106.1611 | 67.22566 |
| 7.77 | 126.3213 | 123.06965 | 117.9432 | 106.1959 | 67.29915 |
| 7.7725 | 126.3285 | 123.08378 | 117.9573 | 106.2308 | 67.37265 |
| 7.775 | 126.3426 | 123.09790 | 117.9783 | 106.2656 | 67.44683 |
| 7.7775 | 126.3567 | 123.11203 | 117.9994 | 106.3004 | 67.52033 |
| 7.78 | 126.3709 | 123.12616 | 118.0204 | 106.3422 | 67.59382 |
| 7.7825 | 126.385 | 123.14029 | 118.0345 | 106.377 | 67.66801 |
| 7.785 | 126.3922 | 123.15441 | 118.0556 | 106.4119 | 67.7415 |
| 7.7875 | 126.4064 | 123.16854 | 118.0766 | 106.4467 | 67.81569 |
| 7.79 | 126.4205 | 123.18267 | 118.0976 | 106.4816 | 67.88918 |
| 7.7925 | 126.4346 | 123.20371 | 118.1117 | 106.5164 | 67.96337 |
| 7.795 | 126.4418 | 123.21784 | 118.1328 | 106.5513 | 68.03756 |
| 7.7975 | 126.456 | 123.23197 | 118.1538 | 106.5861 | 68.11175 |
| 7.8 | 126.4701 | 123.24610 | 118.1679 | 106.6209 | 68.18524 |
| 7.8025 | 126.4843 | 123.26022 | 118.189 | 106.6558 | 68.25943 |
| 7.805 | 126.4915 | 123.27435 | 118.21 | 106.6906 | 68.33362 |
| 7.8075 | 126.5056 | 123.28848 | 118.2241 | 106.7255 | 68.40781 |
| 7.81 | 126.5197 | 123.30261 | 118.2451 | 106.7603 | 68.482 |
| 7.8125 | 126.5339 | 123.31673 | 118.2662 | 106.7952 | 68.55619 |
| 7.815 | 126.5411 | 123.33086 | 118.2803 | 106.83 | 63.63038 |
| 7.8175 | 126.5552 | 123.34499 | 118.3013 | 106.8649 | 68.70526 |
| 7.82 | 126.5694 | 123.35912 | 118.3224 | 106.8997 | 68.77945 |
| 7.8225 | 126.5835 | 123.37324 | 118.3365 | 106.9345 | 68.85364 |
| 7.825 | 126.5907 | 123.38737 | 118.3575 | 106.9694 | 68.92784 |
| 7.8275 | 126.6048 | 123.40150 | 118.3785 | 107.0042 | 69.00272 |
| 7.83 | 126.619 | 123.41563 | 118.3927 | 107.0391 | 69.07691 |
| 7.8325 | 126.6331 | 123.42976 | 118.4137 | 107.0739 | 69.15111 |
| 7.835 | 126.6403 | 123.44388 | 118.4347 | 107.1088 | 69.22876 |
| 7.8375 | 126.6545 | 123.45801 | 118.4488 | 107.1367 | 69.29811 |
| 7.84 | 126.6686 | 123.47214 | 118.4699 | 107.1715 | 69.37438 |
| 7.8425 | 126.6758 | 123.49319 | 118.4909 | 107.2064 | 69.45065 |
| 7.845 | 126.69 | 123.50731 | 118.505 | 107.2412 | 69.52692 |
| 7.8475 | 126.7041 | 123.52144 | 118.5261 | 107.2761 | 69.59627 |
| 7.85 | 126.7182 | 123.53557 | 118.5402 | 107.3109 | 69.67254 |
| 7.8525 | 126.7254 | 123.54970 | 118.5612 | 107.3389 | 69.74881 |
| 7.855 | 126.7396 | 123.56382 | 118.5822 | 107.3737 | 69.82508 |
| 7.8575 | 126.7537 | 123.57795 | 118.5964 | 107.4086 | 69.89443 |
| 7.86 | 126.7678 | 123.59208 | 118.6174 | 107.4434 | 69.9707 |
| 7.8625 | 126.7751 | 123.60621 | 118.6384 | 107.4713 | 70.04698 |
| 7.865 | 126.7892 | 123.62034 | 118.6526 | 107.5062 | 70.12325 |
| 7.8675 | 126.8033 | 123.63446 | 118.6736 | 107.541 | 70.1926 |
| 7.87 | 126.8106 | 123.64859 | 118.6877 | 107.5759 | 70.26888 |
| 7.8725 | 126.8247 | 123.66272 | 118.7087 | 107.6038 | 70.34515 |
| 7.875 | 126.8388 | 123.67685 | 118.7298 | 107.6386 | 70.42142 |
| 7.8775 | 126.853 | 123.69098 | 118.7439 | 107.6735 | 70.4977 |
| 7.88 | 126.8602 | 123.70510 | 118.7649 | 107.7014 | 70.56705 |
| 7.8825 | 126.8743 | 123.71923 | 118.779 | 107.7363 | 70.64333 |
| 7.885 | 126.8884 | 123.73336 | 118.8001 | 107.7711 | 70.7196 |
| 7.8875 | 126.8957 | 123.74749 | 118.8142 | 107.799 | 70.79588 |
| 7.89 | 126.9098 | 123.76162 | 118.8352 | 107.8339 | 70.87215 |
| 7.8925 | 126.9239 | 123.77574 | 118.8563 | 107.8618 | 70.94151 |
| 7.895 | 126.9311 | 123.78987 | 118.8704 | 107.8967 | 71.01779 |
| 7.8975 | 126.9453 | 123.80400 | 118.8914 | 107.9315 | 71.09406 |
| 7.9 | 126.9594 | 123.81813 | 118.9055 | 107.9594 | 71.17034 |
| 7.9025 | 126.9736 | 123.83226 | 118.9266 | 107.9943 | 71.2397 |
| 7.905 | 126.9808 | 123.84638 | 118.9407 | 108.0222 | 71.31598 |
| 7.9075 | 126.9949 | 123.86051 | 118.9617 | 108.0571 | 71.39226 |
| 7.91 | 127.009 | 123.87464 | 118.9758 | 108.085 | 71.46853 |
| 7.9125 | 127.0163 | 123.88877 | 118.9969 | 108.1198 | 71.54481 |
| 7.915 | 127.0304 | 123.90290 | 119.011 | 108.1547 | 71.61417 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 7.9175 | 127.0445 | 123.91011 | 119.032 | 108.1826 | 71.69045 |
| 7.92 | 127.0517 | 123.92423 | 119.0531 | 108.2175 | 71.76673 |
| 7.9225 | 127.0659 | 123.93836 | 119.0672 | 108.2454 | 71.84301 |
| 7.925 | 127.08 | 123.95249 | 119.0882 | 108.2733 | 71.91237 |
| 7.9275 | 127.0872 | 123.96662 | 119.1023 | 108.3082 | 71.98865 |
| 7.93 | 127.1014 | 123.98075 | 119.1234 | 108.3361 | 72.06493 |
| 7.9325 | 127.1155 | 123.99487 | 119.1375 | 108.371 | 72.14121 |
| 7.935 | 127.1227 | 124.00900 | 119.1585 | 108.3989 | 72.2175 |
| 7.9375 | 127.1369 | 124.02313 | 119.1726 | 108.4337 | 72.28686 |
| 7.94 | 127.151 | 124.03726 | 119.1937 | 108.4617 | 72.36314 |
| 7.9425 | 127.1582 | 124.05139 | 119.2078 | 108.4965 | 72.43942 |
| 7.945 | 127.1723 | 124.06552 | 119.2288 | 108.5245 | 72.51571 |
| 7.9475 | 127.1865 | 124.07964 | 119.2429 | 108.5524 | 72.58507 |
| 7.95 | 127.1937 | 124.09377 | 119.264 | 108.5872 | 72.66135 |
| 7.9525 | 127.2078 | 124.10790 | 119.2781 | 108.6152 | 72.73764 |
| 7.955 | 127.222 | 124.12203 | 119.2991 | 108.6431 | 72.81392 |
| 7.9575 | 127.2292 | 124.13616 | 119.3133 | 108.678 | 72.88329 |
| 7.96 | 127.2433 | 124.15029 | 119.3343 | 108.7059 | 72.95957 |
| 7.9625 | 127.2575 | 124.16441 | 119.3484 | 108.7338 | 73.03586 |
| 7.965 | 127.2647 | 124.17854 | 119.3625 | 108.7687 | 73.11214 |
| 7.9675 | 127.2788 | 124.18575 | 119.3836 | 108.7966 | 73.18151 |
| 7.97 | 127.2929 | 124.19988 | 119.3977 | 108.8245 | 73.25779 |
| 7.9725 | 127.3002 | 124.21401 | 119.4187 | 108.8594 | 73.33408 |
| 7.975 | 127.3143 | 124.22814 | 119.4328 | 108.8873 | 73.41037 |
| 7.9775 | 127.3284 | 124.24227 | 119.4539 | 108.9152 | 73.47973 |
| 7.98 | 127.3356 | 124.25639 | 119.468 | 108.9432 | 73.55602 |
| 7.9825 | 127.3498 | 124.27052 | 119.489 | 108.978 | 73.63231 |
| 7.985 | 127.3639 | 124.28465 | 119.5031 | 109.006 | 73.7086 |
| 7.9875 | 127.3711 | 124.29878 | 119.5242 | 109.0339 | 73.77797 |
| 7.99 | 127.3853 | 124.31291 | 119.5383 | 109.0618 | 73.85425 |
| 7.9925 | 127.3994 | 124.32704 | 119.5524 | 109.0967 | 73.93054 |
| 7.995 | 127.4068 | 124.34117 | 119.5735 | 109.1246 | 73.99991 |
| 7.9975 | 127.4208 | 124.35530 | 119.5876 | 109.1525 | 74.0762 |
| 8 | 127.4349 | 124.36250 | 119.8086 | 109.1805 | 74.15249 |
| 8.0025 | 127.4421 | 124.37663 | 119.6227 | 109.2084 | 74.22186 |
| 8.005 | 127.4562 | 124.39076 | 119.6438 | 109.2433 | 74.29815 |
| 8.0075 | 127.4704 | 124.40489 | 119.6579 | 109.2712 | 74.37444 |
| 8.01 | 127.4776 | 124.41902 | 119.672 | 109.2991 | 74.44382 |
| 8.0125 | 127.4917 | 124.43315 | 119.693 | 109.3271 | 74.52011 |
| 8.015 | 127.4989 | 124.44728 | 119.7072 | 109.355 | 74.5964 |
| 8.0175 | 127.5131 | 124.46140 | 119.7282 | 109.3829 | 74.66577 |
| 8.02 | 127.5272 | 124.47553 | 119.7423 | 109.4109 | 74.74206 |
| 8.0225 | 127.5344 | 124.48966 | 119.7564 | 109.4457 | 74.81836 |
| 8.025 | 127.5486 | 124.49687 | 119.7775 | 109.4737 | 74.88773 |
| 8.0275 | 127.5627 | 124.51100 | 119.7916 | 109.5016 | 74.96402 |
| 8.03 | 127.5699 | 124.52513 | 119.8126 | 109.5295 | 75.0334 |
| 8.0325 | 127.5841 | 124.53926 | 119.8267 | 109.5575 | 75.10969 |
| 8.035 | 127.5913 | 124.55339 | 119.8409 | 109.5854 | 75.18599 |
| 8.0375 | 127.6054 | 124.56752 | 119.8619 | 109.6133 | 75.25536 |
| 8.04 | 127.6195 | 124.58164 | 119.876 | 109.6413 | 75.33165 |
| 8.0425 | 127.6268 | 124.59577 | 119.897 | 109.6692 | 75.40103 |
| 8.045 | 127.6409 | 124.60990 | 119.9112 | 109.6971 | 75.47733 |
| 8.0475 | 127.655 | 124.61711 | 119.9253 | 109.7251 | 75.55362 |
| 8.05 | 127.6622 | 124.63124 | 119.9463 | 109.753 | 75.623 |
| 8.0525 | 127.6764 | 124.64537 | 119.9604 | 109.7809 | 75.69929 |
| 8.055 | 127.6836 | 124.65950 | 119.9746 | 109.8089 | 75.76867 |
| 8.0575 | 127.6977 | 124.67363 | 119.9956 | 109.8368 | 75.84497 |
| 8.08 | 127.7119 | 124.68776 | 120.0097 | 109.8647 | 75.91435 |
| 8.0625 | 127.7191 | 124.70188 | 120.0308 | 109.8927 | 75.99064 |
| 8.065 | 127.7332 | 124.70909 | 120.0449 | 109.9206 | 76.06002 |
| 8.0675 | 127.7404 | 124.72322 | 120.059 | 109.9485 | 76.13632 |
| 8.07 | 127.7546 | 124.73735 | 120.08 | 109.9765 | 76.2057 |
| 8.0725 | 127.7687 | 124.75148 | 120.0941 | 110.0044 | 76.282 |
| 8.075 | 127.7759 | 124.76561 | 120.1083 | 110.0323 | 76.35138 |
| 8.0775 | 127.7901 | 124.77974 | 120.1293 | 110.0603 | 76.42768 |
| 8.08 | 127.7973 | 124.79387 | 120.1434 | 110.0882 | 76.49706 |
| 8.0825 | 127.8114 | 124.80108 | 120.1575 | 110.1162 | 76.57336 |
| 8.085 | 127.8256 | 124.81521 | 120.1786 | 110.1441 | 76.64274 |
| 8.0875 | 127.8328 | 124.82933 | 120.1927 | 110.172 | 76.71212 |
| 8.09 | 127.8469 | 124.84346 | 120.2068 | 110.193 | 76.78842 |
| 8.0925 | 127.8541 | 124.85759 | 120.2279 | 110.221 | 76.8578 |
| 8.095 | 127.8683 | 124.87172 | 120.242 | 110.2489 | 76.9341 |
| 8.0975 | 127.8824 | 124.88585 | 120.2561 | 110.2769 | 77.00348 |
| 8.1 | 127.8896 | 124.89306 | 120.2771 | 110.3048 | 77.07287 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 8.1025 | 127.9037 | 124.90719 | 120.2912 | 110.3327 | 77.14917 |
| 8.105 | 127.911 | 124.92132 | 120.3054 | 110.3607 | 77.21855 |
| 8.1075 | 127.9251 | 124.93545 | 120.3195 | 110.3886 | 77.29486 |
| 8.11 | 127.9392 | 124.94958 | 120.3405 | 110.4096 | 77.36424 |
| 8.1125 | 127.9464 | 124.96371 | 120.3546 | 110.4375 | 77.43362 |
| 8.115 | 127.9606 | 124.97091 | 120.3688 | 110.4655 | 77.50993 |
| 8.1175 | 127.9678 | 124.98504 | 120.3898 | 110.4934 | 77.57931 |
| 8.12 | 127.9819 | 124.99917 | 120.4039 | 110.5214 | 77.64869 |
| 8.1225 | 127.9961 | 125.01330 | 120.418 | 110.5424 | 77.71808 |
| 8.125 | 128.0033 | 125.02743 | 120.4391 | 110.5703 | 77.79439 |
| 8.1275 | 128.0174 | 125.03464 | 120.4532 | 110.5983 | 77.86377 |
| 8.13 | 128.0246 | 125.04877 | 120.4673 | 110.6262 | 77.93316 |
| 8.1325 | 128.0388 | 125.06290 | 120.4814 | 110.6541 | 78.00946 |
| 8.135 | 128.046 | 125.07703 | 120.5025 | 110.6751 | 78.07885 |
| 8.1375 | 128.0601 | 125.09116 | 120.5166 | 110.7031 | 78.14824 |
| 8.14 | 128.0743 | 125.10529 | 120.5307 | 110.731 | 78.21762 |
| 8.1425 | 128.0816 | 125.11250 | 120.5518 | 110.759 | 78.28701 |
| 8.145 | 128.0956 | 125.12663 | 120.5659 | 110.78 | 78.36332 |
| 8.1475 | 128.1028 | 125.14076 | 120.58 | 110.8079 | 78.43271 |
| 8.15 | 128.117 | 125.15488 | 120.5941 | 110.8358 | 78.50209 |
| 8.1525 | 128.1242 | 125.16901 | 120.6151 | 110.8638 | 78.57148 |
| 8.155 | 128.1383 | 125.17622 | 120.6293 | 110.8848 | 78.64087 |
| 8.1575 | 128.1525 | 125.19035 | 120.6434 | 110.9127 | 78.71026 |
| 8.16 | 128.1597 | 125.20448 | 120.6575 | 110.9407 | 78.78657 |
| 8.1625 | 128.1738 | 125.21861 | 120.6785 | 110.9617 | 78.85596 |
| 8.165 | 128.181 | 125.23274 | 120.6927 | 110.9896 | 78.92535 |
| 8.1675 | 128.1952 | 125.23995 | 120.7068 | 111.0176 | 78.99474 |
| 8.17 | 128.2024 | 125.25408 | 120.7209 | 111.0386 | 79.06413 |
| 8.1725 | 128.2165 | 125.26821 | 120.7419 | 111.0665 | 79.13352 |
| 8.175 | 128.2237 | 125.28234 | 120.7561 | 111.0945 | 79.20291 |
| 8.1775 | 128.2379 | 125.29647 | 120.7702 | 111.1155 | 79.2723 |
| 8.18 | 128.252 | 125.30368 | 120.7843 | 111.1434 | 79.34169 |
| 8.1825 | 128.2592 | 125.31781 | 120.7984 | 111.1714 | 79.41108 |
| 8.185 | 128.2733 | 125.33194 | 120.8195 | 111.1924 | 79.48048 |
| 8.1875 | 128.2806 | 125.34607 | 120.8336 | 111.2203 | 79.54987 |
| 8.19 | 128.2947 | 125.36019 | 120.8477 | 111.2413 | 79.61926 |
| 8.1925 | 128.3019 | 125.36740 | 120.8618 | 111.2693 | 79.68865 |
| 8.195 | 128.3161 | 125.38153 | 120.8829 | 111.2972 | 79.75805 |
| 8.1975 | 128.3233 | 125.39566 | 120.897 | 111.3182 | 79.82744 |
| 8.2 | 128.3374 | 125.40979 | 120.9111 | 111.3462 | 79.89683 |
| 8.2025 | 128.3515 | 125.41700 | 120.9252 | 111.3672 | 79.96623 |
| 8.205 | 128.3588 | 125.43113 | 120.9393 | 111.3951 | 80.03562 |
| 8.2075 | 128.3729 | 125.44526 | 120.9604 | 111.4231 | 80.10502 |
| 8.21 | 128.3801 | 125.45939 | 120.9745 | 111.4441 | 80.16749 |
| 8.2125 | 128.3942 | 125.47352 | 120.9886 | 111.472 | 80.23689 |
| 8.215 | 128.4015 | 125.48073 | 121.0027 | 111.4931 | 80.30628 |
| 8.2175 | 128.4156 | 125.49486 | 121.0169 | 111.521 | 80.37568 |
| 8.22 | 128.4228 | 125.50899 | 121.0379 | 111.542 | 80.44507 |
| 8.2225 | 128.4369 | 125.52312 | 121.052 | 111.57 | 80.51447 |
| 8.225 | 128.4442 | 125.53033 | 121.0661 | 111.591 | 80.57695 |
| 8.2275 | 128.4583 | 125.54446 | 121.0803 | 111.6189 | 80.64634 |
| 8.23 | 128.4655 | 125.55859 | 121.0944 | 111.6399 | 80.71574 |
| 8.2325 | 128.4797 | 125.57272 | 121.1154 | 111.6679 | 80.78514 |
| 8.235 | 128.4938 | 125.57992 | 121.1295 | 111.6958 | 80.84761 |
| 8.2375 | 128.501 | 125.59405 | 121.1437 | 111.7168 | 80.91701 |
| 8.24 | 128.5151 | 125.60818 | 121.1578 | 111.7448 | 80.98641 |
| 8.2425 | 128.5224 | 125.62231 | 121.1719 | 111.7658 | 81.05581 |
| 8.245 | 128.5365 | 125.62952 | 121.186 | 111.7868 | 81.11829 |
| 8.2475 | 128.5437 | 125.64365 | 121.2071 | 111.8148 | 81.18768 |
| 8.25 | 128.5578 | 125.65778 | 121.2212 | 111.8358 | 81.25708 |
| 8.2525 | 128.5651 | 125.67191 | 121.2353 | 111.8637 | 81.31956 |
| 8.255 | 128.5792 | 125.67912 | 121.2494 | 111.8847 | 81.38896 |
| 8.2575 | 128.5864 | 125.69325 | 121.2635 | 111.9127 | 81.45144 |
| 8.26 | 128.6005 | 125.70738 | 121.2777 | 111.9337 | 81.52084 |
| 8.2625 | 128.6078 | 125.72151 | 121.2987 | 111.9616 | 81.59024 |
| 8.265 | 128.6219 | 125.72872 | 121.3128 | 111.9827 | 81.65272 |
| 8.2675 | 128.6291 | 125.74285 | 121.3269 | 112.0106 | 81.72212 |
| 8.27 | 128.6433 | 125.75698 | 121.3411 | 112.0316 | 81.7846 |
| 8.2725 | 128.6505 | 125.77111 | 121.3552 | 112.0526 | 81.85401 |
| 8.275 | 128.6646 | 125.77832 | 121.3693 | 112.0806 | 81.91649 |
| 8.2775 | 128.6718 | 125.79245 | 121.3903 | 112.1016 | 81.98589 |
| 8.28 | 128.686 | 125.80658 | 121.4045 | 112.1295 | 82.04837 |
| 8.2825 | 128.6932 | 125.81379 | 121.4186 | 112.1506 | 82.11777 |
| 8.285 | 128.7073 | 125.82792 | 121.4327 | 112.1716 | 82.18025 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 8.2875 | 128.7145 | 125.84205 | 121.4468 | 112.1995 | 82.24966 |
| 8.29 | 128.7287 | 125.85618 | 121.4609 | 112.2205 | 82.31214 |
| 8.2925 | 128.7359 | 125.86338 | 121.4751 | 112.2416 | 82.38154 |
| 8.295 | 128.75 | 125.87751 | 121.4892 | 112.2695 | 82.44403 |
| 8.2975 | 128.7572 | 125.89164 | 121.5102 | 112.2905 | 82.50651 |
| 8.3 | 128.7714 | 125.90578 | 121.5243 | 112.3185 | 82.57592 |
| 8.3025 | 128.7786 | 125.91298 | 121.5385 | 112.3395 | 82.6384 |
| 8.305 | 128.7927 | 125.92711 | 121.5526 | 112.3605 | 82.70088 |
| 8.3075 | 128.7999 | 125.94124 | 121.5667 | 112.3885 | 82.77029 |
| 8.31 | 128.8141 | 125.94845 | 121.5808 | 112.4095 | 82.83277 |
| 8.3125 | 128.8213 | 125.96268 | 121.5949 | 112.4305 | 82.89526 |
| 8.315 | 128.8354 | 125.97671 | 121.6091 | 112.4584 | 82.95774 |
| 8.3175 | 128.8426 | 125.98392 | 121.6232 | 112.4795 | 83.02715 |
| 8.32 | 128.8568 | 125.99805 | 121.6442 | 112.5005 | 83.08963 |
| 8.3225 | 128.864 | 126.01218 | 121.6583 | 112.5284 | 83.15212 |
| 8.325 | 128.8781 | 126.02631 | 121.6725 | 112.5494 | 83.21461 |
| 8.3275 | 128.8853 | 126.03352 | 121.6866 | 112.5705 | 83.28401 |
| 8.33 | 128.8995 | 126.04765 | 121.7007 | 112.5915 | 83.3465 |
| 8.3325 | 128.9067 | 126.06178 | 121.7148 | 112.6194 | 83.40899 |
| 8.335 | 128.9208 | 126.06899 | 121.7289 | 112.6405 | 83.47147 |
| 8.3375 | 128.928 | 126.08312 | 121.7431 | 112.6615 | 83.53396 |
| 8.34 | 128.9422 | 126.09725 | 121.7572 | 112.6894 | 83.59645 |
| 8.3425 | 128.9494 | 126.11138 | 121.7713 | 112.7104 | 83.65894 |
| 8.345 | 128.9635 | 126.11859 | 121.7923 | 112.7315 | 83.72834 |
| 8.3475 | 128.9707 | 126.13272 | 121.8065 | 112.7525 | 83.79083 |
| 8.35 | 128.9849 | 126.14685 | 121.8206 | 112.7804 | 83.85332 |
| 8.3525 | 128.9921 | 126.15406 | 121.8347 | 112.8015 | 83.91581 |
| 8.355 | 129.0062 | 126.16819 | 121.8488 | 112.8225 | 83.9783 |
| 8.3575 | 129.0134 | 126.18232 | 121.8629 | 112.8435 | 84.04079 |
| 8.36 | 129.0276 | 126.18953 | 121.8771 | 112.8645 | 84.10328 |
| 8.3625 | 129.0348 | 126.20366 | 121.8912 | 112.8925 | 84.16577 |
| 8.365 | 129.0489 | 126.21779 | 121.9053 | 112.9135 | 84.22826 |
| 8.3675 | 129.0561 | 126.22500 | 121.9194 | 112.9345 | 84.29075 |
| 8.37 | 129.0703 | 126.23913 | 121.9336 | 112.9555 | 84.35324 |
| 8.3725 | 129.0775 | 126.25326 | 121.9477 | 112.9835 | 84.40881 |
| 8.375 | 129.0916 | 126.26046 | 121.9618 | 113.0045 | 84.4713 |
| 8.3775 | 129.0988 | 126.27460 | 121.9759 | 113.0255 | 84.53379 |
| 8.38 | 129.1061 | 126.28873 | 121.99 | 113.0465 | 84.59628 |
| 8.3825 | 129.1202 | 126.29593 | 122.0111 | 113.0676 | 84.65877 |
| 8.385 | 129.1274 | 126.31006 | 122.0252 | 113.0886 | 84.72126 |
| 8.3875 | 129.1416 | 126.32419 | 122.0393 | 113.1165 | 84.78375 |
| 8.39 | 129.1488 | 126.33140 | 122.0534 | 113.1376 | 84.83932 |
| 8.3925 | 129.1629 | 126.34553 | 122.0676 | 113.1586 | 84.90182 |
| 8.395 | 129.1701 | 126.35966 | 122.0817 | 113.1796 | 84.96431 |
| 8.3975 | 129.1843 | 126.36687 | 122.0958 | 113.2006 | 85.0268 |
| 8.4 | 129.1915 | 126.38100 | 122.1099 | 113.2217 | 85.08237 |
| 8.4025 | 129.2056 | 126.39513 | 122.124 | 113.2496 | 85.14487 |
| 8.405 | 129.2128 | 126.40234 | 122.1382 | 113.2706 | 85.20736 |
| 8.4075 | 129.227 | 126.41647 | 122.1523 | 113.2916 | 85.26986 |
| 8.41 | 129.2342 | 126.43060 | 122.1664 | 113.3127 | 85.32543 |
| 8.4125 | 129.2414 | 126.43781 | 122.1805 | 113.3337 | 85.38792 |
| 8.415 | 129.2555 | 126.45194 | 122.1947 | 113.3547 | 85.45042 |
| 8.4175 | 129.2627 | 126.46607 | 122.2088 | 113.3757 | 85.50599 |
| 8.42 | 129.2769 | 126.47328 | 122.2229 | 113.3968 | 85.56849 |
| 8.4225 | 129.2841 | 126.48741 | 122.237 | 113.4247 | 85.62406 |
| 8.425 | 129.2982 | 126.50154 | 122.2511 | 113.4457 | 85.68656 |
| 8.4275 | 129.3054 | 126.50875 | 122.2653 | 113.4668 | 85.74213 |
| 8.43 | 129.3196 | 126.52288 | 122.2794 | 113.4878 | 85.80462 |
| 8.4325 | 129.3268 | 126.53701 | 122.2935 | 113.5088 | 85.86712 |
| 8.435 | 129.3409 | 126.54422 | 122.3076 | 113.5298 | 85.92269 |
| 8.4375 | 129.3481 | 126.55835 | 122.3217 | 113.5508 | 85.98519 |
| 8.44 | 129.3554 | 126.57248 | 122.3359 | 113.5719 | 86.04077 |
| 8.4425 | 129.3695 | 126.57969 | 122.35 | 113.5929 | 86.10326 |
| 8.445 | 129.3767 | 126.59382 | 122.3641 | 113.6139 | 86.15884 |
| 8.4475 | 129.3908 | 126.60103 | 122.3782 | 113.6349 | 86.21441 |
| 8.45 | 129.3981 | 126.61516 | 122.3923 | 113.656 | 86.27691 |
| 8.4525 | 129.4122 | 126.62929 | 122.4065 | 113.6839 | 86.33249 |
| 8.455 | 129.4194 | 126.63650 | 122.4206 | 113.7049 | 86.39499 |
| 8.4575 | 129.4336 | 126.65063 | 122.4347 | 113.726 | 86.45056 |
| 8.46 | 129.4408 | 126.66476 | 122.4488 | 113.747 | 86.50614 |
| 8.4625 | 129.448 | 126.67197 | 122.463 | 113.768 | 86.56864 |
| 8.465 | 129.4621 | 126.68610 | 122.4771 | 113.789 | 86.62422 |
| 8.4675 | 129.4693 | 126.70023 | 122.4912 | 113.8101 | 86.67979 |
| 8.47 | 129.4835 | 126.70744 | 122.5053 | 113.8311 | 86.74229 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 8.4725 | 129.4907 | 126.72157 | 122.5194 | 113.8521 | 86.79787 |
| 8.475 | 129.5048 | 126.72878 | 122.5336 | 113.8731 | 86.85345 |
| 8.4775 | 129.512 | 126.74291 | 122.5477 | 113.8942 | 86.90903 |
| 8.48 | 129.5192 | 126.75704 | 122.5618 | 113.9152 | 86.97153 |
| 8.4825 | 129.5334 | 126.76425 | 122.5759 | 113.9362 | 87.02711 |
| 8.485 | 129.5406 | 126.77838 | 122.50 | 113.9572 | 87.08268 |
| 8.4875 | 129.5547 | 126.79251 | 122.6042 | 113.9783 | 87.13826 |
| 8.49 | 129.562 | 126.79972 | 122.6183 | 113.9993 | 87.19384 |
| 8.4925 | 129.5761 | 126.81385 | 122.6324 | 114.0203 | 87.25634 |
| 8.495 | 129.5833 | 126.82105 | 122.6465 | 114.0413 | 87.31192 |
| 8.4975 | 129.5905 | 126.83519 | 122.6607 | 114.0624 | 87.3675 |
| 8.5 | 129.6047 | 126.84932 | 122.6748 | 114.0834 | 87.42308 |
| 8.5025 | 129.6119 | 126.85652 | 122.6889 | 114.1044 | 87.47866 |
| 8.505 | 129.626 | 126.87066 | 122.703 | 114.1254 | 87.53424 |
| 8.5075 | 129.6332 | 126.87786 | 122.7171 | 114.1465 | 87.58983 |
| 8.51 | 129.6474 | 126.89199 | 122.7313 | 114.1675 | 87.64541 |
| 8.5125 | 129.6546 | 126.90613 | 122.7454 | 114.1816 | 87.70099 |
| 8.515 | 129.6618 | 126.91333 | 122.7596 | 114.2026 | 87.75657 |
| 8.5175 | 129.6759 | 126.92746 | 122.7667 | 114.2236 | 87.81215 |
| 8.52 | 129.6831 | 126.94160 | 122.7808 | 114.2447 | 87.86773 |
| 8.5225 | 129.6973 | 126.94880 | 122.7949 | 114.2657 | 87.92331 |
| 8.525 | 129.7045 | 128.96293 | 122.8091 | 114.2867 | 87.9789 |
| 8.5275 | 129.7117 | 126.97014 | 122.8232 | 114.3077 | 88.03448 |
| 8.53 | 129.7258 | 126.98427 | 122.8373 | 114.3288 | 88.09006 |
| 8.5325 | 129.7331 | 126.99840 | 122.8514 | 114.3498 | 88.14564 |
| 8.535 | 129.7472 | 127.00561 | 122.8656 | 114.3708 | 88.20123 |
| 8.5375 | 129.7544 | 127.01974 | 122.8797 | 114.3918 | 88.25681 |
| 8.54 | 129.7616 | 127.02695 | 122.8938 | 114.4129 | 88.30547 |
| 8.5425 | 129.7758 | 127.04108 | 122.9079 | 114.4339 | 88.36105 |
| 8.545 | 129.783 | 127.04829 | 122.922 | 114.448 | 88.41664 |
| 8.5475 | 129.7971 | 127.06242 | 122.9362 | 114.469 | 88.47222 |
| 8.55 | 129.8043 | 127.07655 | 122.9503 | 114.4901 | 88.52781 |
| 8.5525 | 129.8185 | 127.08376 | 122.9644 | 114.5111 | 88.57647 |
| 8.555 | 129.8257 | 127.09789 | 122.9785 | 114.5321 | 88.63205 |
| 8.5575 | 129.8329 | 127.10510 | 122.9857 | 114.5531 | 88.68764 |
| 8.56 | 129.847 | 127.11923 | 122.9999 | 114.5742 | 88.74322 |
| 8.5625 | 129.8542 | 127.13336 | 123.014 | 114.5952 | 88.79188 |
| 8.565 | 129.8684 | 127.14057 | 123.0281 | 114.6093 | 88.84747 |
| 8.5675 | 129.8756 | 127.15470 | 123.0422 | 114.6303 | 88.90306 |
| 8.57 | 129.8828 | 127.16191 | 123.0563 | 114.6513 | 88.95172 |
| 8.5725 | 129.8969 | 127.17604 | 123.0705 | 114.6724 | 89.0073 |
| 8.575 | 129.9042 | 127.18325 | 123.0846 | 114.6934 | 89.06289 |
| 8.5775 | 129.9114 | 127.19738 | 123.0987 | 114.7144 | 89.11155 |
| 8.58 | 129.9255 | 127.21151 | 123.1128 | 114.7355 | 89.16714 |
| 8.5825 | 129.9327 | 127.21872 | 123.1269 | 114.7496 | 89.22273 |
| 8.585 | 129.9469 | 127.23285 | 123.1341 | 114.7706 | 89.27139 |
| 8.5875 | 129.9541 | 127.24006 | 123.1483 | 114.7916 | 89.32698 |
| 8.59 | 129.9613 | 127.25419 | 123.1624 | 114.8126 | 89.37564 |
| 8.5925 | 129.9754 | 127.26832 | 123.1765 | 114.8337 | 89.43123 |
| 8.595 | 129.9826 | 127.27553 | 123.1906 | 114.8478 | 89.4799 |
| 8.5975 | 129.9968 | 127.28966 | 123.2048 | 114.8688 | 89.53548 |
| 8.6 | 130.004 | 127.29687 | 123.2189 | 114.8898 | 89.58415 |
| 8.6025 | 130.0112 | 127.31100 | 123.233 | 114.9108 | 89.63974 |
| 8.605 | 130.0253 | 127.31821 | 123.2471 | 114.9319 | 89.6884 |
| 8.6075 | 130.0326 | 127.33234 | 123.2543 | 114.9529 | 89.74399 |
| 8.61 | 130.0467 | 127.33955 | 123.2684 | 114.967 | 89.79266 |
| 8.6125 | 130.0539 | 127.35368 | 123.2826 | 114.988 | 89.84825 |
| 8.615 | 130.0611 | 127.36781 | 123.2967 | 115.0091 | 89.89691 |
| 8.6175 | 130.0753 | 127.37502 | 123.3108 | 115.0301 | 89.94558 |
| 8.62 | 130.0825 | 127.38915 | 123.3249 | 115.0442 | 90.00117 |
| 8.6225 | 130.0897 | 127.39636 | 123.3391 | 115.0652 | 90.04984 |
| 8.625 | 130.1038 | 127.41049 | 123.3532 | 115.0862 | 90.0985 |
| 8.6275 | 130.111 | 127.41769 | 123.3673 | 115.1073 | 90.15409 |
| 8.63 | 130.1252 | 127.43183 | 123.3745 | 115.1283 | 90.20276 |
| 8.6325 | 130.1324 | 127.43903 | 123.3886 | 115.1424 | 90.25143 |
| 8.635 | 130.1396 | 127.45317 | 123.4027 | 115.1634 | 90.30702 |
| 8.6375 | 130.1537 | 127.46730 | 123.4169 | 115.1845 | 90.35569 |
| 8.64 | 130.1609 | 127.47450 | 123.431 | 115.2055 | 90.40436 |
| 8.6425 | 130.1682 | 127.48864 | 123.4451 | 115.2196 | 90.45302 |
| 8.645 | 130.1823 | 127.49584 | 123.4592 | 115.2406 | 90.50862 |
| 8.6475 | 130.1895 | 127.50997 | 123.4664 | 115.2617 | 90.55729 |
| 8.65 | 130.2036 | 127.51718 | 123.4806 | 115.2827 | 90.60595 |
| 8.6525 | 130.2109 | 127.53131 | 123.4947 | 115.2968 | 90.65462 |
| 8.655 | 130.2181 | 127.53852 | 123.5088 | 115.3178 | 90.70329 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 8.6575 | 130.2322 | 127.55265 | 123.5229 | 115.3388 | 90.75196 |
| 8.66 | 130.2394 | 127.55986 | 123.537 | 115.3529 | 90.80755 |
| 8.6625 | 130.2466 | 127.57399 | 123.5512 | 115.374 | 90.85622 |
| 8.665 | 130.2608 | 127.58812 | 123.5584 | 115.395 | 90.90489 |
| 8.6675 | 130.268 | 127.59533 | 123.5725 | 115.416 | 90.95356 |
| 8.67 | 130.2752 | 127.60946 | 123.5866 | 115.4301 | 91.00223 |
| 8.6725 | 130.2893 | 127.61667 | 123.6007 | 115.4512 | 91.0509 |
| 8.675 | 130.2966 | 127.63080 | 123.6149 | 115.4722 | 91.09958 |
| 8.6775 | 130.3107 | 127.63801 | 123.629 | 115.4863 | 91.14825 |
| 8.68 | 130.3179 | 127.65214 | 123.6362 | 115.5073 | 91.19692 |
| 8.6825 | 130.3251 | 127.65935 | 123.6503 | 115.5284 | 91.24559 |
| 8.685 | 130.3393 | 127.67348 | 123.6644 | 115.5425 | 91.29426 |
| 8.6875 | 130.3465 | 127.68069 | 123.6785 | 115.5635 | 91.34293 |
| 8.69 | 130.3537 | 127.69482 | 123.6927 | 115.5845 | 91.3916 |
| 8.6925 | 130.3678 | 127.70203 | 123.7068 | 115.6055 | 91.44027 |
| 8.695 | 130.375 | 127.71616 | 123.7209 | 115.6196 | 91.48895 |
| 8.6975 | 130.3823 | 127.72337 | 123.7281 | 115.6407 | 91.53762 |
| 8.7 | 130.3964 | 127.73750 | 123.7422 | 115.6617 | 91.58629 |
| 8.7025 | 130.4036 | 127.75163 | 123.7564 | 115.6758 | 91.63496 |
| 8.705 | 130.4108 | 127.75884 | 123.7705 | 115.6968 | 91.68364 |
| 8.7075 | 130.425 | 127.77297 | 123.7846 | 115.7179 | 91.72538 |
| 8.71 | 130.4322 | 127.78018 | 123.7918 | 115.732 | 91.77406 |
| 8.7125 | 130.4463 | 127.79431 | 123.8059 | 115.753 | 91.82273 |
| 8.715 | 130.4535 | 127.80152 | 123.8201 | 115.7671 | 91.8714 |
| 8.7175 | 130.4607 | 127.81565 | 123.8342 | 115.7881 | 91.92008 |
| 8.72 | 130.4749 | 127.82286 | 123.8483 | 115.8092 | 91.96875 |
| 8.7225 | 130.4821 | 127.83699 | 123.8624 | 115.8233 | 92.0105 |
| 8.725 | 130.4893 | 127.84419 | 123.8696 | 115.8443 | 92.05918 |
| 8.7275 | 130.5034 | 127.85833 | 123.8837 | 115.8653 | 92.10785 |
| 8.73 | 130.5106 | 127.86553 | 123.8979 | 115.8794 | 92.15653 |
| 8.7325 | 130.5179 | 127.87967 | 123.912 | 115.9005 | 92.19828 |
| 8.735 | 130.532 | 127.88687 | 123.9261 | 115.9215 | 92.24695 |
| 8.7375 | 130.5392 | 127.90101 | 123.9333 | 115.9356 | 92.29563 |
| 8.74 | 130.5464 | 127.90821 | 123.9474 | 115.9566 | 92.33738 |
| 8.7425 | 130.5606 | 127.92234 | 123.9616 | 115.9707 | 92.38605 |
| 8.745 | 130.5678 | 127.92955 | 123.9757 | 115.9918 | 92.43473 |
| 8.7475 | 130.575 | 127.94368 | 123.9898 | 116.0128 | 92.47648 |
| 8.75 | 130.5891 | 127.95089 | 123.997 | 116.0269 | 92.52515 |
| 8.7525 | 130.5963 | 127.96502 | 124.0111 | 116.0479 | 92.57383 |
| 8.755 | 130.6036 | 127.97223 | 124.0252 | 116.062 | 92.61558 |
| 8.7575 | 130.6177 | 127.98636 | 124.0394 | 116.0831 | 92.66426 |
| 8.76 | 130.6249 | 127.99357 | 124.0535 | 116.1041 | 92.70601 |
| 8.7625 | 130.6321 | 128.00770 | 124.0607 | 116.1182 | 92.75469 |
| 8.765 | 130.6463 | 128.01491 | 124.0748 | 116.1392 | 92.80336 |
| 8.7675 | 130.6535 | 128.02904 | 124.0889 | 116.1533 | 92.84512 |
| 8.77 | 130.6607 | 128.03625 | 124.1031 | 116.1744 | 92.89379 |
| 8.7725 | 130.6748 | 128.05038 | 124.1103 | 116.1954 | 92.93555 |
| 8.775 | 130.682 | 128.05759 | 124.1244 | 116.2095 | 92.98423 |
| 8.7775 | 130.6892 | 128.07172 | 124.1385 | 116.2305 | 93.02598 |
| 8.78 | 130.7034 | 128.07893 | 124.1526 | 116.2446 | 93.07466 |
| 8.7825 | 130.7106 | 128.09306 | 124.1668 | 116.2657 | 93.11641 |
| 8.785 | 130.7178 | 128.10027 | 124.174 | 116.2798 | 93.16509 |
| 8.7875 | 130.7319 | 128.11440 | 124.1881 | 116.3008 | 93.20684 |
| 8.79 | 130.7392 | 128.12161 | 124.2022 | 116.3149 | 93.2486 |
| 8.7925 | 130.7464 | 128.13574 | 124.2163 | 116.3359 | 93.29728 |
| 8.795 | 130.7605 | 128.14294 | 124.2235 | 116.357 | 93.33903 |
| 8.7975 | 130.7677 | 128.15708 | 124.2376 | 116.3711 | 93.38771 |
| 8.8 | 130.7749 | 128.16428 | 124.2518 | 116.3921 | 93.42946 |
| 8.8025 | 130.7891 | 128.17842 | 124.2659 | 116.4062 | 93.47122 |
| 8.805 | 130.7963 | 128.18562 | 124.28 | 116.4273 | 93.5199 |
| 8.8075 | 130.8035 | 128.19283 | 124.2872 | 116.4414 | 93.56165 |
| 8.81 | 130.8176 | 128.20696 | 124.3013 | 116.4624 | 93.60341 |
| 8.8125 | 130.8248 | 128.21417 | 124.3155 | 116.4765 | 93.65209 |
| 8.815 | 130.8321 | 128.22830 | 124.3296 | 116.4975 | 93.69384 |
| 8.8175 | 130.8393 | 128.23551 | 124.3368 | 116.5116 | 93.7356 |
| 8.82 | 130.8534 | 128.24964 | 124.3509 | 116.5327 | 93.78428 |
| 8.8225 | 130.8606 | 128.25685 | 124.365 | 116.5468 | 93.82604 |
| 8.825 | 130.8678 | 128.27098 | 124.3792 | 116.5678 | 93.86779 |
| 8.8275 | 130.882 | 128.27819 | 124.3864 | 116.5819 | 93.90955 |
| 8.83 | 130.8892 | 128.29232 | 124.4005 | 116.6029 | 93.95823 |
| 8.8325 | 130.8964 | 128.29953 | 124.4146 | 116.617 | 93.99999 |
| 8.835 | 130.9105 | 128.31366 | 124.4287 | 116.6381 | 94.04174 |
| 8.8375 | 130.9178 | 128.32087 | 124.4359 | 116.6522 | 94.0835 |
| 8.84 | 130.925 | 128.33500 | 124.45 | 116.6732 | 94.12526 |

APPENDIX 1-continued

| Standard Mass Calculation | | | | | |
|---|---|---|---|---|---|
| | Temps | | | | |
| | 15.1 | 17.2 | 20.1 C. | 25.1 C. | 35.1 C. |
| 8.8425 | 130.9391 | 128.34221 | 124.4642 | 116.6873 | 94.17394 |
| 8.845 | 130.9463 | 128.35634 | 124.4783 | 116.7084 | 94.2157 |
| 8.8475 | 130.9535 | 128.36354 | 124.4855 | 116.7225 | 94.25746 |
| 8.85 | 130.9607 | 128.37075 | 124.4996 | 116.7435 | 94.29921 |
| 8.8525 | 130.9749 | 128.38488 | 124.5137 | 116.7576 | 94.34097 |
| 8.855 | 130.9821 | 128.39209 | 124.5279 | 116.7786 | 94.38273 |
| 8.8575 | 130.9893 | 128.40622 | 124.5351 | 116.7927 | 94.42449 |
| 8.86 | 131.0034 | 128.41343 | 124.5492 | 116.8138 | 94.46625 |
| 8.8625 | 131.0107 | 128.42756 | 124.5633 | 116.8279 | 94.508 |
| 8.865 | 131.0179 | 128.43477 | 124.5705 | 116.8489 | 94.55669 |
| 8.8675 | 131.032 | 128.44890 | 124.5848 | 116.863 | 94.59845 |
| 8.87 | 131.0392 | 128.45611 | 124.5988 | 116.884 | 94.64021 |
| 8.8725 | 131.0464 | 128.47024 | 124.6129 | 116.8982 | 94.68197 |
| 8.875 | 131.0536 | 128.47745 | 124.6201 | 116.9192 | 94.72372 |
| 8.8775 | 131.0678 | 128.48466 | 124.6342 | 116.9333 | 94.76548 |
| 8.88 | 131.075 | 128.49879 | 124.6483 | 116.9474 | 94.80724 |
| 8.8825 | 131.0822 | 128.50599 | 124.6624 | 116.9684 | 94.849 |
| 8.885 | 131.0963 | 128.52013 | 124.6696 | 116.9825 | 94.89076 |
| 8.8875 | 131.1036 | 128.52733 | 124.6838 | 117.0036 | 94.93252 |
| 8.89 | 131.1108 | 128.54147 | 124.6979 | 117.0177 | 94.96736 |
| 8.8925 | 131.1249 | 128.54867 | 124.7051 | 117.0387 | 95.00912 |
| 8.895 | 131.1321 | 128.56281 | 124.7192 | 117.0528 | 95.05088 |
| 8.8975 | 131.1393 | 128.57001 | 124.7333 | 117.0669 | 95.09264 |
| 8.9 | 131.1465 | 128.58415 | 124.7475 | 117.088 | 95.1344 |
| 8.9025 | 131.1607 | 128.59135 | 124.7647 | 117.1021 | 95.17616 |
| 8.905 | 131.1679 | 128.59856 | 124.7688 | 117.1231 | 95.21792 |
| 8.9075 | 131.1751 | 128.61269 | 124.7829 | 117.1372 | 95.25968 |
| 8.91 | 131.1892 | 128.61990 | 124.7901 | 117.1582 | 95.30144 |
| 8.9125 | 131.1965 | 128.63403 | 124.8042 | 117.1723 | 95.33628 |
| 8.915 | 131.2037 | 128.64124 | 124.8184 | 117.1865 | 95.37804 |
| 8.9175 | 131.2109 | 128.65537 | 124.8256 | 117.2075 | 95.4198 |
| 8.92 | 131.225 | 128.66258 | 124.8397 | 117.2216 | 95.46157 |
| 8.9225 | 131.2322 | 128.66978 | 124.8538 | 117.2426 | 95.50333 |
| 8.925 | 131.2395 | 128.68392 | 124.8679 | 117.2567 | 95.54509 |
| 8.9275 | 131.2536 | 128.69112 | 124.8751 | 117.2708 | 95.57993 |
| 8.93 | 131.2608 | 128.70526 | 124.8893 | 117.2919 | 95.62169 |
| 8.9325 | 131.268 | 128.71246 | 124.9034 | 117.306 | 95.66345 |
| 8.935 | 131.2752 | 128.72660 | 124.9106 | 117.327 | 95.70521 |
| 8.9375 | 131.2894 | 128.73380 | 124.9247 | 117.3411 | 95.74005 |
| 8.94 | 131.2966 | 128.74101 | 124.9388 | 117.3552 | 95.78181 |
| 8.9425 | 131.3038 | 128.75514 | 124.946 | 117.3763 | 95.82358 |
| 8.945 | 131.3179 | 128.76235 | 124.9601 | 117.3904 | 95.85842 |
| 8.9475 | 131.3251 | 128.77648 | 124.9743 | 117.4114 | 95.90018 |
| 8.95 | 131.3324 | 128.78369 | 124.9884 | 117.4255 | 95.94194 |
| 8.9525 | 131.3396 | 128.79782 | 124.9956 | 117.4396 | 95.97678 |
| 8.955 | 131.3537 | 128.80503 | 125.0097 | 117.4607 | 96.01854 |
| 8.9575 | 131.3609 | 128.81223 | 125.0238 | 117.4748 | 96.06031 |
| 8.96 | 131.3681 | 128.82637 | 125.031 | 117.4889 | 96.09515 |
| 8.9625 | 131.3753 | 128.83357 | 125.0452 | 117.5099 | 96.13691 |
| 8.965 | 131.3895 | 128.84771 | 125.0593 | 117.524 | 96.17868 |
| 8.9675 | 131.3967 | 128.85491 | 125.0665 | 117.5381 | 96.21352 |
| 8.97 | 131.4039 | 128.86905 | 125.0806 | 117.5592 | 96.25528 |
| 8.9725 | 131.418 | 128.87625 | 125.0947 | 117.5733 | 96.29012 |
| 8.975 | 131.4253 | 128.88346 | 125.1019 | 117.5874 | 96.33188 |
| 8.9775 | 131.4325 | 128.89759 | 125.1161 | 117.6084 | 96.36672 |
| 8.98 | 131.4397 | 128.90480 | 125.1302 | 117.6225 | 96.40849 |
| 8.9825 | 131.4538 | 128.91893 | 125.1374 | 117.6435 | 96.45025 |
| 8.985 | 131.461 | 128.92614 | 125.1515 | 117.6577 | 96.48509 |
| 8.9875 | 131.4682 | 128.93334 | 125.1656 | 117.6718 | 96.52686 |
| 8.99 | 131.4755 | 128.94748 | 125.1728 | 117.6928 | 96.5617 |
| 8.9925 | 131.4896 | 128.95468 | 125.187 | 117.7069 | 96.60347 |
| 8.995 | 131.4968 | 128.96882 | 125.2011 | 117.721 | 96.63831 |
| 8.9975 | 131.504 | 128.97602 | 125.2083 | 117.742 | 96.68007 |
| 9 | 131.5112 | 128.98323 | 125.2224 | 117.7562 | 96.71491 |

APPENDIX 2

Reverse Pressure lookup

| | | Temp | | | |
|---|---|---|---|---|---|
| | | 17.2 C. | 20.1 C. | 25.1 C. | 35.1 C. |
| Mass | 30.0 | | 5.005 | 5.1975 | 5.575 |
| | 30.1 | | 5.0125 | 5.205 | 5.5875 |
| | 30.2 | | 5.0225 | 5.215 | 5.5975 |
| | 30.3 | | 5.03 | 5.225 | 5.6075 |
| | 30.4 | | 5.0375 | 5.2325 | 5.6175 |
| | 30.5 | | 5.045 | 5.2425 | 5.6275 |
| | 30.6 | | 5.055 | 5.25 | 5.64 |
| | 30.7 | | 5.0625 | 5.26 | 5.65 |
| | 30.8 | | 5.07 | 5.2675 | 5.66 |
| | 30.9 | | 5.0775 | 5.2775 | 5.67 |
| | 31.0 | | 5.085 | 5.285 | 5.68 |
| | 31.1 | | 5.0925 | 5.295 | 5.69 |
| | 31.2 | | 5.1 | 5.3025 | 5.7 |
| | 31.3 | | 5.11 | 5.3125 | 5.71 |
| | 31.4 | | 5.1175 | 5.32 | 5.72 |
| | 31.5 | 5.005 | 5.125 | 5.3275 | 5.73 |
| | 31.6 | 5.0125 | 5.1325 | 5.3375 | 5.7425 |
| | 31.7 | 5.02 | 5.14 | 5.345 | 5.7525 |
| | 31.8 | 5.025 | 5.1475 | 5.355 | 5.7625 |
| | 31.9 | 5.0325 | 5.155 | 5.3625 | 5.77 |
| | 32.0 | 5.04 | 5.1625 | 5.37 | 5.78 |
| | 32.1 | 5.0475 | 5.17 | 5.38 | 5.79 |
| | 32.2 | 5.055 | 5.1775 | 5.3875 | 5.8 |
| | 32.3 | 5.06 | 5.185 | 5.395 | 5.81 |
| | 32.4 | 5.0675 | 5.1925 | 5.4025 | 5.82 |
| | 32.5 | 5.075 | 5.2 | 5.4125 | 5.83 |
| | 32.6 | 5.08 | 5.205 | 5.42 | 5.84 |
| | 32.7 | 5.0875 | 5.2125 | 5.4275 | 5.85 |
| | 32.8 | 5.095 | 5.22 | 5.435 | 5.86 |
| | 32.9 | 5.1 | 5.2275 | 5.4425 | 5.8675 |
| | 33.0 | 5.1075 | 5.235 | 5.4525 | 5.8775 |
| | 33.1 | 5.115 | 5.2425 | 5.46 | 5.8875 |
| | 33.2 | 5.12 | 5.25 | 5.4675 | 5.8975 |
| | 33.3 | 5.1275 | 5.255 | 5.475 | 5.9075 |
| | 33.4 | 5.1325 | 5.2625 | 5.4825 | 5.915 |
| | 33.5 | 5.14 | 5.27 | 5.49 | 5.925 |
| | 33.6 | 5.1475 | 5.2775 | 5.4975 | 5.935 |
| | 33.7 | 5.1525 | 5.2825 | 5.505 | 5.945 |
| | 33.8 | 5.16 | 5.29 | 5.5125 | 5.9525 |
| | 33.9 | 5.165 | 5.2975 | 5.52 | 5.9625 |
| | 34.0 | 5.1725 | 5.3025 | 5.5275 | 5.9725 |
| | 34.1 | 5.1775 | 5.31 | 5.535 | 5.98 |
| | 34.2 | 5.185 | 5.3175 | 5.5425 | 5.99 |
| | 34.3 | 5.19 | 5.3225 | 5.55 | 6 |
| | 34.4 | 5.195 | 5.33 | 5.5575 | 6.0075 |
| | 34.5 | 5.2025 | 5.3375 | 5.565 | 6.0175 |
| | 34.6 | 5.2075 | 5.3425 | 5.5725 | 6.025 |
| | 34.7 | 5.215 | 5.35 | 5.58 | 6.035 |
| | 34.8 | 5.22 | 5.355 | 5.5875 | 6.045 |
| | 34.9 | 5.225 | 5.3625 | 5.595 | 6.0525 |
| | 35.0 | 5.2325 | 5.3675 | 5.6025 | 6.0625 |
| | 35.1 | 5.2375 | 5.375 | 5.61 | 6.07 |
| | 35.2 | 5.2425 | 5.38 | 5.6175 | 6.08 |
| | 35.3 | 5.2475 | 5.3375 | 5.6225 | 6.0875 |
| | 35.4 | 5.255 | 5.3925 | 5.63 | 6.0975 |
| | 35.5 | 5.26 | 5.4 | 5.6375 | 6.105 |
| | 35.6 | 5.265 | 5.405 | 5.645 | 6.115 |
| | 35.7 | 5.2725 | 5.4125 | 5.6525 | 6.1225 |
| | 35.8 | 5.2775 | 5.4175 | 5.6575 | 6.13 |
| | 35.9 | 5.2825 | 5.425 | 5.665 | 6.14 |
| | 36.0 | 5.2875 | 5.43 | 5.6725 | 6.1475 |
| | 36.1 | 5.2925 | 5.435 | 5.68 | 6.1575 |
| | 36.2 | 5.2975 | 5.4425 | 5.685 | 6.165 |
| | 36.3 | 5.305 | 5.4475 | 5.6925 | 6.1725 |
| | 36.4 | 5.31 | 5.4525 | 5.7 | 6.1825 |
| | 36.5 | 5.315 | 5.46 | 5.705 | 6.19 |
| | 36.6 | 5.32 | 5.465 | 5.7125 | 6.1975 |
| | 36.7 | 5.325 | 5.47 | 5.72 | 6.2075 |
| | 36.8 | 5.33 | 5.4775 | 5.725 | 6.215 |
| | 36.9 | 5.335 | 5.4825 | 5.7325 | 6.2225 |
| | 37.0 | 5.34 | 5.4875 | 5.74 | 6.2325 |
| | 37.1 | 5.345 | 5.4925 | 5.745 | 6.24 |
| | 37.2 | 5.35 | 5.5 | 5.7525 | 6.2475 |
| | 37.3 | 5.355 | 5.505 | 5.7575 | 6.255 |

APPENDIX 2-continued

Reverse Pressure lookup

| | | Temp | | | |
|---|---|---|---|---|---|
| | | 17.2 C. | 20.1 C. | 25.1 C. | 35.1 C. |
| | 37.4 | 5.36 | 5.51 | 5.765 | 6.265 |
| | 37.5 | 5.365 | 5.515 | 5.77 | 6.2725 |
| | 37.6 | 5.37 | 5.52 | 5.7775 | 6.28 |
| | 37.7 | 5.375 | 5.5275 | 5.7825 | 6.2875 |
| | 37.8 | 5.38 | 5.5325 | 5.79 | 6.295 |
| | 37.9 | 5.335 | 5.5375 | 5.795 | 6.305 |
| | 38.0 | 5.39 | 5.5425 | 5.8025 | 6.3125 |
| | 38.1 | 5.395 | 5.5475 | 5.8075 | 6.32 |
| | 38.2 | 5.4 | 5.5525 | 5.815 | 6.3275 |
| | 38.3 | 5.405 | 5.5575 | 5.82 | 6.335 |
| | 38.4 | 5.41 | 5.5625 | 5.8275 | 6.3425 |
| | 38.5 | 5.4125 | 5.5675 | 5.8325 | 6.35 |
| | 38.6 | 5.4175 | 5.5725 | 5.8375 | 6.3575 |
| | 38.7 | 5.4225 | 5.58 | 5.845 | 6.3675 |
| | 38.8 | 5.4275 | 5.585 | 5.85 | 6.375 |
| | 38.9 | 5.4325 | 5.59 | 5.8575 | 6.3825 |
| | 39.0 | 5.4375 | 5.595 | 5.8625 | 6.39 |
| | 39.1 | 5.44 | 5.6 | 5.8675 | 6.3975 |
| | 39.2 | 5.445 | 5.605 | 5.875 | 6.405 |
| | 39.3 | 5.45 | 5.6075 | 5.88 | 6.4125 |
| | 39.4 | 5.455 | 5.6125 | 5.385 | 6.42 |
| | 39.5 | 5.4575 | 5.6175 | 5.8925 | 6.4275 |
| | 39.6 | 5.4625 | 5.6225 | 5.8975 | 6.435 |
| | 39.7 | 5.4675 | 5.6275 | 5.9025 | 6.4425 |
| | 39.8 | 5.47 | 5.6325 | 5.9075 | 6.45 |
| | 39.9 | 5.475 | 5.6375 | 5.915 | 6.4575 |
| | 40.0 | 5.48 | 5.6425 | 5.92 | 6.4625 |
| | 40.1 | 5.4825 | 5.6475 | 5.925 | 6.47 |
| | 40.2 | 5.4875 | 5.6525 | 5.93 | 6.4775 |
| | 40.3 | 5.4925 | 5.655 | 5.935 | 6.485 |
| | 40.4 | 5.495 | 5.66 | 5.9425 | 6.4925 |
| | 40.5 | 5.5 | 5.665 | 5.9475 | 6.5 |
| | 40.6 | 5.505 | 5.67 | 5.9525 | 6.5075 |
| | 40.7 | 5.5075 | 5.675 | 5.9575 | 6.515 |
| | 40.8 | 5.5125 | 5.68 | 5.9625 | 6.52 |
| | 40.9 | 5.515 | 5.6825 | 5.9675 | 6.5275 |
| | 41.0 | 5.52 | 5.6875 | 5.975 | 6.535 |
| | 41.1 | 5.5225 | 5.6925 | 5.98 | 6.5425 |
| | 41.2 | 5.5275 | 5.6975 | 5.985 | 6.55 |
| | 41.3 | 5.53 | 5.7 | 5.99 | 6.555 |
| | 41.4 | 5.535 | 5.705 | 5.995 | 6.5625 |
| | 41.5 | 5.5375 | 5.71 | 6 | 6.57 |
| | 41.6 | 5.5425 | 5.7125 | 6.005 | 6.5775 |
| | 41.7 | 5.545 | 5.7175 | 6.01 | 6.585 |
| | 41.8 | 5.55 | 5.7225 | 6.015 | 6.59 |
| | 41.9 | 5.5525 | 5.725 | 6.02 | 6.5975 |
| | 42.0 | 5.5575 | 5.73 | 6.025 | 6.605 |
| | 42.1 | 5.56 | 5.735 | 6.03 | 6.61 |
| | 42.2 | 5.565 | 5.7375 | 6.035 | 6.6175 |
| | 42.3 | 5.5675 | 5.7425 | 6.04 | 6.625 |
| | 42.4 | 5.57 | 5.7475 | 6.045 | 6.63 |
| | 42.5 | 5.575 | 5.75 | 6.05 | 6.6375 |
| | 42.6 | 5.5775 | 5.755 | 6.055 | 6.645 |
| | 42.7 | 5.5825 | 5.7575 | 6.06 | 6.65 |
| | 42.8 | 5.585 | 5.7625 | 6.065 | 6.6575 |
| | 42.9 | 5.5875 | 5.765 | 6.07 | 6.665 |
| | 43.0 | 5.5925 | 5.77 | 6.075 | 6.67 |
| | 43.1 | 5.595 | 5.775 | 6.08 | 6.8775 |
| | 43.2 | 5.5975 | 5.7775 | 6.0825 | 6.6825 |
| | 43.3 | 5.6 | 5.7825 | 6.0875 | 6.69 |
| | 43.4 | 5.605 | 5.735 | 6.0925 | 6.6975 |
| | 43.5 | 5.6075 | 5.79 | 6.0975 | 6.7025 |
| | 43.6 | 5.61 | 5.7925 | 6.1025 | 6.71 |
| | 43.7 | 5.615 | 5.7975 | 6.1075 | 6.715 |
| | 43.8 | 5.6175 | 5.8 | 6.1125 | 6.7225 |
| | 43.9 | 5.62 | 5.8025 | 6.115 | 6.7275 |
| | 44.0 | 5.6225 | 5.8075 | 6.12 | 6.735 |
| | 44.1 | 5.6275 | 5.81 | 6.125 | 6.74 |
| | 44.2 | 5.63 | 5.815 | 6.13 | 6.7475 |
| | 44.3 | 5.6325 | 5.8175 | 6.135 | 6.7525 |
| | 44.4 | 5.635 | 5.8225 | 6.1375 | 6.713 |
| | 44.5 | 5.6375 | 5.825 | 6.1425 | 6.765 |
| | 44.6 | 5.64 | 5.8275 | 6.1475 | 6.7725 |
| | 44.7 | 5.645 | 5.8325 | 6.1525 | 6.7775 |

APPENDIX 2-continued

| Reverse Pressure lookup | | | | |
|---|---|---|---|---|
| | Temp | | | |
| | 17.2 C. | 20.1 C. | 25.1 C. | 35.1 C. |
| 44.8 | 5.6475 | 5.835 | 6.155 | 6.785 |
| 44.9 | 5.65 | 5.84 | 6.16 | 6.79 |
| 45.0 | 5.6525 | 5.8425 | 6.165 | 6.795 |
| 45.1 | 5.655 | 5.845 | 6.1675 | 6.8925 |
| 45.2 | 5.6575 | 5.85 | 6.1725 | 6.8075 |
| 45.3 | 5.66 | 5.8525 | 6.1775 | 6.815 |
| 45.4 | 5.665 | 5.855 | 6.1825 | 6.132 |
| 45.5 | 5.6675 | 5.8575 | 6.185 | 6.825 |
| 45.6 | 5.67 | 5.8625 | 6.19 | 6.8325 |
| 45.7 | 5.6725 | 5.865 | 6.195 | 6.8375 |
| 45.8 | 5.675 | 5.8675 | 6.1975 | 6.845 |
| 45.9 | 5.6775 | 5.8725 | 6.2025 | 6.85 |
| 46.0 | 5.68 | 5.875 | 6.205 | 6.855 |
| 46.1 | 5.6825 | 5.8775 | 6.21 | 6.8625 |
| 46.2 | 5.685 | 5.88 | 6.215 | 6.8675 |
| 46.3 | 5.6875 | 5.885 | 6.2175 | 6.8725 |
| 46.4 | 5.69 | 5.8875 | 6.2225 | 6.8775 |
| 46.5 | 5.6925 | 5.89 | 6.225 | 6.885 |
| 46.6 | 5.695 | 5.8925 | 6.23 | 6.89 |
| 46.7 | 5.6975 | 5.895 | 6.235 | 6.895 |
| 46.8 | 5.7 | 5.9 | 6.2375 | 6.9025 |
| 46.9 | 5.7025 | 5.9025 | 6.2425 | 6.9075 |
| 47.0 | 5.705 | 5.905 | 6.245 | 6.9125 |
| 47.1 | 5.7075 | 5.9075 | 6.25 | 6.9175 |
| 47.2 | 5.71 | 5.91 | 6.2525 | 6.925 |
| 47.3 | 5.7125 | 5.9125 | 6.2575 | 6.93 |
| 47.4 | 5.715 | 5.9175 | 6.26 | 6.935 |
| 47.5 | 5.7175 | 5.92 | 6.265 | 6.94 |
| 47.6 | 5.7175 | 5.9225 | 6.2675 | 6.945 |
| 47.7 | 5.72 | 5.925 | 6.2725 | 6.9525 |
| 47.8 | 5.7225 | 5.9275 | 6.275 | 6.9575 |
| 47.9 | 5.725 | 5.93 | 6.28 | 6.9625 |
| 48.0 | 5.7275 | 5.9325 | 6.2825 | 6.9675 |
| 48.1 | 5.73 | 5.935 | 6.2875 | 6.9725 |
| 48.2 | 5.7325 | 5.9375 | 6.29 | 6.98 |
| 48.3 | 5.735 | 5.94 | 6.2925 | 6.985 |
| 48.4 | 5.735 | 5.9425 | 6.2975 | 6.99 |
| 48.5 | 5.7375 | 5.9475 | 6.3 | 6.995 |
| 48.6 | 5.74 | 5.95 | 6.305 | 7 |
| 48.7 | 5.7425 | 5.9525 | 6.3075 | 7.005 |
| 48.8 | 5.745 | 5.955 | 6.31 | 7.01 |
| 48.9 | 5.745 | 5.9575 | 6.315 | 7.015 |
| 49.0 | 5.7475 | 5.96 | 6.3175 | 7.0225 |
| 49.1 | 5.75 | 5.9625 | 6.3225 | 7.0275 |
| 49.2 | 5.7525 | 5.965 | 6.325 | 7.0325 |
| 49.3 | 5.755 | 5.9675 | 6.3275 | 7.0375 |
| 49.4 | 5.755 | 5.97 | 6.3325 | 7.0425 |
| 49.5 | 5.7575 | 5.9725 | 6.335 | 7.0475 |
| 49.6 | 5.76 | 5.975 | 6.3375 | 7.0525 |
| 49.7 | 5.7625 | 5.9775 | 6.3425 | 7.0575 |
| 49.8 | 5.7625 | 5.9775 | 6.345 | 7.0625 |
| 49.9 | 5.765 | 5.93 | 6.3475 | 7.0675 |
| 50.0 | 5.7675 | 5.9825 | 6.3525 | 7.0725 |
| 50.1 | 5.77 | 5.985 | 6.355 | 7.0775 |
| 50.2 | 5.77 | 5.9875 | 6.3575 | 7.0825 |
| 50.3 | 5.7725 | 5.99 | 6.36 | 7.0875 |
| 50.4 | 5.775 | 5.9925 | 6.3135 | 7.0925 |
| 50.5 | 5.775 | 5.995 | 6.3675 | 7.0975 |
| 50.6 | 5.7775 | 5.9975 | 6.37 | 7.1025 |
| 50.7 | 5.78 | 6 | 6.375 | 7.1075 |
| 50.8 | 5.78 | 6.0025 | 6.3775 | 7.1125 |
| 50.9 | 5.7825 | 6.005 | 6.38 | 7.1175 |
| 51.0 | 5.785 | 6.005 | 6.3825 | 7.1225 |
| 51.1 | 5.785 | 6.0075 | 6.3875 | 7.1275 |
| 51.2 | 5.7875 | 6.01 | 6.39 | 7.1325 |
| 51.3 | 5.79 | 6.0125 | 6.3925 | 7.1375 |
| 51.4 | 5.79 | 6.015 | 6.395 | 7.1425 |
| 51.5 | 5.7925 | 6.0175 | 6.3975 | 7.1475 |
| 51.6 | 5.7925 | 6.0175 | 6.4025 | 7.1525 |
| 51.7 | 5.795 | 6.02 | 6.405 | 7.1575 |
| 51.8 | 5.7975 | 6.0225 | 6.4075 | 7.1625 |
| 51.9 | 5.7975 | 6.025 | 6.41 | 7.165 |
| 52.0 | 5.8 | 6.0275 | 6.4125 | 7.17 |
| 52.1 | 5.8 | 6.03 | 6.415 | 7.175 |

APPENDIX 2-continued

| Reverse Pressure lookup | | | | |
|---|---|---|---|---|
| | Temp | | | |
| | 17.2 C. | 20.1 C. | 25.1 C. | 35.1 C. |
| 52.2 | 5.8025 | 6.03 | 6.42 | 7.18 |
| 52.3 | 5.805 | 6.0325 | 6.4225 | 7.185 |
| 52.4 | 5.805 | 6.035 | 6.425 | 7.19 |
| 52.5 | 5.8075 | 6.0375 | 6.4275 | 7.195 |
| 52.6 | 5.8075 | 6.0375 | 6.43 | 7.2 |
| 52.7 | 5.81 | 6.04 | 6.4325 | 7.2025 |
| 52.8 | 5.81 | 6.0425 | 6.435 | 7.2075 |
| 52.9 | 5.8125 | 6.045 | 6.44 | 7.2125 |
| 53.0 | 5.8125 | 6.045 | 6.4425 | 7.2175 |
| 53.1 | 5.815 | 6.0475 | 6.445 | 7.2225 |
| 53.2 | 5.815 | 6.05 | 6.4475 | 7.2275 |
| 53.3 | 5.8175 | 6.0525 | 6.45 | 7.23 |
| 53.4 | 5.82 | 6.0525 | 6.4525 | 7.235 |
| 53.5 | 5.82 | 6.055 | 6.455 | 7.24 |
| 53.6 | 5.8225 | 6.0575 | 6.4575 | 7.245 |
| 53.7 | 5.8225 | 6.0575 | 6.46 | 7.25 |
| 53.8 | 5.8225 | 6.06 | 6.4625 | 7.255 |
| 53.9 | 5.825 | 6.0625 | 6.465 | 7.2575 |
| 54.0 | 5.825 | 6.065 | 6.4675 | 7.2625 |
| 54.1 | 5.8275 | 6.065 | 6.4725 | 7.2675 |
| 54.2 | 5.8275 | 6.0675 | 6.475 | 7.2725 |
| 54.3 | 5.83 | 6.07 | 6.4775 | 7.275 |
| 54.4 | 5.63 | 6.07 | 6.48 | 7.23 |
| 54.5 | 5.8325 | 6.0725 | 6.4825 | 7.235 |
| 54.6 | 5.8325 | 6.075 | 6.485 | 7.29 |
| 54.7 | 5.835 | 6.075 | 6.4875 | 7.2925 |
| 54.8 | 5.835 | 6.0775 | 6.49 | 7.2975 |
| 54.9 | 5.8375 | 6.08 | 6.4925 | 7.3025 |
| 55.0 | 5.8375 | 6.08 | 6.495 | 7.3075 |
| 55.1 | 5.8375 | 6.0825 | 6.4975 | 7.31 |
| 55.2 | 5.84 | 6.0325 | 6.5 | 7.315 |
| 55.3 | 5.84 | 6.085 | 6.5025 | 7.32 |
| 55.4 | 5.8425 | 6.0875 | 6.505 | 7.3225 |
| 55.5 | 5.8425 | 6.0875 | 6.5075 | 7.3275 |
| 55.6 | 5.8425 | 6.09 | 6.51 | 7.3325 |
| 55.7 | 5.845 | 6.09 | 6.5125 | 7.3375 |
| 55.8 | 5.845 | 6.0925 | 6.515 | 7.34 |
| 55.9 | 5.8475 | 6.095 | 6.5175 | 7.345 |
| 56.0 | 5.8475 | 6.095 | 6.5175 | 7.35 |
| 56.1 | 5.8475 | 6.0975 | 6.52 | 7.3525 |
| 56.2 | 5.85 | 6.0975 | 6.5225 | 7.3575 |
| 56.3 | 5.85 | 6.1 | 6.525 | 7.3625 |
| 56.4 | 5.85 | 6.1025 | 6.5275 | 7.365 |
| 56.5 | 5.8525 | 6.1025 | 6.53 | 7.37 |
| 56.6 | 5.8525 | 6.105 | 6.5325 | 7.375 |
| 56.7 | 5.8525 | 6.105 | 6.535 | 7.3775 |
| 56.8 | 5.855 | 6.1075 | 6.5375 | 7.3825 |
| 56.9 | 5.855 | 6.1075 | 6.54 | 7.3875 |
| 57.0 | 5.855 | 6.11 | 6.5425 | 7.39 |
| 57.1 | 5.8575 | 6.11 | 6.545 | 7.395 |
| 57.2 | 5.8575 | 6.1125 | 6.5475 | 7.3975 |
| 57.3 | 5.8575 | 6.115 | 6.5475 | 7.4025 |
| 57.4 | 5.86 | 6.115 | 6.55 | 7.4075 |
| 57.5 | 5.86 | 6.1175 | 6.5525 | 7.41 |
| 57.6 | 5.86 | 6.1175 | 6.555 | 7.415 |
| 57.7 | 5.8625 | 6.12 | 6.5575 | 7.42 |
| 57.8 | 5.8625 | 6.12 | 6.56 | 7.4225 |
| 57.9 | 5.8625 | 6.1225 | 6.5625 | 7.4275 |
| 58.0 | 5.865 | 6.1225 | 6.565 | 7.43 |
| 58.1 | 5.865 | 6.125 | 6.565 | 7.435 |
| 58.2 | 5.865 | 6.125 | 6.5675 | 7.44 |
| 58.3 | 5.865 | 6.1275 | 6.57 | 7.4425 |
| 58.4 | 5.8675 | 6.1275 | 6.5725 | 7.4475 |
| 58.5 | 5.8675 | 6.13 | 6.575 | 7.45 |
| 58.6 | 5.8675 | 6.13 | 6.5775 | 7.455 |
| 58.7 | 5.87 | 6.1325 | 6.5775 | 7.4575 |
| 58.8 | 5.87 | 6.1325 | 6.58 | 7.4625 |
| 58.9 | 5.87 | 6.135 | 6.5825 | 7.4675 |
| 59.0 | 5.87 | 6.135 | 6.585 | 7.47 |
| 59.1 | 5.8725 | 6.135 | 6.5875 | 7.175 |
| 59.2 | 5.8725 | 6.1375 | 6.59 | 7.4775 |
| 59.3 | 5.8725 | 6.1375 | 6.59 | 7.4825 |
| 59.4 | 5.8725 | 6.14 | 6.5925 | 7.435 |
| 59.5 | 5.875 | 6.14 | 6.595 | 7.49 |

APPENDIX 2-continued

| Reverse Pressure lookup | | | | |
|---|---|---|---|---|
| | Temp | | | |
| | 17.2 C. | 20.1 C. | 25.1 C. | 35.1 C. |
| 59.6 | 5.875 | 6.1425 | 6.5975 | 7.4925 |
| 59.7 | 5.875 | 6.1425 | 6.6 | 7.4975 |
| 59.8 | 5.875 | 6.145 | 6.6 | 7.5 |
| 59.9 | 5.8775 | 6.145 | 6.6025 | 7.505 |
| 60.0 | 5.8775 | 6.145 | 6.605 | 7.5075 |
| 60.1 | 5.8775 | 6.1475 | 6.6075 | 7.5125 |
| 60.2 | 5.8775 | 6.1475 | 6.61 | 7.515 |
| 60.3 | 5.8775 | 6.15 | 6.61 | 7.52 |
| 60.4 | 5.88 | 6.15 | 6.6125 | 7.525 |
| 60.5 | 5.88 | 6.1525 | 6.615 | 7.5275 |
| 60.6 | 5.88 | 6.1525 | 6.6175 | 7.5325 |
| 60.7 | 5.88 | 6.1525 | 6.6175 | 7.535 |
| 60.8 | 5.8825 | 6.155 | 6.62 | 7.54 |
| 60.9 | 5.8825 | 6.155 | 6.6225 | 7.5425 |
| 61.0 | 5.8825 | 6.1575 | 6.625 | 7.545 |
| 61.1 | 5.8825 | 5.1575 | 6.6275 | 7.55 |
| 61.2 | 5.8825 | 5.1575 | 6.6275 | 7.5525 |
| 61.3 | 5.885 | 6.16 | 6.63 | 7.5575 |
| 61.4 | 5.885 | 6.16 | 6.6325 | 7.56 |
| 61.5 | 5.885 | 6.1625 | 6.635 | 7.565 |
| 61.6 | 5.885 | 6.1625 | 6.635 | 7.5675 |
| 61.7 | 5.885 | 6.1625 | 6.6375 | 7.5725 |
| 61.8 | 5.885 | 6.165 | 6.64 | 7.575 |
| 61.9 | 5.8875 | 6.165 | 6.64 | 7.58 |
| 62.0 | 5.8875 | 6.165 | 6.6425 | 7.5825 |
| 62.1 | 5.8875 | 6.1675 | 6.645 | 7.5875 |
| 62.2 | 5.8875 | 6.1675 | 6.6475 | 7.59 |
| 62.3 | 5.8875 | 6.17 | 6.6475 | 7.595 |
| 62.4 | 5.8875 | 6.17 | 6.65 | 7.5975 |
| 62.5 | 5.89 | 6.17 | 6.6525 | 7.6 |
| 62.6 | 5.89 | 6.1725 | 6.6525 | 7.605 |
| 62.7 | 5.89 | 6.1725 | 6.655 | 7.6075 |
| 62.8 | 5.89 | 6.1725 | 6.6575 | 7.6125 |
| 62.9 | 5.89 | 6.175 | 6.66 | 7.615 |
| 63.0 | 5.89 | 6.175 | 6.66 | 7.62 |
| 63.1 | 5.8925 | 6.175 | 6.6625 | 7.6225 |
| 63.2 | 5.8925 | 5.1775 | 6.665 | 7.6275 |
| 63.3 | 5.8925 | 6.1775 | 6.665 | 7.63 |
| 63.4 | 5.8925 | 6.1775 | 6.6675 | 7.6325 |
| 63.5 | 5.8925 | 6.18 | 6.67 | 7.6375 |
| 63.6 | 5.8925 | 6.18 | 6.67 | 7.64 |
| 63.7 | 5.8925 | 6.18 | 6.6725 | 7.645 |
| 63.8 | 5.895 | 6.1825 | 6.575 | 7.6475 |
| 63.9 | 5.895 | 6.1825 | 6.6775 | 7.65 |
| 64.0 | 5.895 | 6.1825 | 6.6775 | 7.655 |
| 64.1 | 5.895 | 6.185 | 6.68 | 7.6575 |
| 64.2 | 5.895 | 6.185 | 6.6825 | 7.5625 |
| 64.3 | 5.895 | 6.185 | 6.6825 | 7.665 |
| 64.4 | 5.895 | 6.1875 | 6.685 | 7.67 |
| 64.5 | 5.895 | 6.1875 | 6.6875 | 7.6725 |
| 64.6 | 5.8975 | 6.1875 | 6.6875 | 7.675 |
| 64.7 | 5.8975 | 6.19 | 6.69 | 7.68 |
| 64.8 | 5.8975 | 6.19 | 6.6925 | 7.6825 |
| 64.9 | 5.8975 | 6.19 | 6.6925 | 7.6875 |
| 65.0 | 5.8975 | 6.1925 | 6.695 | 7.69 |
| 65.1 | 5.8975 | 6.1925 | 6.6975 | 7.6925 |
| 65.2 | 5.8975 | 6.1925 | 6.6975 | 7.6975 |
| 65.3 | 5.8975 | 6.195 | 6.7 | 7.7 |
| 65.4 | 5.8975 | 6.195 | 6.7 | 7.7025 |
| 65.5 | 5.9 | 6.195 | 6.7025 | 7.7075 |
| 65.6 | 5.9 | 6.195 | 6.705 | 7.71 |
| 65.7 | 5.9 | 6.1975 | 6.705 | 7.715 |
| 65.8 | 5.9 | 6.1975 | 6.7075 | 7.7175 |
| 65.9 | 5.9 | 6.1975 | 6.71 | 7.72 |
| 66.0 | 5.9 | 6.2 | 6.71 | 7.725 |
| 66.1 | 5.9 | 6.2 | 6.7125 | 7.7275 |
| 66.2 | 5.9 | 6.2 | 6.715 | 7.73 |
| 66.3 | 5.9 | 6.2 | 6.715 | 7.735 |
| 66.4 | 5.9 | 6.2025 | 6.7175 | 7.7375 |
| 66.5 | 5.9025 | 6.2025 | 6.72 | 7.7425 |
| 66.6 | 5.9025 | 6.2025 | 6.72 | 7.745 |
| 66.7 | 5.9025 | 6.205 | 6.7225 | 7.7475 |
| 66.8 | 5.9025 | 6.205 | 6.7225 | 7.7525 |
| 66.9 | 5.9025 | 6.205 | 6.725 | 7.755 |

APPENDIX 2-continued

| Reverse Pressure lookup | | | | |
|---|---|---|---|---|
| | Temp | | | |
| | 17.2 C. | 20.1 C. | 25.1 C. | 35.1 C. |
| 67.0 | 5.9025 | 6.205 | 6.7275 | 7.7575 |
| 67.1 | 5.9025 | 6.2075 | 6.7275 | 7.7625 |
| 67.2 | 5.9025 | 6.2075 | 6.73 | 7.765 |
| 67.3 | 5.9025 | 6.2075 | 6.7325 | 7.77 |
| 67.4 | 5.9025 | 6.21 | 6.7325 | 7.7725 |
| 67.5 | 5.9025 | 6.21 | 6.735 | 7.775 |
| 67.6 | 5.9025 | 6.21 | 6.735 | 7.78 |
| 67.7 | 5.905 | 6.21 | 6.7375 | 7.7825 |
| 67.8 | 5.905 | 6.2125 | 6.74 | 7.785 |
| 67.9 | 5.905 | 6.2125 | 6.74 | 7.79 |
| 68.0 | 5.905 | 6.2125 | 6.7425 | 7.7925 |
| 68.1 | 5.905 | 6.2125 | 6.7425 | 7.795 |
| 68.2 | 5.905 | 6.215 | 6.745 | 7.5 |
| 68.3 | 5.905 | 6.215 | 6.7475 | 7.8025 |
| 68.4 | 5.905 | 6.215 | 6.7475 | 7.805 |
| 68.5 | 5.905 | 6.215 | 6.75 | 7.81 |
| 68.6 | 5.905 | 6.2175 | 6.75 | 7.8125 |
| 68.7 | 5.905 | 6.2175 | 6.7525 | 7.815 |
| 68.8 | 5.905 | 6.2175 | 6.755 | 7.82 |
| 68.9 | 5.905 | 6.22 | 6.755 | 7.3225 |
| 69.0 | 5.905 | 6.22 | 6.7575 | 7.825 |
| 69.1 | 5.9075 | 6.22 | 6.7575 | 7.83 |
| 69.2 | 5.9075 | 6.22 | 6.76 | 7.8325 |
| 69.3 | 5.9075 | 6.2225 | 5.7625 | 7.8375 |
| 69.4 | 5.9075 | 6.2225 | 6.7625 | 7.84 |
| 69.5 | 5.9075 | 6.2225 | 6.765 | 7.8425 |
| 69.6 | 5.9075 | 6.2225 | 6.765 | 7.8475 |
| 69.7 | 5.9075 | 6.225 | 6.7675 | 7.85 |
| 69.8 | 5.9075 | 6.225 | 6.77 | 7.8525 |
| 69.9 | 5.9075 | 6.225 | 6.77 | 7.8575 |
| 70.0 | 5.9075 | 6.225 | 6.7725 | 7.86 |
| 70.1 | 5.9075 | 6.2275 | 6.7725 | 7.8625 |
| 70.2 | 5.9075 | 6.2275 | 6.775 | 7.8675 |
| 70.3 | 5.9075 | 6.2275 | 6.7775 | 7.87 |
| 70.4 | 5.9975 | 6.2275 | 6.7775 | 7.8725 |
| 70.5 | 5.9075 | 6.2275 | 6.78 | 7.8775 |
| 70.6 | 5.9075 | 6.23 | 6.78 | 7.88 |
| 70.7 | 5.9075 | 6.23 | 6.7825 | 7.8825 |
| 70.8 | 5.9075 | 6.23 | 6.785 | 7.8375 |
| 70.9 | 5.91 | 6.23 | 6.785 | 7.89 |
| 71.0 | 5.91 | 6.2325 | 6.7875 | 7.8925 |
| 71.1 | 5.91 | 5.2325 | 6.7875 | 7.8975 |
| 71.2 | 5.91 | 6.2325 | 6.79 | 7.9 |
| 71.3 | 5.91 | 6.2325 | 6.79 | 7.9025 |
| 71.4 | 5.91 | 6.235 | 6.7925 | 7.9075 |
| 71.5 | 5.91 | 6.235 | 6.795 | 7.91 |
| 71.6 | 5.91 | 6.235 | 6.795 | 7.9125 |
| 71.7 | 5.91 | 6.235 | 6.7975 | 7.9175 |
| 71.8 | 5.91 | 6.2375 | 6.7975 | 7.92 |
| 71.9 | 5.91 | 6.2375 | 6.8 | 7.9225 |
| 72.0 | 5.91 | 6.2375 | 6.8025 | 7.9275 |
| 72.1 | 5.91 | 6.2375 | 6.8025 | 7.93 |
| 72.2 | 5.91 | 6.24 | 6.805 | 7.9325 |
| 72.3 | 5.91 | 6.24 | 6.805 | 7.9375 |
| 72.4 | 5.91 | 6.24 | 6.8075 | 7.941 |
| 72.5 | 5.91 | 6.24 | 6.8075 | 7.9425 |
| 72.6 | 5.91 | 5.24 | 6.81 | 7.9475 |
| 72.7 | 5.91 | 6.2425 | 6.8125 | 7.95 |
| 72.8 | 5.91 | 6.2425 | 6.8125 | 7.9525 |
| 72.9 | 5.91 | 6.2425 | 6.815 | 7.9575 |
| 73.0 | 5.9125 | 6.2425 | 6.815 | 7.96 |
| 73.1 | 5.9125 | 6.245 | 6.8175 | 7.9625 |
| 73.2 | 5.9125 | 6.245 | 6.82 | 7.9675 |
| 73.3 | 5.9125 | 6.245 | 6.82 | 7.97 |
| 73.4 | 5.9125 | 6.245 | 6.8225 | 7.9726 |
| 73.5 | 5.9125 | 6.2475 | 6.8225 | 7.9775 |
| 73.6 | 5.9125 | 6.2475 | 6.825 | 7.98 |
| 73.7 | 5.9125 | 6.2475 | 6.825 | 7.9825 |
| 73.8 | 5.9125 | 6.2475 | 6.8275 | 7.9875 |
| 73.9 | 5.9125 | 6.2475 | 6.83 | 7.99 |
| 74.0 | 5.9125 | 6.25 | 6.83 | 7.995 |
| 74.1 | 5.9125 | 6.25 | 6.8325 | 7.9975 |
| 74.2 | 5.9125 | 6.25 | 6.8325 | 8 |
| 74.3 | 5.9125 | 6.25 | 6.835 | 8.005 |

APPENDIX 2-continued

Reverse Pressure lookup

| | Temp | | | |
|---|---|---|---|---|
| | 17.2 C. | 20.1 C. | 25.1 C. | 35.1 C. |
| 74.4 | 5.9125 | 6.2525 | 6.835 | 8.0075 |
| 74.5 | 5.9125 | 6.2525 | 6.8375 | 8.01 |
| 74.6 | 5.9125 | 6.2525 | 6.84 | 8.015 |
| 74.7 | 5.9125 | 6.2525 | 6.84 | 8.0175 |
| 74.8 | 5.9125 | 6.255 | 6.8425 | 8.02 |
| 74.9 | 5.9125 | 6.255 | 6.8425 | 8.025 |
| 75.0 | 5.9125 | 6.255 | 6.845 | 8.0275 |
| 75.1 | 5.9125 | 6.255 | 6.8475 | 8.03 |
| 75.2 | 5.9125 | 6.255 | 6.8475 | 8.035 |
| 75.3 | 5.9125 | 6.2575 | 6.85 | 8.0375 |
| 75.4 | 5.9125 | 6.2575 | 6.85 | 8.04 |
| 75.5 | 5.915 | 6.2575 | 6.8525 | 8.045 |
| 75.6 | 5.915 | 6.2575 | 6.8525 | 8.0475 |
| 75.7 | 5.915 | 6.26 | 6.855 | 8.0525 |
| 75.8 | 5.915 | 6.26 | 6.8575 | 8.055 |
| 75.9 | 5.915 | 6.26 | 6.8575 | 8.0575 |
| 76.0 | 5.915 | 6.26 | 6.86 | 8.0625 |
| 76.1 | 5.915 | 6.2625 | 6.86 | 8.065 |
| 76.2 | 5.915 | 6.2625 | 6.8625 | 8.0675 |
| 76.3 | 5.915 | 6.2625 | 6.865 | 8.0725 |
| 76.4 | 5.915 | 6.2625 | 6.865 | 8.075 |
| 76.5 | 5.915 | 6.2625 | 6.8675 | 8.08 |
| 76.6 | 5.915 | 6.265 | 6.8675 | 8.0825 |
| 76.7 | 5.915 | 5.265 | 6.87 | 8.085 |
| 76.8 | 5.915 | 6.265 | 6.8725 | 8.09 |
| 76.9 | 5.915 | 6.265 | 6.8725 | 8.0925 |
| 77.0 | 5.915 | 6.2575 | 6.875 | 8.095 |
| 77.1 | 5.915 | 6.2675 | 6.875 | 8.1 |
| 77.2 | 5.915 | 6.2675 | 6.8775 | 8.1025 |
| 77.3 | 5.915 | 6.2675 | 6.8775 | 8.1075 |
| 77.4 | 5.915 | 6.27 | 6.88 | 8.11 |
| 77.5 | 5.915 | 6.27 | 6.8825 | 8.1125 |
| 77.6 | 5.915 | 6.27 | 6.8825 | 8.1175 |
| 77.7 | 5.915 | 6.27 | 6.885 | 8.12 |
| 77.8 | 5.915 | 6.27 | 6.885 | 8.125 |
| 77.9 | 5.915 | 6.2725 | 6.8875 | 8.1275 |
| 78.0 | 5.9175 | 6.2725 | 6.89 | 8.13 |
| 76.1 | 5.9175 | 6.2725 | 6.89 | 8.135 |
| 78.2 | 5.9175 | 6.2725 | 6.8925 | 8.1375 |
| 78.3 | 5.9175 | 6.275 | 6.8925 | 8.1425 |
| 78.4 | 5.9175 | 6.275 | 6.895 | 8.145 |
| 78.5 | 5.9175 | 6.275 | 6.8975 | 8.1475 |
| 78.6 | 5.9175 | 6.275 | 6.8975 | 8.1525 |
| 78.7 | 5.9175 | 6.2775 | 6.9 | 8.155 |
| 78.8 | 5.9175 | 6.2775 | 6.9025 | 8.16 |
| 78.9 | 5.9175 | 6.2775 | 6.9025 | 8.1625 |
| 79.0 | 5.9175 | 6.2775 | 6.905 | 8.1675 |
| 79.1 | 5.9175 | 6.28 | 6.905 | 8.17 |
| 79.2 | 5.9175 | 6.28 | 6.9075 | 8.1725 |
| 79.3 | 5.9175 | 6.28 | 6.91 | 8.1775 |
| 79.4 | 5.9175 | 6.28 | 6.91 | 8.18 |
| 79.5 | 5.9175 | 6.2825 | 6.9125 | 8.185 |
| 79.6 | 5.9175 | 6.2825 | 6.9125 | 8.1875 |
| 79.7 | 5.9175 | 6.2825 | 6.915 | 8.1925 |
| 79.8 | 5.9175 | 6.2825 | 6.9175 | 8.195 |
| 79.9 | 5.9175 | 6.285 | 6.9175 | 8.2 |
| 80.0 | 5.9175 | 6.285 | 6.92 | 8.2025 |
| 80.1 | 5.9175 | 6.285 | 6.9225 | 8.205 |
| 80.2 | 5.9175 | 6.285 | 6.9225 | 8.21 |
| 80.3 | 5.92 | 6.2875 | 6.925 | 8.2125 |
| 80.4 | 5.92 | 6.2875 | 6.925 | 8.2175 |
| 80.5 | 5.92 | 6.2875 | 6.9275 | 8.22 |
| 80.6 | 5.92 | 6.2875 | 6.93 | 8.225 |
| 80.7 | 5.92 | 6.29 | 6.93 | 8.2275 |
| 80.8 | 5.92 | 6.29 | 6.9325 | 8.2325 |
| 80.9 | 5.92 | 6.29 | 6.935 | 8.235 |
| 81.0 | 5.92 | 6.29 | 6.935 | 8.24 |
| 81.1 | 5.92 | 6.2925 | 6.9375 | 8.2425 |
| 81.2 | 5.92 | 6.2925 | 6.94 | 8.2475 |
| 81.3 | 5.92 | 6.2925 | 6.94 | 8.25 |
| 81.4 | 5.92 | 6.2925 | 6.9425 | 8.255 |
| 81.5 | 5.92 | 6.295 | 6.9425 | 8.2575 |
| 81.6 | 5.92 | 6.295 | 6.945 | 8.2625 |
| 81.7 | 5.92 | 6.295 | 6.9475 | 8.265 |

APPENDIX 2-continued

Reverse Pressure lookup

| | Temp | | | |
|---|---|---|---|---|
| | 17.2 C. | 20.1 C. | 25.1 C. | 35.1 C. |
| 81.8 | 5.92 | 6.295 | 6.9475 | 8.27 |
| 81.9 | 5.92 | 6.2975 | 6.95 | 8.2725 |
| 82.0 | 5.92 | 6.2975 | 6.9525 | 8.2775 |
| 82.1 | 5.92 | 6.2975 | 6.9525 | 8.28 |
| 82.2 | 5.9225 | 6.2975 | 6.955 | 8.285 |
| 82.3 | 5.9225 | 6.3 | 6.9575 | 8.2875 |
| 82.4 | 5.9225 | 3.3 | 6.9575 | 8.2925 |
| 82.5 | 5.9225 | 6.3 | 6.96 | 8.295 |
| 82.6 | 5.9225 | 6.3025 | 6.9625 | 8.3 |
| 82.7 | 5.9225 | 6.3025 | 6.9625 | 8.3025 |
| 82.8 | 5.9225 | 6.3025 | 6.965 | 8.3075 |
| 82.9 | 5.9225 | 6.3025 | 6.9675 | 8.3125 |
| 83.0 | 5.9225 | 6.305 | 6.9675 | 8.315 |
| 83.1 | 5.9225 | 6.305 | 6.97 | 8.32 |
| 83.2 | 5.9225 | 6.305 | 6.9725 | 8.3225 |
| 83.3 | 5.9225 | 6.305 | 6.9725 | 8.3275 |
| 83.4 | 5.9225 | 6.3075 | 6.975 | 8.33 |
| 83.5 | 5.9225 | 6.3075 | 6.9775 | 8.335 |
| 83.6 | 5.9225 | 6.3075 | 6.98 | 8.34 |
| 83.7 | 5.9225 | 6.31 | 6.98 | 8.3425 |
| 83.8 | 5.925 | 6.31 | 6.9825 | 8.3475 |
| 83.9 | 5.925 | 6.31 | 6.985 | 8.35 |
| 84.0 | 5.925 | 6.31 | 6.985 | 8.355 |
| 84.1 | 5.925 | 6.3125 | 6.9875 | 8.3575 |
| 84.2 | 5.925 | 6.3125 | 6.99 | 8.3625 |
| 84.3 | 5.925 | 6.3125 | 6.99 | 8.3675 |
| 84.4 | 5.925 | 6.315 | 6.9925 | 8.37 |
| 84.5 | 5.925 | 6.315 | 6.995 | 8.375 |
| 84.6 | 5.925 | 6.315 | 6.9975 | 8.38 |
| 84.7 | 5.925 | 6.3175 | 6.9975 | 8.3825 |
| 84.8 | 5.925 | 6.3175 | 7 | 8.3875 |
| 84.9 | 5.925 | 6.3175 | 7.0025 | 8.39 |
| 85.0 | 5.925 | 6.32 | 7.0025 | 8.395 |
| 85.1 | 5.9275 | 6.32 | 7.005 | 8.4 |
| 85.2 | 5.9275 | 6.32 | 7.0075 | 8.4025 |
| 85.3 | 5.9275 | 6.32 | 7.01 | 8.4075 |
| 85.4 | 5.9275 | 6.3225 | 7.01 | 8.4125 |
| 85.5 | 5.9275 | 6.3225 | 7.0125 | 8.415 |
| 85.6 | 5.9275 | 6.3225 | 7.015 | 8.42 |
| 85.7 | 5.9275 | 6.325 | 7.0175 | 8.425 |
| 85.8 | 5.9275 | 5.325 | 7.0175 | 8.4275 |
| 85.9 | 5.9275 | 6.325 | 7.02 | 8.4325 |
| 86.0 | 5.9275 | 6.3275 | 7.0225 | 8.4375 |
| 86.1 | 5.9275 | 6.3275 | 7.025 | 8.44 |
| 86.2 | 5.93 | 6.3275 | 7.025 | 8.445 |
| 86.3 | 5.93 | 6.33 | 7.0275 | 8.45 |
| 86.4 | 5.93 | 6.33 | 7.03 | 8.455 |
| 86.5 | 5.93 | 6.33 | 7.0325 | 8.4575 |
| 86.6 | 5.93 | 6.3325 | 7.0325 | 8.4625 |
| 86.7 | 5.93 | 6.3325 | 7.035 | 8.4675 |
| 86.8 | 5.93 | 6.3325 | 7.0375 | 8.4725 |
| 86.9 | 5.93 | 6.335 | 7.04 | 8.475 |
| 87.0 | 5.93 | 6.335 | 7.0425 | 8.48 |
| 87.1 | 5.9325 | 6.335 | 7.0425 | 8.485 |
| 87.2 | 5.9325 | 6.3375 | 7.045 | 8.49 |
| 87.3 | 5.9325 | 6.3375 | 7.0475 | 8.4925 |
| 87.4 | 5.9325 | 6.34 | 7.05 | 8.4975 |
| 87.5 | 5.9325 | 6.34 | 7.0525 | 8.5025 |
| 87.6 | 5.9325 | 6.34 | 7.0525 | 8.5075 |
| 87.7 | 5.9325 | 6.3425 | 7.055 | 8.51 |
| 87.8 | 5.9325 | 6.3425 | 7.0575 | 8.515 |
| 87.9 | 5.9325 | 6.3425 | 7.06 | 8.52 |
| 88.0 | 5.935 | 6.345 | 7.0625 | 8.525 |
| 88.1 | 5.935 | 6.345 | 7.065 | 8.53 |
| 88.2 | 5.935 | 6.345 | 7.065 | 8.5325 |
| 88.3 | 5.935 | 6.3475 | 7.0675 | 8.5375 |
| 88.4 | 5.935 | 6.3475 | 7.07 | 8.5425 |
| 88.5 | 5.935 | 6.35 | 7.0725 | 8.5475 |
| 88.6 | 5.935 | 6.35 | 7.075 | 8.5525 |
| 88.7 | 5.9375 | 6.35 | 7.0775 | 8.5575 |
| 88.8 | 5.9375 | 6.3525 | 7.03 | 8.5625 |
| 88.9 | 5.9375 | 6.3525 | 7.08 | 8.565 |
| 89.0 | 5.9375 | 6.355 | 7.0825 | 8.57 |
| 89.1 | 5.9375 | 6.355 | 7.085 | 8.575 |

APPENDIX 2-continued

| Reverse Pressure lookup | | | | |
|---|---|---|---|---|
| | Temp | | | |
| | 17.2 C. | 20.1 C. | 25.1 C. | 35.1 C. |
| 89.2 | 5.9375 | 6.355 | 7.0875 | 8.58 |
| 89.3 | 5.9375 | 6.3575 | 7.09 | 8.535 |
| 89.4 | 5.94 | 6.3575 | 7.0925 | 8.59 |
| 89.5 | 5.94 | 6.36 | 7.095 | 8.595 |
| 89.6 | 5.94 | 6.36 | 7.0975 | 8.6 |
| 89.7 | 5.94 | 6.3625 | 7.1 | 8.605 |
| 89.8 | 5.94 | 6.3625 | 7.1 | 8.61 |
| 89.9 | 5.94 | 6.3625 | 7.1025 | 8.615 |
| 90.0 | 5.9425 | 6.365 | 7.105 | 8.6175 |
| 90.1 | 5.9425 | 6.365 | 7.1075 | 8.625 |
| 90.2 | 5.9425 | 6.3675 | 7.11 | 8.6275 |
| 90.3 | 5.9425 | 6.3675 | 7.1125 | 8.6325 |
| 90.4 | 5.9425 | 6.37 | 7.115 | 8.6375 |
| 90.5 | 5.9425 | 6.37 | 7.1175 | 8.6425 |
| 90.6 | 5.945 | 6.37 | 7.12 | 8.6475 |
| 90.7 | 5.945 | 6.3725 | 7.1225 | 8.6525 |
| 90.8 | 5.945 | 6.3725 | 7.125 | 8.6575 |
| 90.9 | 5.945 | 6.375 | 7.1275 | 8.6625 |
| 91.0 | 5.945 | 6.375 | 7.13 | 8.6675 |
| 91.1 | 5.9475 | 6.3775 | 7.1325 | 8.675 |
| 91.2 | 5.9475 | 6.3775 | 7.135 | 8.68 |
| 91.3 | 5.9475 | 6.38 | 7.1375 | 8.685 |
| 91.4 | 5.9475 | 6.38 | 7.14 | 8.69 |
| 91.5 | 5.9475 | 6.3825 | 7.1425 | 8.695 |
| 91.6 | 5.95 | 6.3825 | 7.145 | 8.7 |
| 91.7 | 5.95 | 6.385 | 7.1475 | 8.705 |
| 91.8 | 5.95 | 6.385 | 7.15 | 8.71 |
| 91.9 | 5.95 | 6.3875 | 7.1525 | 8.715 |
| 92.0 | 5.9525 | 6.3875 | 7.155 | 8.72 |
| 92.1 | 5.9525 | 6.39 | 7.1575 | 8.725 |
| 92.2 | 5.9525 | 6.39 | 7.16 | 8.7325 |
| 92.3 | 5.9525 | 6.3925 | 7.1625 | 8.7375 |
| 92.4 | 5.9525 | 6.3925 | 7.165 | 8.7425 |
| 92.5 | 5.955 | 6.395 | 7.1675 | 8.7475 |
| 92.6 | 5.955 | 6.3975 | 7.17 | 8.7525 |
| 92.7 | 5.955 | 6.3975 | 7.1725 | 8.7575 |
| 92.8 | 5.955 | 6.4 | 7.175 | 8.7625 |
| 92.9 | 5.9575 | 6.4 | 7.1775 | 8.77 |
| 93.0 | 5.9575 | 6.4025 | 7.18 | 8.775 |
| 93.1 | 5.9575 | 6.4025 | 7.1825 | 8.78 |
| 93.2 | 5.96 | 6.405 | 7.1875 | 8.785 |
| 93.3 | 5.96 | 6.405 | 7.19 | 8.7925 |
| 93.4 | 5.96 | 6.4075 | 7.1925 | 8.7975 |
| 93.5 | 5.96 | 6.41 | 7.195 | 8.8025 |
| 93.6 | 5.9625 | 6.41 | 7.1975 | 8.8075 |
| 93.7 | 5.9625 | 6.4125 | 7.2 | 8.815 |
| 93.8 | 5.9625 | 6.4125 | 7.2025 | 8.82 |
| 93.9 | 5.965 | 6.415 | 7.2075 | 8.825 |
| 94.0 | 5.965 | 6.4175 | 7.21 | 8.8325 |
| 94.1 | 5.965 | 6.4175 | 7.2125 | 8.8375 |
| 94.2 | 5.9675 | 6.42 | 7.215 | 8.8425 |
| 94.3 | 5.9675 | 6.4225 | 7.2175 | 8.85 |
| 94.4 | 5.9675 | 6.4225 | 7.22 | 8.855 |
| 94.5 | 5.9675 | 6.425 | 7.225 | 8.86 |
| 94.6 | 5.97 | 6.425 | 7.2275 | 8.8675 |
| 94.7 | 5.97 | 6.4275 | 7.23 | 8.8725 |
| 94.8 | 5.9725 | 6.43 | 7.2325 | 8.8775 |
| 94.9 | 5.9725 | 6.43 | 7.2375 | 8.885 |
| 95.0 | 5.9725 | 6.4325 | 7.24 | 8.89 |
| 95.1 | 5.975 | 6.435 | 7.2425 | 8.8975 |
| 95.2 | 5.975 | 6.435 | 7.245 | 8.9025 |
| 95.3 | 5.975 | 6.4375 | 7.2475 | 8.9075 |
| 95.4 | 5.9775 | 6.44 | 7.2525 | 8.915 |
| 95.5 | 5.9775 | 6.4425 | 7.255 | 8.92 |
| 95.6 | 5.9775 | 6.4425 | 7.2575 | 8.9275 |
| 95.7 | 5.98 | 6.445 | 7.2625 | 8.9325 |
| 95.8 | 5.98 | 6.4475 | 7.265 | 8.94 |
| 95.9 | 5.9325 | 6.4475 | 7.2675 | 8.945 |
| 96.0 | 5.9825 | 6.45 | 7.2725 | 8.9525 |
| 96.1 | 5.9825 | 6.4525 | 7.275 | 8.96 |
| 96.2 | 5.985 | 6.455 | 7.2775 | 8.965 |
| 96.3 | 5.985 | 6.455 | 7.2325 | 8.9725 |
| 96.4 | 5.9875 | 6.4575 | 7.285 | 8.9775 |
| 96.5 | 5.9875 | 6.46 | 7.2875 | 8.9135 |

APPENDIX 2-continued

| Reverse Pressure lookup | | | | |
|---|---|---|---|---|
| | Temp | | | |
| | 17.2 C. | 20.1 C. | 25.1 C. | 35.1 C. |
| 96.6 | 5.99 | 6.4625 | 7.2925 | 8.99 |
| 96.7 | 5.99 | 6.465 | 7.295 | 8.9975 |
| 96.8 | 5.9925 | 6.465 | 7.3 | 9 |

APPENDIX 3

| Lookup mass as function of dP (inside) | | | | | |
|---|---|---|---|---|---|
| | | Delta T | | | |
| | | 5 C. Delta | 10 C. Delta | 15 C. Delta | 18 C. Delta |
| mass | 30.0 | 0.1925 | 0.3775 | 0.57 | |
| | 30.1 | 0.1925 | 0.3825 | 0.575 | |
| | 30.2 | 0.1925 | 0.3825 | 0.575 | |
| | 30.3 | 0.195 | 0.3825 | 0.5775 | |
| | 30.4 | 0.195 | 0.3850 | 0.58 | |
| | 30.5 | 0.1975 | 0.3850 | 0.5825 | |
| | 30.6 | 0.195 | 0.3900 | 0.585 | |
| | 30.7 | 0.1975 | 0.3900 | 0.5875 | |
| | 30.8 | 0.1975 | 0.3925 | 0.59 | |
| | 30.9 | 0.2 | 0.3925 | 0.5925 | |
| | 31.0 | 0.2 | 0.3950 | 0.595 | |
| | 31.1 | 0.2025 | 0.3950 | 0.5975 | |
| | 31.2 | 0.2025 | 0.3975 | 0.6 | |
| | 31.3 | 0.2025 | 0.3975 | 0.6 | |
| | 31.4 | 0.2025 | 0.4000 | 0.6025 | |
| | 31.5 | 0.2025 | 0.4025 | 0.605 | 0.725 |
| | 31.6 | 0.205 | 0.4050 | 0.61 | 0.73 |
| | 31.7 | 0.205 | 0.4075 | 0.6125 | 0.7325 |
| | 31.8 | 0.2075 | 0.4075 | 0.615 | 0.7375 |
| | 31.9 | 0.2075 | 0.4075 | 0.615 | 0.7375 |
| | 32.0 | 0.2075 | 0.4100 | 0.6175 | 0.74 |
| | 32.1 | 0.21 | 0.4100 | 0.62 | 0.7425 |
| | 32.2 | 0.21 | 0.4125 | 0.6225 | 0.745 |
| | 32.3 | 0.21 | 0.4150 | 0.625 | 0.75 |
| | 32.4 | 0.21 | 0.4175 | 0.6275 | 0.7525 |
| | 32.5 | 0.2125 | 0.4175 | 0.63 | 0.755 |
| | 32.6 | 0.215 | 0.4200 | 0.635 | 0.76 |
| | 32.7 | 0.215 | 0.4225 | 0.6375 | 0.7625 |
| | 32.8 | 0.215 | 0.4250 | 0.64 | 0.765 |
| | 32.9 | 0.215 | 0.4250 | 0.64 | 0.7675 |
| | 33.0 | 0.2175 | 0.4250 | 0.6425 | 0.77 |
| | 33.1 | 0.2175 | 0.4275 | 0.645 | 0.7725 |
| | 33.2 | 0.2175 | 0.4300 | 0.6475 | 0.7775 |
| | 33.3 | 0.22 | 0.4325 | 0.6525 | 0.78 |
| | 33.4 | 0.22 | 0.4325 | 0.6525 | 0.7825 |
| | 33.5 | 0.22 | 0.4350 | 0.655 | 0.785 |
| | 33.6 | 0.22 | 0.4375 | 0.6575 | 0.7875 |
| | 33.7 | 0.2225 | 0.4400 | 0.6625 | 0.7925 |
| | 33.8 | 0.2225 | 0.4400 | 0.6625 | 0.7925 |
| | 33.9 | 0.2225 | 0.4425 | 0.665 | 0.7975 |
| | 34.0 | 0.225 | 0.4450 | 0.67 | 0.8 |
| | 34.1 | 0.225 | 0.4450 | 0.67 | 0.8025 |
| | 34.2 | 0.225 | 0.4475 | 0.6725 | 0.805 |
| | 34.3 | 0.2275 | 0.4500 | 0.6775 | 0.81 |
| | 34.4 | 0.2275 | 0.4500 | 0.6775 | 0.8125 |
| | 34.5 | 0.2275 | 0.4525 | 0.68 | 0.815 |
| | 34.6 | 0.23 | 0.4525 | 0.6825 | 0.8175 |
| | 34.7 | 0.23 | 0.4550 | 0.685 | 0.82 |
| | 34.8 | 0.2325 | 0.4575 | 0.69 | 0.825 |
| | 34.9 | 0.2325 | 0.4575 | 0.69 | 0.8275 |
| | 35.0 | 0.235 | 0.4600 | 0.695 | 0.83 |
| | 35.1 | 0.235 | 0.4600 | 0.695 | 0.8325 |
| | 35.2 | 0.2375 | 0.4625 | 0.7 | 0.8375 |
| | 35.3 | 0.235 | 0.4650 | 0.7 | 0.84 |
| | 35.4 | 0.2375 | 0.4675 | 0.705 | 0.8425 |
| | 35.5 | 0.2375 | 0.4675 | 0.705 | 0.845 |
| | 35.6 | 0.24 | 0.4700 | 0.71 | 0.85 |
| | 35.7 | 0.24 | 0.4700 | 0.71 | 0.85 |
| | 35.8 | 0.24 | 0.4725 | 0.7125 | 0.8525 |

APPENDIX 3-continued

| Lookup mass as function of dP (inside) | | | | |
|---|---|---|---|---|
| | Delta T | | | |
| | 5 C. Delta | 10 C. Delta | 15 C. Delta | 18 C. Delta |
| 35.9 | 0.24 | 0.4750 | 0.715 | 0.8575 |
| 36.0 | 0.2425 | 0.4750 | 0.7175 | 0.86 |
| 36.1 | 0.245 | 0.4775 | 0.7225 | 0.865 |
| 36.2 | 0.2425 | 0.4800 | 0.7225 | 0.8675 |
| 36.3 | 0.245 | 0.4800 | 0.725 | 0.8675 |
| 36.4 | 0.2475 | 0.4825 | 0.73 | 0.8725 |
| 36.5 | 0.245 | 0.4850 | 0.73 | 0.875 |
| 36.6 | 0.2475 | 0.4850 | 0.7325 | 0.8775 |
| 36.7 | 0.25 | 0.4875 | 0.7375 | 0.8825 |
| 36.8 | 0.2475 | 0.4900 | 0.7375 | 0.885 |
| 36.9 | 0.25 | 0.4900 | 0.74 | 0.8875 |
| 37.0 | 0.2525 | 0.4925 | 0.745 | 0.8925 |
| 37.1 | 0.2525 | 0.4950 | 0.7475 | 0.895 |
| 37.2 | 0.2525 | 0.4950 | 0.7475 | 0.8975 |
| 37.3 | 0.2525 | 0.4975 | 0.75 | 0.9 |
| 37.4 | 0.255 | 0.5000 | 0.755 | 0.905 |
| 37.5 | 0.255 | 0.5025 | 0.7575 | 0.9075 |
| 37.6 | 0.2575 | 0.5025 | 0.76 | 0.91 |
| 37.7 | 0.255 | 0.5050 | 0.76 | 0.9125 |
| 37.8 | 0.2575 | 0.5050 | 0.7625 | 0.915 |
| 37.9 | 0.2575 | 0.5100 | 0.7675 | 0.92 |
| 38.0 | 0.26 | 0.5100 | 0.77 | 0.9225 |
| 38.1 | 0.26 | 0.5125 | 0.7725 | 0.925 |
| 38.2 | 0.2625 | 0.5125 | 0.775 | 0.9275 |
| 38.3 | 0.2625 | 0.5150 | 0.7775 | 0.93 |
| 38.4 | 0.265 | 0.5150 | 0.78 | 0.9325 |
| 38.5 | 0.265 | 0.5175 | 0.7825 | 0.9375 |
| 38.6 | 0.265 | 0.5200 | 0.785 | 0.94 |
| 38.7 | 0.265 | 0.5225 | 0.7875 | 0.945 |
| 38.8 | 0.265 | 0.5250 | 0.79 | 0.9475 |
| 38.9 | 0.2675 | 0.5250 | 0.7925 | 0.95 |
| 39.0 | 0.2675 | 0.5275 | 0.795 | 0.9525 |
| 39.1 | 0.2675 | 0.5300 | 0.7975 | 0.9575 |
| 39.2 | 0.27 | 0.5300 | 0.8 | 0.96 |
| 39.3 | 0.2725 | 0.5325 | 0.805 | 0.9625 |
| 39.4 | 0.2725 | 0.5350 | 0.8075 | 0.965 |
| 39.5 | 0.275 | 0.5350 | 0.81 | 0.97 |
| 39.6 | 0.275 | 0.5375 | 0.8125 | 0.9725 |
| 39.7 | 0.275 | 0.5400 | 0.815 | 0.975 |
| 39.8 | 0.275 | 0.5425 | 0.8175 | 0.98 |
| 39.9 | 0.2775 | 0.5425 | 0.82 | 0.9825 |
| 40.0 | 0.2775 | 0.5425 | 0.82 | 0.9825 |
| 40.1 | 0.2775 | 0.5450 | 0.8225 | 0.9875 |
| 40.2 | 0.2775 | 0.5475 | 0.825 | 0.99 |
| 40.3 | 0.28 | 0.5500 | 0.83 | 0.9925 |
| 40.4 | 0.2825 | 0.5500 | 0.8325 | 0.9975 |
| 40.5 | 0.2825 | 0.5525 | 0.835 | 1 |
| 40.6 | 0.2825 | 0.5550 | 0.8375 | 1.0025 |
| 40.7 | 0.2825 | 0.5575 | 0.84 | 1.0075 |
| 40.8 | 0.2825 | 0.5575 | 0.84 | 1.0075 |
| 40.9 | 0.285 | 0.5600 | 0.845 | 1.0125 |
| 41.0 | 0.2875 | 0.5600 | 0.8475 | 1.015 |
| 41.1 | 0.2875 | 0.5625 | 0.85 | 1.02 |
| 41.2 | 0.2875 | 0.5650 | 0.8525 | 1.0225 |
| 41.3 | 0.29 | 0.5650 | 0.855 | 1.025 |
| 41.4 | 0.29 | 0.5675 | 0.8575 | 1.0275 |
| 41.5 | 0.29 | 0.5700 | 0.86 | 1.0325 |
| 41.6 | 0.2925 | 0.5725 | 0.865 | 1.035 |
| 41.7 | 0.2925 | 0.5750 | 0.8675 | 1.04 |
| 41.8 | 0.2925 | 0.5750 | 0.8675 | 1.04 |
| 41.9 | 0.295 | 0.5775 | 0.8725 | 1.045 |
| 42.0 | 0.295 | 0.5800 | 0.875 | 1.0475 |
| 42.1 | 0.295 | 0.5800 | 0.875 | 1.05 |
| 42.2 | 0.2975 | 0.5825 | 0.88 | 1.0525 |
| 42.3 | 0.2975 | 0.5850 | 0.8825 | 1.0575 |
| 42.4 | 0.2975 | 0.5850 | 0.8825 | 1.06 |
| 42.5 | 0.3 | 0.5875 | 0.8875 | 1.0625 |
| 42.6 | 0.3 | 0.5900 | 0.89 | 1.0675 |
| 42.7 | 0.3025 | 0.5900 | 0.8925 | 1.0675 |
| 42.8 | 0.3025 | 0.5925 | 0.895 | 1.0725 |
| 42.9 | 0.305 | 0.5950 | 0.9 | 1.0775 |
| 43.0 | 0.305 | 0.5950 | 0.9 | 1.0775 |
| 43.1 | 0.305 | 0.5975 | 0.9025 | 1.0825 |
| 43.2 | 0.305 | 0.6000 | 0.905 | 1.085 |

APPENDIX 3-continued

| Lookup mass as function of dP (inside) | | | | |
|---|---|---|---|---|
| | Delta T | | | |
| | 5 C. Delta | 10 C. Delta | 15 C. Delta | 18 C. Delta |
| 43.3 | 0.305 | 0.6025 | 0.9075 | 1.09 |
| 43.4 | 0.3075 | 0.6050 | 0.9125 | 1.0925 |
| 43.5 | 0.3075 | 0.6050 | 0.9125 | 1.095 |
| 43.6 | 0.31 | 0.6075 | 0.9175 | 1.1 |
| 43.7 | 0.31 | 0.6075 | 0.9175 | 1.1 |
| 43.8 | 0.3125 | 0.6100 | 0.9225 | 1.105 |
| 43.9 | 0.3125 | 0.6125 | 0.925 | 1.1075 |
| 44.0 | 0.3125 | 0.6150 | 0.9275 | 1.1125 |
| 44.1 | 0.315 | 0.6150 | 0.93 | 1.1125 |
| 44.2 | 0.315 | 0.6175 | 0.9325 | 1.1175 |
| 44.3 | 0.3175 | 0.6175 | 0.935 | 1.12 |
| 44.4 | 0.315 | 0.6225 | 0.9375 | 1.125 |
| 44.5 | 0.3175 | 0.6225 | 0.94 | 1.1275 |
| 44.6 | 0.32 | 0.6250 | 0.945 | 1.1325 |
| 44.7 | 0.32 | 0.6250 | 0.945 | 1.1325 |
| 44.8 | 0.32 | 0.6300 | 0.95 | 1.1375 |
| 44.9 | 0.32 | 0.6300 | 0.95 | 1.14 |
| 45.0 | 0.3225 | 0.6300 | 0.9525 | 1.1425 |
| 45.1 | 0.3225 | 0.6350 | 0.9575 | 1.1475 |
| 45.2 | 0.3225 | 0.6350 | 0.9575 | 1.15 |
| 45.3 | 0.325 | 0.6375 | 0.9625 | 1.155 |
| 45.4 | 0.3275 | 0.6375 | 0.965 | 1.155 |
| 45.5 | 0.3275 | 0.6400 | 0.9675 | 1.1575 |
| 45.6 | 0.3275 | 0.6425 | 0.97 | 1.1625 |
| 45.7 | 0.33 | 0.6425 | 0.9725 | 1.165 |
| 45.8 | 0.33 | 0.6475 | 0.9775 | 1.17 |
| 45.9 | 0.33 | 0.6475 | 0.9775 | 1.1725 |
| 46.0 | 0.33 | 0.6500 | 0.98 | 1.175 |
| 46.1 | 0.3325 | 0.6525 | 0.985 | 1.18 |
| 46.2 | 0.335 | 0.6525 | 0.9875 | 1.1825 |
| 46.3 | 0.3325 | 0.6550 | 0.9875 | 1.185 |
| 46.4 | 0.335 | 0.6550 | 0.99 | 1.1875 |
| 46.5 | 0.335 | 0.6600 | 0.995 | 1.1925 |
| 46.6 | 0.3375 | 0.6600 | 0.9975 | 1.195 |
| 46.7 | 0.34 | 0.6600 | 1 | 1.1975 |
| 46.8 | 0.3375 | 0.6650 | 1.0025 | 1.2025 |
| 46.9 | 0.34 | 0.6650 | 1.005 | 1.205 |
| 47.0 | 0.34 | 0.6675 | 1.0075 | 1.2075 |
| 47.1 | 0.3425 | 0.6675 | 1.01 | 1.21 |
| 47.2 | 0.3425 | 0.6725 | 1.015 | 1.215 |
| 47.3 | 0.345 | 0.6725 | 1.0175 | 1.2175 |
| 47.4 | 0.3425 | 0.6750 | 1.0175 | 1.22 |
| 47.5 | 0.345 | 0.6750 | 1.02 | 1.2225 |
| 47.6 | 0.345 | 0.6775 | 1.0225 | 1.2275 |
| 47.7 | 0.3475 | 0.6800 | 1.0275 | 1.2325 |
| 47.8 | 0.3475 | 0.6825 | 1.03 | 1.235 |
| 47.9 | 0.35 | 0.6825 | 1.0325 | 1.2375 |
| 48.0 | 0.35 | 0.6850 | 1.035 | 1.24 |
| 48.1 | 0.3525 | 0.6850 | 1.0375 | 1.2425 |
| 48.2 | 0.3525 | 0.6900 | 1.0425 | 1.2475 |
| 48.3 | 0.3525 | 0.6925 | 1.045 | 1.25 |
| 43.4 | 0.355 | 0.6925 | 1.0475 | 1.255 |
| 48.5 | 0.3525 | 0.6950 | 1.0475 | 1.2575 |
| 48.6 | 0.355 | 0.6950 | 1.05 | 1.26 |
| 48.7 | 0.355 | 0.6975 | 1.0525 | 1.2625 |
| 48.8 | 0.355 | 0.7000 | 1.055 | 1.265 |
| 48.9 | 0.3575 | 0.7000 | 1.0575 | 1.27 |
| 49.0 | 0.3575 | 0.7050 | 1.0625 | 1.275 |
| 49.1 | 0.36 | 0.7050 | 1.065 | 1.2775 |
| 49.2 | 0.36 | 0.7075 | 1.0675 | 1.28 |
| 49.3 | 0.36 | 0.7100 | 1.07 | 1.2825 |
| 49.4 | 0.3625 | 0.7100 | 1.0725 | 1.2875 |
| 49.5 | 0.3625 | 0.7125 | 1.075 | 1.29 |
| 49.6 | 0.3625 | 0.7150 | 1.0775 | 1.2925 |
| 49.7 | 0.365 | 0.7150 | 1.08 | 1.295 |
| 49.8 | 0.3675 | 0.7175 | 1.085 | 1.3 |
| 49.9 | 0.3675 | 0.7200 | 1.0875 | 1.3025 |
| 50.0 | 0.37 | 0.7200 | 1.09 | 1.305 |
| 50.1 | 0.37 | 0.7225 | 1.0925 | 1.3075 |
| 50.2 | 0.37 | 0.7250 | 1.095 | 1.3125 |
| 50.3 | 0.37 | 0.7275 | 1.0975 | 1.315 |
| 50.4 | 0.3725 | 0.7275 | 1.1 | 1.3175 |
| 50.5 | 0.3725 | 0.7300 | 1.1025 | 1.3225 |
| 50.6 | 0.3725 | 0.7325 | 1.105 | 1.325 |

APPENDIX 3-continued

| Lookup mass as function of dP (inside) | | | | |
|---|---|---|---|---|
| | Delta T | | | |
| | 5 C. Delta | 10 C. Delta | 15 C. Delta | 18 C. Delta |
| 50.7 | 0.375 | 0.7325 | 1.1075 | 1.3275 |
| 50.8 | 0.375 | 0.7350 | 1.11 | 1.3325 |
| 50.9 | 0.375 | 0.7375 | 1.1125 | 1.335 |
| 51.0 | 0.3775 | 0.7400 | 1.1175 | 1.3375 |
| 51.1 | 0.38 | 0.7400 | 1.12 | 1.3425 |
| 51.2 | 0.38 | 0.7425 | 1.1225 | 1.345 |
| 51.3 | 0.38 | 0.7450 | 1.125 | 1.3475 |
| 51.4 | 0.38 | 0.7475 | 1.1275 | 1.3525 |
| 51.5 | 0.38 | 0.7500 | 1.13 | 1.355 |
| 51.6 | 0.385 | 0.7500 | 1.135 | 1.36 |
| 51.7 | 0.385 | 0.7525 | 1.1375 | 1.3625 |
| 51.8 | 0.385 | 0.7550 | 1.14 | 1.365 |
| 51.9 | 0.385 | 0.7550 | 1.14 | 1.3675 |
| 52.0 | 0.385 | 0.7575 | 1.1425 | 1.37 |
| 52.1 | 0.385 | 0.7600 | 1.145 | 1.375 |
| 52.2 | 0.39 | 0.7600 | 1.15 | 1.3775 |
| 52.3 | 0.39 | 0.7625 | 1.1525 | 1.38 |
| 52.4 | 0.39 | 0.7650 | 1.155 | 1.385 |
| 52.5 | 0.39 | 0.7675 | 1.1575 | 1.3875 |
| 52.6 | 0.3925 | 0.7700 | 1.1625 | 1.3925 |
| 52.7 | 0.3925 | 0.7700 | 1.1625 | 1.3925 |
| 52.8 | 0.3925 | 0.7725 | 1.165 | 1.3975 |
| 52.9 | 0.395 | 0.7725 | 1.1675 | 1.4 |
| 53.0 | 0.3975 | 0.7750 | 1.1725 | 1.405 |
| 53.1 | 0.3975 | 0.7775 | 1.175 | 1.4075 |
| 53.2 | 0.3975 | 0.7800 | 1.1775 | 1.4125 |
| 53.3 | 0.3975 | 0.7800 | 1.1775 | 1.4125 |
| 53.4 | 0.4 | 0.7825 | 1.1825 | 1.415 |
| 53.5 | 0.4 | 0.7850 | 1.185 | 1.42 |
| 53.6 | 0.4 | 0.7875 | 1.1875 | 1.4225 |
| 53.7 | 0.4025 | 0.7900 | 1.1925 | 1.4275 |
| 53.8 | 0.4025 | 0.7925 | 1.195 | 1.4325 |
| 53.9 | 0.4025 | 0.7925 | 1.195 | 1.4325 |
| 54.0 | 0.4025 | 0.7950 | 1.1975 | 1.4375 |
| 54.1 | 0.4075 | 0.7950 | 1.2025 | 1.44 |
| 54.2 | 0.4075 | 0.7975 | 1.205 | 1.445 |
| 54.3 | 0.4075 | 0.7975 | 1.205 | 1.445 |
| 54.4 | 0.41 | 0.8000 | 1.21 | 1.45 |
| 54.5 | 0.41 | 0.8025 | 1.2125 | 1.4525 |
| 54.6 | 0.41 | 0.8050 | 1.215 | 1.4575 |
| 54.7 | 0.4125 | 0.8050 | 1.2175 | 1.4575 |
| 54.8 | 0.4125 | 0.8075 | 1.22 | 1.4625 |
| 54.9 | 0.4125 | 0.8100 | 1.2225 | 1.465 |
| 55.0 | 0.415 | 0.8125 | 1.2275 | 1.47 |
| 55.1 | 0.415 | 0.8125 | 1.2275 | 1.4725 |
| 55.2 | 0.4175 | 0.8150 | 1.2325 | 1.475 |
| 55.3 | 0.4175 | 0.8175 | 1.235 | 1.48 |
| 55.4 | 0.4175 | 0.8175 | 1.235 | 1.48 |
| 55.5 | 0.42 | 0.8200 | 1.24 | 1.485 |
| 55.6 | 0.42 | 0.8225 | 1.2425 | 1.49 |
| 55.7 | 0.4225 | 0.8250 | 1.2475 | 1.4925 |
| 55.8 | 0.4225 | 0.8250 | 1.2475 | 1.495 |
| 55.9 | 0.4225 | 0.8275 | 1.25 | 1.4975 |
| 56.0 | 0.4225 | 0.8325 | 1.255 | 1.5025 |
| 56.1 | 0.4225 | 0.8325 | 1.255 | 1.505 |
| 56.2 | 0.425 | 0.8350 | 1.26 | 1.5075 |
| 56.3 | 0.425 | 0.8375 | 1.2625 | 1.5125 |
| 56.4 | 0.425 | 0.8375 | 1.2625 | 1.515 |
| 56.5 | 0.4275 | 0.8400 | 1.2675 | 1.5175 |
| 56.6 | 0.4275 | 0.8425 | 1.27 | 1.5225 |
| 56.7 | 0.43 | 0.8425 | 1.2725 | 1.525 |
| 56.8 | 0.43 | 0.8450 | 1.275 | 1.5275 |
| 56.9 | 0.4325 | 0.8475 | 1.28 | 1.5325 |
| 57.0 | 0.4325 | 0.8475 | 1.28 | 1.535 |
| 57.1 | 0.435 | 0.8500 | 1.285 | 1.5375 |
| 57.2 | 0.435 | 0.8500 | 1.285 | 1.54 |
| 57.3 | 0.4325 | 0.8550 | 1.2875 | 1.545 |
| 57.4 | 0.435 | 0.8575 | 1.2925 | 1.5475 |
| 57.5 | 0.435 | 0.8575 | 1.2925 | 1.55 |
| 57.6 | 0.4375 | 0.8600 | 1.2975 | 1.555 |
| 57.7 | 0.4375 | 0.8625 | 1.3 | 1.5575 |
| 57.8 | 0.44 | 0.8625 | 1.3025 | 1.56 |
| 57.9 | 0.44 | 0.8650 | 1.305 | 1.565 |
| 58.0 | 0.4425 | 0.8650 | 1.3075 | 1.565 |

APPENDIX 3-continued

| Lookup mass as function of dP (inside) | | | | |
|---|---|---|---|---|
| | Delta T | | | |
| | 5 C. Delta | 10 C. Delta | 15 C. Delta | 18 C. Delta |
| 58.1 | 0.44 | 0.8700 | 1.31 | 1.57 |
| 58.2 | 0.4425 | 0.8725 | 1.315 | 1.575 |
| 58.3 | 0.4425 | 0.8725 | 1.315 | 1.5775 |
| 58.4 | 0.445 | 0.8750 | 1.32 | 1.58 |
| 58.5 | 0.445 | 0.8750 | 1.32 | 1.5825 |
| 58.6 | 0.4475 | 0.8775 | 1.325 | 1.5875 |
| 58.7 | 0.445 | 0.8800 | 1.325 | 1.5875 |
| 58.8 | 0.4475 | 0.8825 | 1.33 | 1.5925 |
| 58.9 | 0.4475 | 0.8850 | 1.3325 | 1.5975 |
| 59.0 | 0.45 | 0.8850 | 1.335 | 1.6 |
| 59.1 | 0.4525 | 0.8875 | 1.34 | 1.6025 |
| 59.2 | 0.4525 | 0.8875 | 1.34 | 1.605 |
| 59.3 | 0.4525 | 0.8925 | 1.345 | 1.61 |
| 59.4 | 0.4525 | 0.8925 | 1.345 | 1.6125 |
| 59.5 | 0.455 | 0.8950 | 1.35 | 1.615 |
| 59.6 | 0.455 | 0.8950 | 1.35 | 1.6175 |
| 59.7 | 0.4575 | 0.8975 | 1.355 | 1.6225 |
| 59.8 | 0.455 | 0.9000 | 1.355 | 1.625 |
| 59.9 | 0.4575 | 0.9025 | 1.36 | 1.6275 |
| 60.0 | 0.46 | 0.9025 | 1.3625 | 1.63 |
| 60.1 | 0.46 | 0.9050 | 1.365 | 1.635 |
| 60.2 | 0.4625 | 0.9050 | 1.3675 | 1.6375 |
| 60.3 | 0.46 | 0.9100 | 1.37 | 1.6425 |
| 60.4 | 0.4625 | 0.9125 | 1.375 | 1.645 |
| 60.5 | 0.4625 | 0.9125 | 1.375 | 1.6475 |
| 60.6 | 0.465 | 0.9150 | 1.38 | 1.6525 |
| 60.7 | 0.465 | 0.9175 | 1.3825 | 1.655 |
| 60.8 | 0.465 | 0.9200 | 1.385 | 1.6575 |
| 60.9 | 0.4675 | 0.9200 | 1.3875 | 1.66 |
| 61.0 | 0.4675 | 0.9200 | 1.3875 | 1.6625 |
| 61.1 | 0.47 | 0.9225 | 1.3925 | 1.6675 |
| 61.2 | 0.47 | 0.9250 | 1.395 | 1.67 |
| 61.3 | 0.47 | 0.9275 | 1.3975 | 1.6725 |
| 61.4 | 0.4725 | 0.9275 | 1.4 | 1.675 |
| 61.5 | 0.4725 | 0.9300 | 1.4025 | 1.68 |
| 61.6 | 0.4725 | 0.9325 | 1.405 | 1.6825 |
| 61.7 | 0.475 | 0.9350 | 1.41 | 1.6875 |
| 61.8 | 0.475 | 0.9350 | 1.41 | 1.69 |
| 61.9 | 0.475 | 0.9400 | 1.415 | 1.6925 |
| 62.0 | 0.4775 | 0.9400 | 1.4175 | 1.695 |
| 62.1 | 0.4775 | 0.9425 | 1.42 | 1.7 |
| 62.2 | 0.48 | 0.9425 | 1.4225 | 1.7025 |
| 62.3 | 0.4775 | 0.9475 | 1.425 | 1.7075 |
| 62.4 | 0.48 | 0.9475 | 1.4275 | 1.71 |
| 62.5 | 0.4825 | 0.9475 | 1.43 | 1.71 |
| 62.6 | 0.48 | 0.9525 | 1.4325 | 1.715 |
| 62.7 | 0.4825 | 0.9525 | 1.435 | 1.7175 |
| 62.8 | 0.485 | 0.9550 | 1.44 | 1.7225 |
| 62.9 | 0.485 | 0.9550 | 1.44 | 1.725 |
| 63.0 | 0.435 | 0.9600 | 1.445 | 1.73 |
| 63.1 | 0.4875 | 0.9600 | 1.4475 | 1.73 |
| 63.2 | 0.4875 | 0.9625 | 1.45 | 1.735 |
| 63.3 | 0.4875 | 0.9650 | 1.4525 | 1.7375 |
| 63.4 | 0.49 | 0.9650 | 1.455 | 1.74 |
| 63.5 | 0.49 | 0.9675 | 1.4575 | 1.745 |
| 63.6 | 0.49 | 0.9700 | 1.46 | 1.7475 |
| 63.7 | 0.4925 | 0.9725 | 1.465 | 1.7525 |
| 63.8 | 0.4925 | 0.9725 | 1.465 | 1.7525 |
| 63.9 | 0.495 | 0.9725 | 1.4675 | 1.755 |
| 64.0 | 0.495 | 0.9775 | 1.4725 | 1.76 |
| 64.1 | 0.495 | 0.9775 | 1.4725 | 1.7625 |
| 64.2 | 0.4975 | 0.9800 | 1.4775 | 1.7675 |
| 64.3 | 0.4975 | 0.9825 | 1.48 | 1.77 |
| 64.4 | 0.4975 | 0.9850 | 1.4825 | 1.775 |
| 64.5 | 0.5 | 0.9850 | 1.485 | 1.7775 |
| 64.6 | 0.5 | 0.9875 | 1.4875 | 1.7775 |
| 64.7 | 0.5 | 0.9900 | 1.49 | 1.7825 |
| 64.8 | 0.5025 | 0.9900 | 1.4925 | 1.785 |
| 64.9 | 0.5025 | 0.9950 | 1.4975 | 1.79 |
| 65.0 | 0.5025 | 0.9950 | 1.4975 | 1.7925 |
| 65.1 | 0.505 | 0.9950 | 1.5 | 1.795 |
| 65.2 | 0.505 | 1.0000 | 1.505 | 1.8 |
| 65.3 | 0.505 | 1.0000 | 1.505 | 1.8025 |
| 65.4 | 0.505 | 1.0025 | 1.5075 | 1.805 |

APPENDIX 3-continued

| Lookup mass as function of dP (inside) | | | | |
|---|---|---|---|---|
| | Delta T | | | |
| | 5 C. Delta | 10 C. Delta | 15 C. Delta | 18 C. Delta |
| 65.5 | 0.5075 | 1.0050 | 1.5125 | 1.8075 |
| 65.6 | 0.51 | 1.0050 | 1.515 | 1.81 |
| 65.7 | 0.5075 | 1.0100 | 1.5175 | 1.815 |
| 65.8 | 0.51 | 1.0100 | 1.52 | 1.8175 |
| 65.9 | 0.5125 | 1.0100 | 1.5225 | 1.82 |
| 66.0 | 0.51 | 1.0150 | 1.525 | 1.825 |
| 66.1 | 0.5125 | 1.0150 | 1.5275 | 1.8275 |
| 66.2 | 0.515 | 1.0150 | 1.53 | 1.83 |
| 66.3 | 0.515 | 1.0200 | 1.535 | 1.835 |
| 66.4 | 0.515 | 1.0200 | 1.535 | 1.8375 |
| 66.5 | 0.5175 | 1.0225 | 1.54 | 1.84 |
| 66.6 | 0.5175 | 1.0250 | 1.5425 | 1.8425 |
| 66.7 | 0.5175 | 1.0250 | 1.5425 | 1.845 |
| 66.8 | 0.5175 | 1.0300 | 1.5475 | 1.85 |
| 66.9 | 0.52 | 1.0300 | 1.55 | 1.8525 |
| 67.0 | 0.5225 | 1.0300 | 1.5525 | 1.855 |
| 67.1 | 0.52 | 1.0350 | 1.555 | 1.86 |
| 67.2 | 0.5225 | 1.0350 | 1.5675 | 1.8625 |
| 67.3 | 0.525 | 1.0375 | 1.5625 | 1.8675 |
| 67.4 | 0.5225 | 1.0400 | 1.5625 | 1.87 |
| 67.5 | 0.525 | 1.0400 | 1.565 | 1.8725 |
| 67.6 | 0.525 | 1.0450 | 1.57 | 1.8775 |
| 67.7 | 0.5275 | 1.0450 | 1.5725 | 1.8775 |
| 67.8 | 0.5275 | 1.0450 | 1.5725 | 1.88 |
| 67.9 | 0.5275 | 1.0500 | 1.5775 | 1.885 |
| 68.0 | 0.53 | 1.0500 | 1.58 | 1.8875 |
| 68.1 | 0.53 | 1.0525 | 1.5825 | 1.89 |
| 68.2 | 0.53 | 1.0550 | 1.585 | 1.895 |
| 68.3 | 0.5325 | 1.0550 | 1.5875 | 1.8975 |
| 68.4 | 0.5325 | 1.0575 | 1.59 | 1.9 |
| 68.5 | 0.535 | 1.0600 | 1.595 | 1.905 |
| 68.6 | 0.5325 | 1.0625 | 1.595 | 1.9075 |
| 68.7 | 0.535 | 1.0625 | 1.5975 | 1.91 |
| 68.8 | 0.5375 | 1.0650 | 1.6025 | 1.915 |
| 68.9 | 0.535 | 1.0675 | 1.6025 | 1.9175 |
| 69.0 | 0.5375 | 1.0675 | 1.605 | 1.92 |
| 69.1 | 0.5375 | 1.0725 | 1.61 | 1.9225 |
| 69.2 | 0.54 | 1.0725 | 1.6125 | 1.925 |
| 69.3 | 0.54 | 1.0750 | 1.615 | 1.93 |
| 69.4 | 0.54 | 1.0775 | 1.6175 | 1.9325 |
| 69.5 | 0.5425 | 1.0775 | 1.62 | 1.935 |
| 69.6 | 0.5425 | 1.0825 | 1.625 | 1.94 |
| 69.7 | 0.5425 | 1.0825 | 1.625 | 1.9425 |
| 69.8 | 0.545 | 1.0825 | 1.6275 | 1.945 |
| 69.9 | 0.545 | 1.0875 | 1.6325 | 1.95 |
| 70.0 | 0.5475 | 1.0875 | 1.635 | 1.9525 |
| 70.1 | 0.545 | 1.0900 | 1.635 | 1.955 |
| 70.2 | 0.5475 | 1.0925 | 1.64 | 1.96 |
| 70.3 | 0.55 | 1.0925 | 1.6425 | 1.9625 |
| 70.4 | 0.55 | 1.0950 | 1.645 | 1.965 |
| 70.5 | 0.5525 | 1.0975 | 1.65 | 1.97 |
| 70.6 | 0.55 | 1.1000 | 1.65 | 1.9725 |
| 70.7 | 0.5525 | 1.1000 | 1.6525 | 1.975 |
| 70.8 | 0.555 | 1.1025 | 1.6575 | 1.98 |
| 70.9 | 0.555 | 1.1050 | 1.66 | 1.98 |
| 71.0 | 0.555 | 1.1050 | 1.66 | 1.9825 |
| 71.1 | 0.555 | 1.1100 | 1.665 | 1.9875 |
| 71.2 | 0.5575 | 1.1100 | 1.6675 | 1.99 |
| 71.3 | 0.5575 | 1.1125 | 1.67 | 1.9925 |
| 71.4 | 0.5575 | 1.1150 | 1.6725 | 1.9975 |
| 71.5 | 0.56 | 1.1150 | 1.675 | 2 |
| 71.6 | 0.56 | 1.1175 | 1.6775 | 2.0025 |
| 71.7 | 0.5625 | 1.1200 | 1.6825 | 2.0075 |
| 71.8 | 0.56 | 1.1225 | 1.6825 | 2.01 |
| 71.9 | 0.5625 | 1.1225 | 1.685 | 2.0125 |
| 72.0 | 0.565 | 1.1250 | 1.69 | 2.0175 |
| 72.1 | 0.565 | 1.1275 | 1.6925 | 2.02 |
| 72.2 | 0.565 | 1.1275 | 1.6925 | 2.0225 |
| 72.3 | 0.565 | 1.1325 | 1.6975 | 2.0275 |
| 72.4 | 0.5675 | 1.1325 | 1.7 | 2.03 |
| 72.5 | 0.5675 | 1.1359 | 1.7025 | 2.0325 |
| 72.6 | 0.57 | 1.1375 | 1.7075 | 2.0375 |
| 72.7 | 0.57 | 1.1375 | 1.7075 | 2.04 |
| 72.8 | 0.57 | 1.1400 | 1.71 | 2.0425 |

APPENDIX 3-continued

| Lookup mass as function of dP (inside) | | | | |
|---|---|---|---|---|
| | Delta T | | | |
| | 5 C. Delta | 10 C. Delta | 15 C. Delta | 18 C. Delta |
| 72.9 | 0.5725 | 1.1425 | 1.715 | 2.0475 |
| 73.0 | 0.5725 | 1.1450 | 1.7175 | 2.0475 |
| 73.1 | 0.5725 | 1.1450 | 1.7175 | 2.05 |
| 73.2 | 0.575 | 1.1475 | 1.7225 | 2.055 |
| 73.3 | 0.575 | 1.1500 | 1.725 | 2.0575 |
| 73.4 | 0.5775 | 1.1500 | 1.7275 | 2.06 |
| 73.5 | 0.575 | 1.1550 | 1.73 | 2.065 |
| 73.6 | 0.5775 | 1.1550 | 1.7325 | 2.0675 |
| 73.7 | 0.5775 | 1.1575 | 1.735 | 2.07 |
| 73.8 | 0.58 | 1.1600 | 1.74 | 2.075 |
| 73.9 | 0.5825 | 1.1600 | 1.7425 | 2.0775 |
| 74.0 | 0.58 | 1.1650 | 1.745 | 2.0825 |
| 74.1 | 0.5825 | 1.1650 | 1.7475 | 2.085 |
| 74.2 | 0.5825 | 1.1675 | 1.75 | 2.0875 |
| 74.3 | 0.585 | 1.1700 | 1.755 | 2.0925 |
| 74.4 | 0.5825 | 1.1725 | 1.755 | 2.095 |
| 74.5 | 0.585 | 1.1725 | 1.7575 | 2.0975 |
| 74.6 | 0.5875 | 1.1750 | 1.7625 | 2.1025 |
| 74.7 | 0.5875 | 1.1775 | 1.765 | 2.105 |
| 74.8 | 0.5875 | 1.1775 | 1.765 | 2.1075 |
| 74.9 | 0.5875 | 1.1825 | 1.77 | 2.1125 |
| 75.0 | 0.59 | 1.1825 | 1.7725 | 2.115 |
| 75.1 | 0.5925 | 1.1825 | 1.775 | 2.1175 |
| 75.2 | 0.5925 | 1.1875 | 1.78 | 2.1225 |
| 75.3 | 0.5925 | 1.1875 | 1.78 | 2.125 |
| 75.4 | 0.5925 | 1.1900 | 1.7825 | 2.1275 |
| 75.5 | 0.595 | 1.1925 | 1.7875 | 2.13 |
| 75.6 | 0.595 | 1.1950 | 1.79 | 2.1325 |
| 75.7 | 0.595 | 1.1975 | 1.7925 | 2.1375 |
| 75.8 | 0.5975 | 1.1975 | 1.795 | 2.14 |
| 75.9 | 0.5975 | 1.2000 | 1.7975 | 2.1425 |
| 76.0 | 0.6 | 1.2025 | 1.8025 | 2.1475 |
| 76.1 | 0.5975 | 1.2050 | 1.8025 | 2.15 |
| 76.2 | 0.6 | 1.2050 | 1.805 | 2.1525 |
| 76.3 | 0.6025 | 1.2075 | 1.81 | 2.1575 |
| 76.4 | 0.6025 | 1.2100 | 1.8125 | 2.16 |
| 76.5 | 0.605 | 1.2125 | 1.8175 | 2.165 |
| 76.6 | 0.6025 | 1.2150 | 1.8175 | 2.1675 |
| 76.7 | 0.605 | 1.2150 | 1.82 | 2.17 |
| 76.8 | 0.6075 | 1.2175 | 1.825 | 2.175 |
| 76.9 | 0.6075 | 1.2200 | 1.8275 | 2.1775 |
| 77.0 | 0.6075 | 1.2200 | 1.8275 | 2.18 |
| 77.1 | 0.6075 | 1.2250 | 1.8325 | 2.185 |
| 77.2 | 0.61 | 1.2250 | 1.835 | 2.1875 |
| 77.3 | 0.61 | 1.2300 | 1.84 | 2.1925 |
| 77.4 | 0.61 | 1.2300 | 1.84 | 2.195 |
| 77.5 | 0.6125 | 1.2300 | 1.8425 | 2.1975 |
| 77.6 | 0.6125 | 1.2350 | 1.8475 | 2.2025 |
| 77.7 | 0.615 | 1.2350 | 1.85 | 2.205 |
| 77.8 | 0.615 | 1.2400 | 1.855 | 2.21 |
| 77.9 | 0.615 | 1.2400 | 1.855 | 2.2125 |
| 78.0 | 0.6175 | 1.2400 | 1.8575 | 2.2125 |
| 78.1 | 0.6175 | 1.2450 | 1.8625 | 2.2175 |
| 78.2 | 0.62 | 1.2450 | 1.865 | 2.22 |
| 78.3 | 0.6175 | 1.2500 | 1.8675 | 2.225 |
| 78.4 | 0.62 | 1.2500 | 1.87 | 2.2275 |
| 78.5 | 0.6225 | 1.2500 | 1.8725 | 2.23 |
| 78.6 | 0.6225 | 1.2550 | 1.8775 | 2.235 |
| 78.7 | 0.6225 | 1.2550 | 1.8775 | 2.2375 |
| 78.8 | 0.625 | 1.2575 | 1.8825 | 2.2425 |
| 78.9 | 0.625 | 1.2600 | 1.885 | 2.245 |
| 79.0 | 0.6275 | 1.2625 | 1.89 | 2.25 |
| 79.1 | 0.625 | 1.2650 | 1.89 | 2.2525 |
| 79.2 | 0.6275 | 1.2650 | 1.8925 | 2.255 |
| 79.3 | 0.63 | 1.2675 | 1.8975 | 2.26 |
| 79.4 | 0.63 | 1.2700 | 1.9 | 2.2625 |
| 79.5 | 0.63 | 1.2725 | 1.9025 | 2.2675 |
| 79.6 | 0.63 | 1.2750 | 1.905 | 2.27 |
| 79.7 | 0.6325 | 1.2775 | 1.91 | 2.275 |
| 79.8 | 0.635 | 1.2775 | 1.9125 | 2.2775 |
| 79.9 | 0.6325 | 1.2825 | 1.915 | 2.2825 |
| 80.0 | 0.635 | 1.2825 | 1.9175 | 2.285 |
| 80.1 | 0.6375 | 1.2825 | 1.92 | 2.2875 |
| 80.2 | 0.6375 | 1.2875 | 1.925 | 2.2925 |

APPENDIX 3-continued

Lookup mass as function of dP (inside)

| | Delta T | | | |
|---|---|---|---|---|
| | 5 C. Delta | 10 C. Delta | 15 C. Delta | 18 C. Delta |
| 80.3 | 0.6375 | 1.2875 | 1.925 | 2.2925 |
| 80.4 | 0.6375 | 1.2925 | 1.93 | 2.2975 |
| 80.5 | 0.64 | 1.2925 | 1.9325 | 2.3 |
| 80.6 | 0.6425 | 1.2950 | 1.9375 | 2.305 |
| 80.7 | 0.64 | 1.2975 | 1.9375 | 2.3075 |
| 80.8 | 0.6425 | 1.3000 | 1.9425 | 2.3125 |
| 80.9 | 0.645 | 1.3000 | 1.945 | 2.315 |
| 81.0 | 0.645 | 1.3050 | 1.95 | 2.32 |
| 81.1 | 0.645 | 1.3059 | 1.95 | 2.3225 |
| 81.2 | 0.6475 | 1.3075 | 1.955 | 2.3275 |
| 81.3 | 0.6475 | 1.3100 | 1.9575 | 2.33 |
| 81.4 | 0.65 | 1.3125 | 1.9625 | 2.335 |
| 81.5 | 0.6475 | 1.3150 | 1.9625 | 2.3375 |
| 81.6 | 0.65 | 1.3175 | 1.9675 | 2.3425 |
| 81.7 | 0.6525 | 1.3175 | 1.97 | 2.345 |
| 81.8 | 0.6525 | 1.3225 | 1.975 | 2.35 |
| 81.9 | 0.6525 | 1.3225 | 1.975 | 2.3525 |
| 82.0 | 0.655 | 1.3250 | 1.98 | 2.3575 |
| 82.1 | 0.655 | 1.3275 | 1.9825 | 2.36 |
| 82.2 | 0.6575 | 1.3300 | 1.9875 | 2.3625 |
| 82.3 | 0.6575 | 1.3300 | 1.9875 | 2.365 |
| 82.4 | 0.6575 | 1.3350 | 1.9925 | 2.37 |
| 82.5 | 0.66 | 1.3350 | 1.995 | 2.3725 |
| 82.6 | 0.66 | 1.3375 | 1.9975 | 2.3775 |
| 82.7 | 0.66 | 1.3400 | 2 | 2.38 |
| 82.8 | 0.6625 | 1.3425 | 2.005 | 2.385 |
| 82.9 | 0.665 | 1.3450 | 2.01 | 2.39 |
| 83.0 | 0.6625 | 1.3475 | 2.01 | 2.3925 |
| 83.1 | 0.665 | 1.3500 | 2.015 | 2.3975 |
| 83.2 | 0.6675 | 1.3500 | 2.0175 | 2.4 |
| 83.3 | 0.6675 | 1.3550 | 2.0225 | 2.405 |
| 83.4 | 0.6675 | 1.3550 | 2.0225 | 2.4075 |
| 83.5 | 0.67 | 1.3575 | 2.0275 | 2.4125 |
| 83.6 | 0.6725 | 1.3600 | 2.0325 | 2.4175 |
| 83.7 | 0.67 | 1.3625 | 2.0325 | 2.42 |
| 83.8 | 0.6725 | 1.3650 | 2.0375 | 2.4225 |
| 83.9 | 0.675 | 1.3650 | 2.04 | 2.425 |
| 84.0 | 0.675 | 1.3700 | 2.045 | 2.43 |
| 84.1 | 0.675 | 1.3700 | 2.045 | 2.4325 |
| 84.2 | 0.6775 | 1.3725 | 2.05 | 2.4375 |
| 84.3 | 0.6775 | 1.3775 | 2.055 | 2.4425 |
| 84.4 | 0.6775 | 1.3775 | 2.055 | 2.445 |
| 84.5 | 0.68 | 1.3800 | 2.06 | 2.45 |
| 84.6 | 0.6825 | 1.3825 | 2.065 | 2.455 |
| 84.7 | 0.68 | 1.3850 | 2.065 | 2.4575 |
| 84.8 | 0.6825 | 1.3875 | 2.07 | 2.4625 |
| 84.9 | 0.685 | 1.3875 | 2.0725 | 2.465 |
| 85.0 | 0.6825 | 1.3925 | 2.075 | 2.47 |
| 85.1 | 0.685 | 1.3950 | 2.08 | 2.4725 |
| 85.2 | 0.6875 | 1.3950 | 2.0825 | 2.475 |
| 85.3 | 0.69 | 1.3975 | 2.0875 | 2.48 |
| 85.4 | 0.6875 | 1.4025 | 2.09 | 2.485 |
| 85.5 | 0.69 | 1.4025 | 2.0925 | 2.4875 |
| 85.6 | 0.6925 | 1.4050 | 2.0975 | 2.4925 |
| 85.7 | 0.6925 | 1.4075 | 2.1 | 2.4975 |
| 85.8 | 0.6925 | 1.4100 | 2.1025 | 2.5 |
| 85.9 | 0.695 | 1.4125 | 2.1075 | 2.505 |
| 86.0 | 0.695 | 1.4150 | 2.11 | 2.51 |
| 86.1 | 0.6975 | 1.4150 | 2.1125 | 2.5125 |
| 85.2 | 0.6975 | 1.4200 | 2.1175 | 2.515 |
| 86.3 | 0.6975 | 1.4225 | 2.12 | 2.52 |
| 86.4 | 0.7 | 1.4250 | 2.125 | 2.525 |
| 86.5 | 0.7025 | 1.4250 | 2.1275 | 2.5275 |
| 86.6 | 0.7 | 1.4300 | 2.13 | 2.5325 |
| 86.7 | 0.7025 | 1.4325 | 2.135 | 2.5375 |
| 86.8 | 0.705 | 1.4350 | 2.14 | 2.5425 |
| 86.9 | 0.705 | 1.4350 | 2.14 | 2.545 |
| 87.0 | 0.7075 | 1.4375 | 2.145 | 2.55 |
| 87.1 | 0.7075 | 1.4425 | 2.15 | 2.5525 |
| 87.2 | 0.7075 | 1.4450 | 2.1525 | 2.5575 |
| 87.3 | 0.71 | 1.4450 | 2.155 | 2.56 |
| 87.4 | 0.71 | 1.4475 | 2.1575 | 2.565 |
| 87.5 | 0.7125 | 1.4500 | 2.1625 | 2.57 |
| 87.6 | 0.7125 | 1.4550 | 2.1675 | 2.575 |

APPENDIX 3-continued

Lookup mass as function of dP (inside)

| | Delta T | | | |
|---|---|---|---|---|
| | 5 C. Delta | 10 C. Delta | 15 C. Delta | 18 C. Delta |
| 87.7 | 0.7125 | 1.4550 | 2.1675 | 2.5775 |
| 87.8 | 0.715 | 1.4575 | 2.1725 | 2.5825 |
| 87.9 | 0.7175 | 1.4600 | 2.1775 | 2.5875 |
| 88.0 | 0.7175 | 1.4625 | 2.18 | 2.59 |
| 88.1 | 0.72 | 1.4650 | 2.185 | 2.595 |
| 88.2 | 0.72 | 1.4675 | 2.1875 | 2.5975 |
| 88.3 | 0.72 | 1.4700 | 2.19 | 2.6025 |
| 88.4 | 0.7225 | 1.4725 | 2.195 | 2.6075 |
| 88.5 | 0.7225 | 1.4750 | 2.1975 | 2.6125 |
| 88.6 | 0.725 | 1.4775 | 2.2025 | 2.6175 |
| 88.7 | 0.7275 | 1.4800 | 2.2075 | 2.62 |
| 88.8 | 0.7275 | 1.4825 | 2.21 | 2.625 |
| 88.9 | 0.7275 | 1.4850 | 2.2125 | 2.6275 |
| 89.0 | 0.7275 | 1.4875 | 2.215 | 2.6325 |
| 89.1 | 0.73 | 1.4900 | 2.22 | 2.6375 |
| 89.2 | 0.7325 | 1.4925 | 2.225 | 2.6425 |
| 89.3 | 0.7325 | 1.4950 | 2.2275 | 2.6475 |
| 89.4 | 0.735 | 1.4975 | 2.2325 | 2.65 |
| 89.5 | 0.735 | 1.5000 | 2.235 | 2.655 |
| 89.6 | 0.7375 | 1.5025 | 2.24 | 2.66 |
| 89.7 | 0.7375 | 1.5050 | 2.2425 | 2.665 |
| 89.8 | 0.7375 | 1.5100 | 2.2475 | 2.67 |
| 89.9 | 0.74 | 1.5125 | 2.2525 | 2.675 |
| 90.0 | 0.74 | 1.5125 | 2.2525 | 2.675 |
| 90.1 | 0.7425 | 1.5175 | 2.26 | 2.6825 |
| 90.2 | 0.7425 | 1.5175 | 2.26 | 2.685 |
| 90.3 | 0.745 | 1.5200 | 2.265 | 2.69 |
| 90.4 | 0.745 | 1.5225 | 2.2675 | 2.695 |
| 90.5 | 0.7475 | 1.5250 | 2.2725 | 2.7 |
| 90.6 | 0.75 | 1.5275 | 2.2775 | 2.7025 |
| 90.7 | 0.75 | 1.5300 | 2.28 | 2.7075 |
| 90.8 | 0.7525 | 1.5325 | 2.285 | 2.7125 |
| 90.9 | 0.7525 | 1.5350 | 2.2875 | 2.7175 |
| 91.0 | 0.755 | 1.5375 | 2.2925 | 2.7225 |
| 91.1 | 0.755 | 1.5425 | 2.2975 | 2.7275 |
| 91.2 | 0.7575 | 1.5450 | 2.3025 | 2.7325 |
| 91.3 | 0.7575 | 1.5475 | 2.305 | 2.7325 |
| 91.4 | 0.76 | 1.5500 | 2.31 | 2.7425 |
| 91.5 | 0.76 | 1.5525 | 2.3125 | 2.7475 |
| 91.6 | 0.7625 | 1.5550 | 2.3175 | 2.75 |
| 91.7 | 0.7625 | 1.5575 | 2.32 | 2.755 |
| 91.8 | 0.765 | 1.5600 | 2.325 | 2.76 |
| 91.9 | 0.765 | 1.5625 | 2.3275 | 2.765 |
| 92.0 | 0.7675 | 1.5650 | 2.3325 | 2.7675 |
| 92.1 | 0.7675 | 1.5675 | 2.335 | 2.7725 |
| 92.2 | 0.77 | 1.5725 | 2.3425 | 2.73 |
| 92.3 | 0.77 | 1.5750 | 2.345 | 2.785 |
| 92.4 | 0.7725 | 1.5775 | 2.35 | 2.79 |
| 92.5 | 0.7725 | 1.5800 | 2.3525 | 2.7925 |
| 92.6 | 0.7725 | 1.5825 | 2.355 | 2.7975 |
| 92.7 | 0.775 | 1.5850 | 2.36 | 2.8025 |
| 92.8 | 0.775 | 1.5875 | 2.3625 | 2.8075 |
| 92.9 | 0.7775 | 1.5925 | 2.37 | 2.8125 |
| 93.0 | 0.7775 | 1.5950 | 2.3725 | 2.8175 |
| 93.1 | 0.78 | 1.5975 | 2.3775 | 2.8225 |
| 93.2 | 0.7825 | 1.5975 | 2.38 | 2.825 |
| 93.3 | 0.785 | 1.6025 | 2.3875 | 2.8325 |
| 93.4 | 0.785 | 1.6050 | 2.39 | 2.8375 |
| 93.5 | 0.785 | 1.6075 | 2.3925 | 2.8425 |
| 93.6 | 0.7875 | 1.6100 | 2.3975 | 2.845 |
| 93.7 | 0.7875 | 1.6150 | 2.4025 | 2.8525 |
| 93.8 | 0.79 | 1.6175 | 2.4075 | 2.8575 |
| 93.9 | 0.7925 | 1.6175 | 2.41 | 2.66 |
| 94.0 | 0.7925 | 1.6225 | 2.415 | 2.8675 |
| 94.1 | 0.795 | 1.6250 | 2.42 | 2.8725 |
| 94.2 | 0.795 | 1.6275 | 2.4225 | 2.875 |
| 94.3 | 0.795 | 1.6325 | 2.4275 | 2.8825 |
| 94.4 | 0.7975 | 1.6350 | 2.4325 | 2.6875 |
| 94.5 | 0.8 | 1.6350 | 2.435 | 2.8925 |
| 94.6 | 0.8025 | 1.6400 | 2.4425 | 2.8975 |
| 94.7 | 0.3025 | 1.6425 | 2.445 | 2.9025 |
| 94.8 | 0.8025 | 1.6450 | 2.4475 | 2.905 |
| 94.9 | 0.8075 | 1.6475 | 2.455 | 2.9125 |
| 95.0 | 0.8075 | 1.6500 | 2.4575 | 2.9175 |

APPENDIX 3-continued

| Lookup mass as function of dP (inside) | | | | |
|---|---|---|---|---|
| | Delta T | | | |
| | 5 C. Delta | 10 C. Delta | 15 C. Delta | 18 C. Delta |
| 95.1 | 0.8075 | 1.6550 | 2.4625 | 2.9225 |
| 95.2 | 0.31 | 1.6575 | 2.4675 | 2.9275 |
| 95.3 | 0.81 | 1.6600 | 2.47 | 2.9325 |
| 95.4 | 0.8125 | 1.6625 | 2.475 | 2.9375 |
| 95.5 | 0.8125 | 1.6650 | 2.4775 | 2.9425 |
| 95.6 | 0.815 | 1.6700 | 2.485 | 2.95 |
| 95.7 | 0.3175 | 1.6700 | 2.4875 | 2.9525 |
| 95.8 | 0.8175 | 1.6750 | 2.4925 | 2.96 |
| 95.9 | 0.82 | 1.6775 | 2.4975 | 2.9625 |
| 96.0 | 0.8225 | 1.6800 | 2.5025 | 2.97 |
| 96.1 | 0.8225 | 1.6850 | 2.5075 | 2.9775 |
| 96.2 | 0.8225 | 1.6875 | 2.51 | 2.93 |
| 96.3 | 0.8275 | 1.6900 | 2.5175 | 2.9875 |
| 96.4 | 0.8275 | 1.6925 | 2.52 | 2.99 |
| 96.5 | 0.8275 | 1.6975 | 2.525 | 2.9975 |
| 96.6 | 0.83 | 1.6975 | 2.5275 | 3 |
| 96.7 | 0.83 | 1.7025 | 2.5325 | 3.0075 |
| 96.8 | 0.835 | 1.7000 | 2.535 | 3.0075 |

What is claimed is:

1. A method comprising:

heating, with a heater, a propellant stored in a tank to a first stable temperature at a first time and to a second stable temperature at a second time;

measuring, with a pressure sensor and a temperature sensor, a first pressure and a first temperature, respectively, of the propellant in a non-ideal gas zone while the propellant is at the first stable temperature at the first time;

measuring, with the pressure sensor and the temperature sensor, a second pressure and a second temperature, respectively, of the propellant in the non-ideal gas zone while the propellant is at the second stable temperature at the second time; and determining, by executing an instruction with a processor, based on a differential pressure between the first pressure and the second pressure and a differential temperature between the first temperature and the second temperature, a mass of the propellant in the tank.

2. The method of claim 1, wherein the determining of the mass of the propellant includes comparing the differential pressure and the differential temperature to a table relating mass to temperature differentials as a function of pressure differentials.

3. The method of claim 1, wherein the propellant is xenon.

4. The method of claim 1, wherein the first time is a period of time, and the first pressure and the first temperature are an average pressure and an average temperature over the period of time.

5. The method of claim 4, wherein the period of time is approximately 48 hours.

6. The method of claim 1, wherein the tank is a propellant tank of a satellite thruster.

7. A spacecraft thruster comprising:

a tank having a propellant;

a pressure sensor and a temperature sensor disposed in the tank, the pressure sensor and the temperature sensor to measure (1) a first pressure and a first temperature of the propellant in a non-ideal gas zone while the propellant is at a first hold temperature at a first time, and (2) a second pressure and a second temperature of the propellant in the non-ideal gas zone while the propellant is at a second hold temperature at a second time; and a processor to determine a mass of the propellant in the tank based on the first pressure, the first temperature, the second pressure and the second temperature.

8. The spacecraft thruster of claim 7, wherein the processor is to determine the mass based a difference between the first pressure and the second pressure and a difference between the first temperature and the second temperature.

9. The spacecraft thruster of claim 7 further including a heater disposed in the tank.

10. The spacecraft thruster of claim 9, wherein the processor is to control the heater to maintain the propellant at the first hold temperature.

11. The spacecraft thruster of claim 10, wherein the processor is to control the heater to maintain the propellant at the second hold temperature.

12. The spacecraft thruster of claim 7, wherein the propellant is xenon.

13. A non-transitory machine readable storage medium comprising instructions that, when executed, cause a machine to at least:

adjust, using a heater controller, a temperature of a propellant stored in a tank of a satellite thruster to a first stable temperature at a first time and to a second stable temperature at a second time;

measure, using a pressure sensor and a temperature sensor, a first pressure and a first temperature, respectively, of the propellant in a non-ideal gas zone while the propellant is at the first stable temperature at the first time;

measure, using the pressure sensor and the temperature sensor, a second pressure and a second temperature, respectively, of the propellant in the non-ideal gas zone while the propellant is at the second stable temperature at the second time; and determine, based on a differential pressure between the first temperature and the second temperature and a differential temperature between the first temperature and the second temperature, a mass of the propellant in the tank.

14. The non-transitory machine readable storage medium of claim 13, wherein the instructions, when executed, cause the machine to compare the differential pressure and the differential temperature to a table relating mass to temperature differentials as a function of pressure differentials to determine the mass of the propellant.

15. The non-transitory machine readable storage medium of claim 13, wherein the first time is a first period of time, and the first pressure and the first temperature are an average pressure and an average temperature over the first period of time.

16. The non-transitory machine readable storage medium of claim 13, wherein the second time is a second period of time, and the second pressure and the second temperature are an average pressure and an average temperature over the second period of time.

17. The non-transitory machine readable storage medium of claim 13, wherein the propellant is xenon.

* * * * *